(12) United States Patent
Ackermann et al.

(10) Patent No.: US 8,129,423 B2
(45) Date of Patent: Mar. 6, 2012

(54) IMIDAZOLONE AND IMIDAZOLOIDINONE DERIVATIVES AS 11B-HSD1 INHIBITORS

(75) Inventors: Jean Ackermann, Riehen (CH); Kurt Amrein, Itingen (CH); Daniel Hunziker, Moehlin (CH); Bernd Kuhn, Liestal (CH); Alexander V. Mayweg, Basel (CH); Werner Neidhart, Hagenthal-le-Bas (FR); Tadakatsu Takahashi, Shizuoka (JP)

(73) Assignee: Hoffman-La Roche Inc., Nutley, NJ (US)

( * ) Notice: Subject to any disclaimer, the term of this patent is extended or adjusted under 35 U.S.C. 154(b) by 234 days.

(21) Appl. No.: 11/871,318

(22) Filed: Oct. 12, 2007

(65) Prior Publication Data

US 2008/0103183 A1 May 1, 2008

(30) Foreign Application Priority Data

Oct. 19, 2006 (EP) .................... 06122591

(51) Int. Cl.
*A61K 31/4152* (2006.01)
*A61K 31/4166* (2006.01)
*C07D 233/02* (2006.01)

(52) U.S. Cl. ..... 514/386; 514/391; 514/392; 548/316.4; 548/325.5; 548/300.7

(58) Field of Classification Search .......... 514/391, 514/392; 548/316.4, 325.5
See application file for complete search history.

(56) References Cited

U.S. PATENT DOCUMENTS

| 3,625,956 | A | 12/1971 | Pesterfield, Jr. |
| 6,492,397 | B1 | 12/2002 | Reitz et al. |
| 2007/0129416 | A1 | 6/2007 | Ding et al. |
| 2008/0096906 | A1 | 4/2008 | Galley et al. |
| 2008/0119535 | A1 | 5/2008 | Galley et al. |

FOREIGN PATENT DOCUMENTS

| CA | 2759514 | 3/2006 |
| EP | 0508393 | 10/1992 |
| EP | 1 864971 | 12/2007 |
| IL | 31235 | 6/1968 |
| JP | 2007 254409 | 10/2007 |
| WO | WO 02/20493 | 3/2002 |
| WO | WO 2005/108361 | 11/2005 |
| WO | WO 2006/024628 | 3/2006 |
| WO | 2007/084684 | 7/2007 |
| WO | 2008/046758 | 4/2008 |
| WO | 2008/049105 | 4/2008 |
| WO | WO 2008/044656 | 4/2008 |

OTHER PUBLICATIONS

Cited_STN_preliminary_11871318_09032009 (2009).*
By Sasaki et al, Chem. Pharm. Bull., vol. 30, No. 6, pp. 2051-2060, (1982).*
Glushkov R G et al, *Pharmaceutical Chemistry Journal*, 15:6 (1981) 387-390 XP002521612.
Lozanova KH et al, *Chemistry of Heterocyclic Compounds* 24:10 (1988) 1129-1130, XP000943854.
Heidempergher F et al *journal of Medicinal Chemistry* 40:21 (1997) 3369-3380 XP002521613.
Caranski M et al, *Journal of Physical Organic Chemistry* 14:6 (2000) 323-327 XP002521614.
Lozanova KH et al, *Journal Fuer Praktische Chemie* 331:6 (1989) 1007-1010, XP002521615.
Sasaki T et al, Chemical and Pharmaceutical Bulletin, (1982) 30:6, 2051-2060.
Canadian Office Action dated Aug. 27, 2010 in Corresponding Appl. 2,666,489.
International Search Report & Written Opinion from Singapore IPO dated Oct. 7, 2010 in Corres. Appl. 200902321-9.

* cited by examiner

*Primary Examiner* — Yong Chu
(74) *Attorney, Agent, or Firm* — George W. Johnston; Dennis P. Tramaloni; Samuel H. Megerditchian

(57) ABSTRACT

Compounds of formula

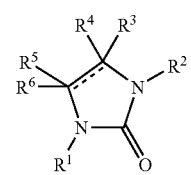

(I)

as well as pharmaceutically acceptable salts and esters thereof, wherein $R^1$ to $R^6$ have the significance given in claim 1 can be used in the form of pharmaceutical compositions.

11 Claims, No Drawings

IMIDAZOLONE AND IMIDAZOLOIDINONE DERIVATIVES AS 11B-HSD1 INHIBITORS

PRIORITY TO RELATED APPLICATION(S)

This application claims the benefit of European Patent Application No. 06122591.8, filed Oct. 19, 2006, which is hereby incorporated by reference in its entirety.

FIELD OF THE INVENTION

The present invention is concerned with novel imidazolone/imidazolidinone derivatives useful as 11b-HSD1 inhibitors (T2D).

The invention is concerned particularly with compounds of formula

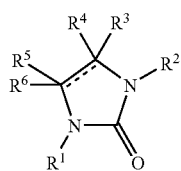

and pharmaceutically acceptable salts and esters thereof.

All document cited or relied upon below are expressly incorporated herein by reference.

BACKGROUND OF THE INVENTION

Glucocorticoids (cortisol in humans, corticosterone in mice and rats) are an important class of adrenocorticosteroids that regulate many metabolic and homeostatic processes and form a key component of the response to stress. Glucocorticoids act via intracellular glucocorticoid receptors and, in some tissues, mineralocorticoid receptors; both being nuclear transcription factors. Glucocorticoid action on target tissues depends not only on circulating steroid concentrations and the cellular expression of receptors, but also on intracellular enzymes that critically determine to which extent glucocorticoids gain access to receptors in an active forms. 11beta-hydroxysteroid dehydrogenases (11beta-HSD's) catalyze the interconversion of the principal active 11-hydroxy-glucocorticoid (cortisol in man) and their inactive 11-keto metabolites (cortisone in man).

The enzyme 11beta-hydroxysteroid dehydrogenase type 1 (11beta-HSD1) inter-converts inactive into active glucocorticoids, thereby playing a major role in local modulation of cellular agonist concentration and thus activation of corticosteroid receptors in target tissues. In a recent study made by F. Hoffmann-La Roche differences in gene expression in lean and obese man were analyzed using gene array technology in order to identify specific changes in gene expression that might be associated with insulin resistance or altered metabolism. This study revealed that the mRNA for 11beta-HSD1 is approximately two-fold up regulated in adipose tissue in obese individuals. Moreover, overexpressing 11beta-HSD1 in adipocytes of mice led to visceral obesity and to a syndrome-X like phenotype (Masuzaki H. et al., Science. 2001 Dec. 7; 294(5549):2166-70.). Taken together, these data very strongly support an important role of 11beta-HSD1 in the induction of obesity and the impairment of glucose homeostasis and lipid parameters. Thus, selective inhibition of this enzyme could lower blood glucose levels in Type 2 diabetic patients, normalize elevated lipid parameters and/or reduce weight in obese subjects.

The first pharmacological indication that 11beta-HSD1 inhibition in man might have beneficial effects were obtained by using carbenoxolone, an anti-ulcer drug which inhibits both 11beta-HSD1 and the related enzyme 11beta-HSD2. Treatment with carbenoxolone led to an increase in insulin sensitivity indicating that that inhibition of 11beta-HSD1 may reduce cellular cortisol levels and therefore minimizing some of its deleterious effects. (Walker et al. 1995; J. Clin. Endocrinol. Metab. 80, 31155-3159).

11beta-HSD1 is expressed in many tissues including liver, adipose tissue, vascular smooth muscles, pancreas and brain. Its activity is dependent on NADP(H) and it has a relatively low affinity for its substrate (compared to 11beta-HSD2). 11beta-HSD1 in tissue homogenates and when purified is bidirectional, exhibiting both 11beta-dehydrogenase and 11beta-reductase reactions, with greater stability of the dehydrogenase activity (P. M. Stewart and Z. S. Krozowski, Vitam. Horm. 57 (1999), pp. 249-324). However, when the enzyme activity is tested in intact cells, the 11beta-reductase activity predominates, which regenerates active glucocorticoids from inert 11-keto forms. Such glucocorticoid regeneration will increase effective intracellular glucocorticoid levels and thereby amplifying glucocorticoid activity. It is this elevated cellular cortisol concentration that might lead to increased hepatic glucose production, adipocyte differentiation and insulin resistance.

Inhibition of 11beta-HSD1 should not only reduce the typical Syndrome-X/Diabetes associated symptoms, but it should also be safe and without major side effect. Studies with the unspecific inhibitor carbenoxolone highlight the importance of developing specific 11beta-HSD1 inhibitors. The inhibition of the 11beta-HSD2 enzyme is badly tolerated and results in increased blood pressure. In contrast inhibition of 11beta-HSD1 should be well tolerated since 11beta-HSD1 knockout mice were found to be healthy and to resist hyperglycemia provoked by obesity or stress (Kotelevtsev Y. et al., Proc Natl Acad Sci USA. 1997 Dec. 23; 94(26):14924-9). Similar upon starvation these mice had attenuated activation of key hepatic enzymes that are involved in gluconeogenesis. In addition, these mice had improved lipid and lipoprotein profiles suggesting that inhibition of HSD1 might be highly efficacious and safe. Recent reports indicate that 11beta-HSD1 inhibitors might also be beneficial to reduce high blood pressure (Masuzaki H. et al., J Clin Invest. 2003 July; 112(1): 83-90; Rauz S. et al., QJM. 2003 July; 96(7):481-90), to improve cognition (Sandeep T C. et al., Proc Natl Acad Sci USA. 2004 Apr. 27; 101 (17):6734-9) or to improve Alzheimer associated deficits. Taken together 11beta-HSD1 inhibition might be a safe and efficacious approach to treat symptoms of diabetes, obesity and other diseases.

SUMMARY OF THE INVENTION

In an embodiment of the present invention, provided is a compound of formula (I):

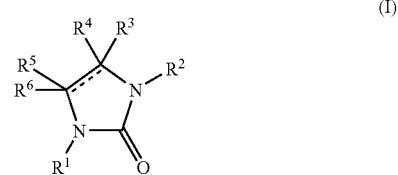

wherein
R¹ is a) bornyl, norbornyl, adamantyl or adamantyl substituted with one or two substituents independently selected from hydroxy, alkoxy, halogen, alkyl, hydroxyalkyl, amino, aminocarbonyl, alkoxycarbonyl, hydroxycarbonyl, alkylcarbonylamino, alkyl-S(O)₂-amino, haloalkyl-S(O)₂-amino, alkoxycarbonylamino-S(O)₂-amino, amino-S(O)₂-amino, hydroxyalkylcarbonylamino, aminocarbonylamino and haloalkoxy;
b) trifluoromethylphenyl, methoxyphenyl, haloalkoxyphenyl or difluorophenyl, wherein trifluoromethylphenyl, haloalkoxyphenyl and difluorophenyl are optionally substituted with one or two substituents independently selected from alkyl, halogen, haloalkyl, alkoxy, hydroxy and haloalkoxy;
c) trifluoromethylphenylalkyl or trifluoromethylphenylalkyl substituted with one or two substituents independently selected from alkyl, halogen, haloalkyl, alkoxy, hydroxy and haloalkoxy;
d) phenylcycloalkyl or phenylcycloalkyl substituted with one to three substituents independently selected from alkyl, halogen, haloalkyl, alkoxy, hydroxy and haloalkoxy;
e) cyanophenyl or cyanophenyl substituted with halogen; or
f) dihalophenyl, aminocarbonylphenyl or hydroxyphenyl, wherein aminocarbonylphenyl and hydroxyphenyl are optionally substituted with one or two substituents independently selected from alkyl, halogen, haloalkyl, alkoxy and haloalkoxy;
R² is hydrogen, alkyl, alkenyl, haloalkyl, pyridinylalkyl, cycloalkyl, cycloalkylalkyl or phenylalkyl or R² is pyridinylalkyl or phenylalkyl which both are substituted with one to three substituents independently selected from alkyl, hydroxy, alkoxy, halogen, haloalkyl and haloalkoxy;
one of R³ and R⁴ is hydrogen, alkyl, cycloalkyl, haloalkyl or absent and the other one is
a) hydrogen, alkyl, pyridinyl, cycloalkyl, cycloalkylalkyl or haloalkyl;
b) phenyl or phenyl substituted with one to three substituents independently selected from fluoro, chloro, bromo, haloalkyl, alkoxy, hydroxy, haloalkyl and haloalkoxy;
c) phenylalkyl or pyridinylalkyl, wherein phenylalkyl and pyridinylalkyl are optionally substituted with one to three substituents independently selected from alkyl, halogen, haloalkyl and hydroxy;
d) oxetane or oxetane substituted with alkyl;
e) naphthyl or tetrahydronapthyl;
f) phenylalkoxyalkyl or phenylalkoxyalkyl substituted with one to three substituents independently selected from alkyl and halogen;
g) hydroxyalkyl; or
h) pyridinyloxyalkyl or pyridinyloxyalkyl substituted with cyano;
or R³ and R⁴ together with the carbon atom to which they are attached form a cycloalkane, piperidine, tetrahydropyrane, tetrahydrothiopyrane, pyrrolidine, tetrahydrofurane, indan or oxetane, wherein cycloalkyl, piperidine, tetrahydropyrane, tetrahydrothiopyrane, pyrrolidine, tetrahydrofurane, indan and oxetane are optionally substituted with one to three substituents independently selected from alkyl, aryl and arylalkyl;
one of R⁵ and R⁶ is hydrogen, isopropyl, isobutyl, cycloalkyl or haloalkyl and the other one is hydrogen or absent;
and pharmaceutically acceptable salts and esters thereof with the proviso that 1,3-dihydro-4-phenyl-1-(3-(trifluoromethyl)phenyl)-2H-imidazol-2-one is excluded and in case one of R³ and R⁴ is methyl, ethyl, n-propyl or n-butyl and the other one is hydrogen or absent then R² is not hydrogen or methyl.

In another embodiment of the present invention, provided is a process for the preparation of a compound according to formula (I):

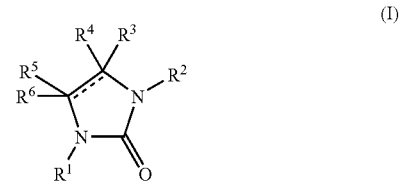

comprising one of the following reactions, wherein R¹ to R⁶ are defined as defined above:

a) reaction of a compound according to formula

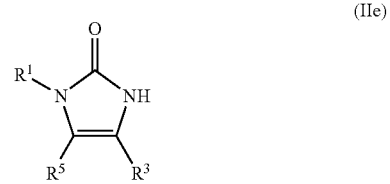

in the presence of R²—X, wherein X is halide or sulfonic acid in order to obtain a compound of formula

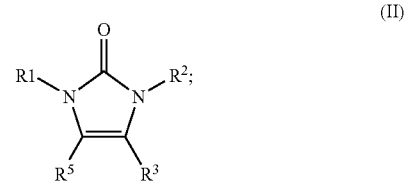

b) reaction of a compound according to formula

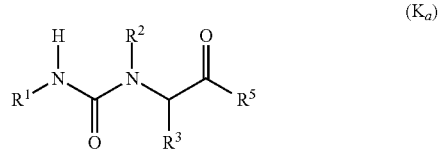

in the presence of an acid in order to obtain a compound of formula

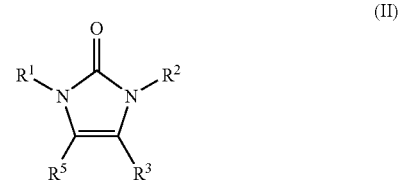

c) reaction of a compound according to formula

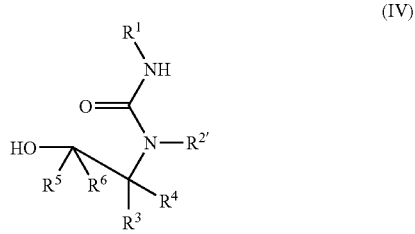

(IV)

in the presence of a base in order to obtain a compound of formula

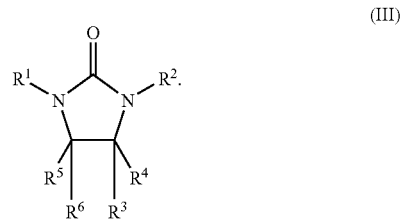

(III)

In a further embodiment of the present invention, provided is a pharmaceutical composition, comprising a therapeutically effective amount of a compound according to formula (I) and a therapeutically inert carrier.

DETAILED DESCRIPTION

The compounds of formula I and their pharmaceutically acceptable salts and esters are novel and have valuable pharmacological properties. In particular they are 11b-HSD1 inhibitors (T2D) and they display selectivity against the related 11beta-HSD2 enzyme. Therefore the compounds which are specific 11beta-HSD1 inhibitors (T2D) represent an approach to e.g. lower blood glucose levels and normalize lipid parameters in Type 2 diabetic patients by modulating the local concentration of the active glucocorticoid cortisol in target tissue (liver, adipose tissue).

The compounds of the present invention can be used in the prophylaxis and/or treatment of metabolic disorders, obesity, dyslipidemiae, hypertension and/or diabetes, particularly diabetes Type II.

The compounds of this invention can further be used in the prophylaxis and/or treatment of high ocular eye pressure, cognition, Alzheimer and/or neurodegeneration.

Further, the compounds of this invention can be used for promoting wound healing, particularly by topical application. Moreover, the compounds of the present invention can be used to improve cognitive impairment, particularly impairments developed with age, and improvement of memory.

Further, the compounds of this invention can be used in the prophylaxis and/or treatment of atherosclerosis.

Embodiments of the present invention are the compounds of formula I and their aforementioned salts and esters per se and their use as therapeutically active substances, a process for the manufacture of the said compounds, intermediates, pharmaceutical compositions, medicaments containing the said compounds, their pharmaceutically acceptable salts and esters, the use of the said compounds, esters and salts for the prophylaxis and/or therapy of illnesses, especially in the treatment or prophylaxis of eating disorders, obesity, dyslipidemiae, hypertension and/or diabetes, particularly diabetes Type II, and the use of the said compounds, salts and esters for the production of medicaments for the treatment or prophylaxis of metabolic disorders, obesity, dyslipidemiae, hypertension and/or diabetes, particularly diabetes Type II.

The compounds of the present invention can further be combined with PPAR (alpha, gamma, delta) agonists, DHEA (dehydroepiandrosterone), DPPIV inhibitors, insulin and/or lipase inhibitors, particularly orlistat.

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

In the present description the term "alkenyl", alone or in combination, signifies a straight-chain or branched-chain alkyl group with 2 to 8 carbon atoms, preferably a straight or branched-chain alkyl group with 2 to 6 carbon atoms and particularly preferred a straight or branched-chain alkyl group with 2 to 4 carbon atoms, wherein one carbon carbon single bond is replaced by a carbon carbon double bond. Examples of straight-chain and branched $C_2$-$C_8$ alkyl groups are ethenyl, allyl, butenyl and preferably allyl.

The term "cycloalkyl", alone or in combination, signifies a cycloalkyl ring with 3 to 8 carbon atoms and preferably a cycloalkyl ring with 3 to 6 carbon atoms. Examples of $C_3$-$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec. butoxy and tert.butoxy, preferably methoxy and ethoxy and most preferred methoxy.

The term "haloalkyl", alone or in combination, signifies an alkyl group as previously defined, wherein one to five hydrogen atoms are substituted by halogen, preferably fluoro. Preferred examples are pentafluoroethyl and particularly trifluoromethyl.

The term "haloalkoxy", alone or in combination, signifies an alkoxy group as previously defined, wherein one to five hydrogen atoms are substituted by halogen, preferably fluoro. Preferred examples are pentafluoroethoxy and particularly trifluoromethoxy and trifluoroethoxy.

The term "hydroxyalkyl", alone or in combination, signifies an alkyl group as defined before, wherein one or more hydrogen atoms, preferably one hydrogen atom is replaced by a hydroxy group. Examples of hydroxyalkyl are hydroxymethyl and hydroxyethyl.

The term "aryl", alone or in combination, signifies a phenyl or naphthyl group, preferably a phenyl group which optionally carries one or more substituents, preferably one to three, each independently selected from halogen, trifluoromethyl, trifluoromethoxy, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, alkyl-$SO_2$—, amino-$SO_2$—, cycloalkyl and the like. Examples are phenyl or naphthyl, particularly phenyl optionally substituted with one to three, preferably one or two substituents independently selected from alkyl, halogen, alkoxy, trifluoromethoxy, nitro and trifluoromethyl.

The term "dihalophenyl" alone or in combination, signifies a phenyl group wherein two hydrogen atoms are replaced by halogen. Examples are dichlorophenyl and chlorofluorophenyl. Particular preferred are 2,5-dichlorophenyl and 2-chloro-5-fluorophenyl.

The term "aryloxy", alone or in combination, signifies a aryl-O— group in which the term "aryl" has the previously given significance.

The term "heterocyclyl", alone or in combination signifies a saturated, partially unsaturated or aromatic 5- to 10-membered heterocycle which contains one or more hetero atoms selected from nitrogen, oxygen and sulphur. If desired, it can be substituted on one or more carbon atoms e.g. by halogen, alkyl, alkoxy, oxo etc. and/or on a secondary nitrogen atom (i.e. —NH—) by alkyl, cycloalkyl, aralkoxycarbonyl, alkanoyl, phenyl or phenylalkyl or on a tertiary nitrogen atom (i.e. =N—) by oxido, with halogen, alkyl, cycloalkyl and alkoxy being preferred. Examples of such heterocyclyl groups are pyrrolidinyl, piperidinyl, piperazinyl, morpholinyl, thiomorpholinyl, pyrazoyl, imidazoyl (e.g. imidazol-4-yl and 1-benzyloxycarbonyl-imidazol-4-yl), pyrazoyl, pyridyl, pyrazinyl, pyrimidinyl, hexahydro-pyrimidinyl, furyl, thienyl, thiazolyl, oxazolyl, indolyl (e.g. 2-indolyl), quinolyl (e.g. 2-quinolyl, 3-quinolyl and 1-oxido-2-quinolyl), isoquinolyl (e.g. 1-isoquinolyl and 3-isoquinolyl), tetrahydroquinolyl (e.g. 1,2,3,4-tetrahydro-2-quinolyl), 1,2,3,4-tetrahydroisoquinolyl (e.g. 1,2,3,4-tetrahydro-1-oxo-isoquinolyl) and quinoxalinyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —NH$_2$, methylamino, ethylamino, dimethylamino, diethylamino, methyl-ethylamino, pyrrolidin-1-yl or piperidino etc., preferably primary amino, dimethylamino and diethylamino and particularly dimethylamino.

The term "halogen", alone or in combination, signifies fluorine, chlorine, bromine or iodine and preferably fluorine, chlorine or bromine.

The term "carbonyl", alone or in combination, signifies the —C(O)— group.

The term "aralkyl", alone or in combination, signifies the aryl-alkyl group, wherein the terms "aryl" and "alkyl" are as previously defined.

The term "hydroxy", alone or in combination, signifies the —OH group.

The term "oxy", alone or in combination, signifies the —O— group.

The term "nitro", alone or in combination signifies the —NO$_2$ group.

The term "cyano", alone or in combination signifies the group —CN.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Pharmaceutically acceptable esters" means that compounds of general formula (I) may be derivatized at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The compounds of formula I can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

The term "asymmetric carbon atom" (C*) means a carbon atom with four different substituents. According to the Cahn-Ingold-Prelog Convention the asymmetric carbon atom can be of the "R" or "S" configuration.

Preferred are the compounds of formula I and pharmaceutically acceptable salts thereof, particularly the compounds of formula I.

The dotted line in formula I (marked as *) represents a carbon carbon single or a carbon carbon double bond

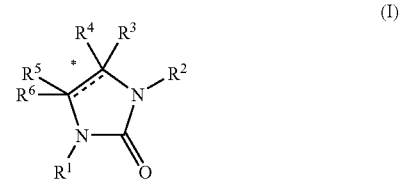

(I)

and, wherein $R^1$ to $R^6$ are defined as before. Accordingly, compounds of formula (I) are of one of the following formulae (II) and (III)

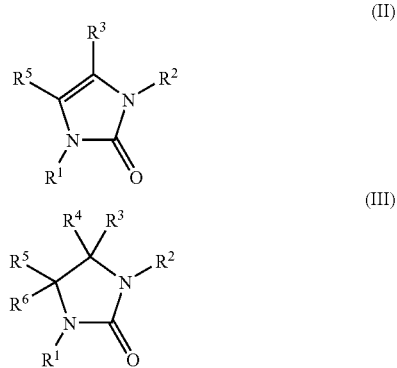

wherein R¹ to R⁶ are defined as before.

Preferred compounds of formula I are those which are of formula II. Particularly preferred are those compounds of formula I which are of formula III.

Further preferred are compounds of formula I, wherein R¹ is a) bornyl, norbornyl, adamantyl or adamantyl substituted with one or two substituents independently selected from hydroxy, alkoxy, halogen and alkyl;

b) trifluoromethylphenyl, methoxyphenyl, haloalkoxyphenyl or difluorophenyl, wherein trifluoromethylphenyl, haloalkoxyphenyl and difluorophenyl are optionally substituted with one or two substituents independently selected from alkyl, halogen, haloalkyl, alkoxy, hydroxy and haloalkoxy;

c) trifluoromethylphenylalkyl or trifluoromethylphenylalkyl substituted with one or two substituents independently selected from alkyl, halogen, haloalkyl, alkoxy, hydroxy and haloalkoxy; or d) phenylcycloalkyl or phenylcycloalkyl substituted with one to three substituents independently selected from alkyl, halogen, haloalkyl, alkoxy, hydroxy and haloalkoxy.

Another preferred aspect of the invention are compounds of formula I, wherein R² is hydrogen, alkyl, haloalkyl, pyridinylalkyl, cycloalkyl, cycloalkylalkyl or phenylalkyl or R² is pyridinylalkyl or phenylalkyl which both are substituted with one to three substituents independently selected from alkyl, hydroxy, alkoxy, halogen and haloalkyl.

Further preferred are those compounds of formula I, wherein one of R³ and R⁴ is hydrogen, alkyl, cycloalkyl, haloalkyl or absent and the other one is a) hydrogen, alkyl, pyridinyl, cycloalkyl, cycloalkylalkyl or haloalkyl;

b) phenyl or phenyl substituted with one to three substituents independently selected from fluoro, haloalkyl and hydroxy;

c) phenylalkyl or pyridinylalkyl, wherein phenylalkyl and pyridinylalkyl are optionally substituted with one to three substituents independently selected from alkyl, halogen, haloalkyl and hydroxy; or d) oxetane or oxetane substituted with alkyl;

or R³ and R⁴ together with the carbon atom to which they are attached form a cycloalkane, piperidine, tetrahydropyrane, tetrahydrothiopyrane, pyrrolidine, tetrahydrofurane, indan or oxetane, wherein cycloalkyl, piperidine, tetrahydropyrane, tetrahydrothiopyrane, pyrrolidine, tetrahydrofurane, indan and oxetane are optionally substituted with one to three substituents independently selected from alkyl and arylalkyl.

Preferred are compounds of formula I, wherein

R¹ is a) bornyl, norbornyl, adamantyl or adamantyl substituted with one or two substituents independently selected from hydroxy, alkoxy, halogen and alkyl;

b) trifluoromethylphenyl, methoxyphenyl, haloalkoxyphenyl or difluorophenyl, wherein trifluoromethylphenyl, haloalkoxyphenyl and difluorophenyl are optionally substituted with one or two substituents independently selected from alkyl, halogen, haloalkyl, alkoxy, hydroxy and haloalkoxy;

c) trifluoromethylphenylalkyl or trifluoromethylphenylalkyl substituted with one or two substituents independently selected from alkyl, halogen, haloalkyl, alkoxy, hydroxy and haloalkoxy; or d) phenylcycloalkyl or phenylcycloalkyl substituted with one to three substituents independently selected from alkyl, halogen, haloalkyl, alkoxy, hydroxy and haloalkoxy;

R² is hydrogen, alkyl, haloalkyl, pyridinylalkyl, cycloalkyl, cycloalkylalkyl or phenylalkyl or R² is pyridinylalkyl or phenylalkyl which both are substituted with one to three substituents independently selected from alkyl, hydroxy, alkoxy, halogen and haloalkyl;

one of R³ and R⁴ is hydrogen, alkyl, cycloalkyl, haloalkyl or absent and the other one is a) hydrogen, alkyl, pyridinyl, cycloalkyl, cycloalkylalkyl or haloalkyl;

b) phenyl or phenyl substituted with one to three substituents independently selected from fluoro, haloalkyl and hydroxy;

c) phenylalkyl or pyridinylalkyl, wherein phenylalkyl and pyridinylalkyl are optionally substituted with one to three substituents independently selected from alkyl, halogen, haloalkyl and hydroxy; or d) oxetane or oxetane substituted with alkyl;

or R³ and R⁴ together with the carbon atom to which they are attached form a cycloalkane, piperidine, tetrahydropyrane, tetrahydrothiopyrane, pyrrolidine, tetrahydrofurane, indan or oxetane, wherein cycloalkyl, piperidine, tetrahydropyrane, tetrahydrothiopyrane, pyrrolidine, tetrahydrofurane, indan and oxetane are optionally substituted with one to three substituents independently selected from alkyl and arylalkyl;

one of R⁵ and R⁶ is hydrogen, isopropyl, isobutyl, cycloalkyl or haloalkyl and the other one is hydrogen or absent;

and pharmaceutically acceptable salts and esters thereof with the proviso that 1,3-dihydro-4-phenyl-1-(3-(trifluoromethyl) phenyl)-2H-imidazol-2-one is excluded and in case one of R³ and R⁴ is methyl, ethyl, n-propyl or n-butyl and the other one is hydrogen or absent then R² is not hydrogen or methyl.

Further preferred are those compounds of formula I, wherein R¹ is adamantyl or hydroxyadamantyl.

Further preferred compounds according to formula I are those, wherein R¹ is (Z)-5-hydroxy-adamantan-2-yl. Particularly preferred are those compounds of formula I, wherein R¹ is (E)-5-hydroxy-adamantan-2-yl.

Also preferred are compounds of formula I, wherein R¹ is trifluoromethylphenyl.

Another preferred aspect of the present invention are compounds according to formula I, wherein R² is hydrogen.

Preferred are further those compounds of formula I, wherein R² is methyl, ethyl or cyclopropyl.

Another preferred aspect are the compounds according to formula I, wherein one of R³ and R⁴ is hydrogen or methyl and the other one is isopropyl, cyclopropyl or cyclopropylmethyl.

Further preferred are compounds of formula I, wherein R³ and R⁴ are methyl or R³ and R⁴ together with the carbon atom to which they are attached form cyclopentane or indan.

Further preferred are compounds of formula I wherein one of $R^3$ and $R^4$ is methyl and the other one is phenyl substituted with one or two halogens independently selected from fluoro and chloro.

Also preferred are compounds according to formula I, wherein $R^3$ and $R^4$ together with the carbon atom to which they are attached form cyclohexane or cycloheptane.

Preferred are those compounds according to formula I, wherein one of $R^5$ and $R^6$ is hydrogen and the other one is hydrogen or absent.

Examples of preferred compounds of formula (I) are:
1) 1-Adamantan-2-yl-3-benzyl-1,3-dihydro-imidazol-2-one;
2) 1-Adamantan-2-yl-3-pyridin-2-ylmethyl-1,3-dihydro-imidazol-2-one;
3) 1-Adamantan-2-yl-3-isopropyl-4-phenyl-1,3-dihydro-imidazol-2-one;
4) 1-Adamantan-2-yl-3-cyclopropyl-4-phenyl-1,3-dihydro-imidazol-2-one;
5) 1-Adamantan-2-yl-3-cyclopropyl-4-(3-fluoro-phenyl)-1,3-dihydro-imidazol-2-one;
6) 1-Adamantan-2-yl-3-cyclopropyl-4-pyridin-2-yl-1,3-dihydro-imidazol-2-one;
7) 1-Adamantan-2-yl-4-tert-butyl-1,3-dihydro-imidazol-2-one;
8) 1-Adamantan-2-yl-4-isopropyl-1,3-dihydro-imidazol-2-one;
9) 1-Adamantan-2-yl-4-phenyl-1,3-dihydro-imidazol-2-one;
10) 1-Adamantan-2-yl-4-isobutyl-1,3-dihydro-imidazol-2-one;
11) 1-Adamantan-2-yl-4-(3-fluoro-benzyl)-1,3-dihydro-imidazol-2-one;
12) 1-Adamantan-2-yl-4-[(S)-sec-butyl]-1,3-dihydro-imidazol-2-one;
13) 1-Adamantan-2-yl-4-(2,2-dimethyl-propyl)-1,3-dihydro-imidazol-2-one;
14) 1-Adamantan-2-yl-4-cyclohexyl-1,3-dihydro-imidazol-2-one;
15) 1-Adamantan-2-yl-4-cyclopropyl-1,3-dihydro-imidazol-2-one;
16) 1-Adamantan-2-yl-4-(2,2,2-trifluoro-ethyl)-1,3-dihydro-imidazol-2-one;
17) 1-Adamantan-2-yl-4-cyclopropylmethyl-1,3-dihydro-imidazol-2-one;
18) 4-Isobutyl-1-(2-trifluoromethyl-phenyl)-1,3-dihydro-imidazol-2-one;
19) 4-Isopropyl-1-(2-trifluoromethyl-phenyl)-1,3-dihydro-imidazol-2-one;
20) 1-Adamantan-1-yl-4-isobutyl-1,3-dihydro-imidazol-2-one;
21) 1-Adamantan-1-yl-4-isopropyl-1,3-dihydro-imidazol-2-one;
22) 1-(1R,2S,4S/1S,2R,4R)-Bicyclo[2.2.1]hept-2-yl-4-tert-butyl-1,3-dihydro-imidazol-2-one;
23) 1-Adamantan-2-yl-3-cyclopropylmethyl-4-isopropyl-1,3-dihydro-imidazol-2-one;
24) 1-Adamantan-2-yl-4-isopropyl-3-pyridin-2-ylmethyl-1,3-dihydro-imidazol-2-one;
25) 1-Adamantan-2-yl-3-cyclopropyl-4-isopropyl-1,3-dihydro-imidazol-2-one;
26) 1-Adamantan-2-yl-3-cyclobutylmethyl-4-isopropyl-1,3-dihydro-imidazol-2-one;
27) 1-Adamantan-2-yl-4-cyclopropyl-3-cyclopropylmethyl-1,3-dihydro-imidazol-2-one;
28) 3-Cyclopropyl-1-(5-fluoro-2-trifluoromethyl-benzyl)-4-methyl-1,3-dihydro-imidazol-2-one;
29) 3-Cyclopropyl-4-methyl-1-(2-trifluoromethyl-benzyl)-1,3-dihydro-imidazol-2-one;
30) 1-[1-(4-Chloro-phenyl)-cyclopropyl]-4-isopropyl-1,3-dihydro-imidazol-2-one;
31) 1-Adamantan-2-yl-4-benzyl-5-isopropyl-1,3-dihydro-imidazol-2-one;
32) 1-Adamantan-2-yl-3-methyl-4-(2,2,2-trifluoro-ethyl)-1,3-dihydro-imidazol-2-one;
33) 1-Adamantan-2-yl-3-cyclopropylmethyl-4-(2,2,2-trifluoro-ethyl)-1,3-dihydro-imidazol-2-one;
34) 1-Adamantan-2-yl-4-cyclopropyl-3-methyl-1,3-dihydro-imidazol-2-one;
35) 3-Cyclopropylmethyl-4-isopropyl-1-(2-trifluoromethyl-phenyl)-1,3-dihydro-imidazol-2-one;
36) 3-Cyclopropylmethyl-4-isobutyl-1-(2-trifluoromethyl-phenyl)-1,3-dihydro-imidazol-2-one;
37) 4-Isobutyl-5-(2,2,2-trifluoro-ethyl)-1-(2-trifluoromethyl-phenyl)-1,3-dihydro-imidazol-2-one;
38) 4-Isobutyl-3-methyl-1-(2-trifluoromethyl-phenyl)-1,3-dihydro-imidazol-2-one;
39) 3-Cyclobutylmethyl-4-isobutyl-1-(2-trifluoromethyl-phenyl)-1,3-dihydro-imidazol-2-one;
40) 1-[(Z)-5-Hydroxy-adamantan-2-yl]-4-isobutyl-1,3-dihydro-imidazol-2-one;
41) 1-[(E)-5-Hydroxy-adamantan-2-yl]-4-isobutyl-1,3-dihydro-imidazol-2-one;
42) 4-Isobutyl-1-(2-methoxy-phenyl)-1,3-dihydro-imidazol-2-one;
43) 3-Cyclopropylmethyl-4-isobutyl-1-(2-methoxy-phenyl)-1,3-dihydro-imidazol-2-one;
44) 4-Isobutyl-1-(2-trifluoromethoxy-phenyl)-1,3-dihydro-imidazol-2-one;
45) 3-Cyclopropylmethyl-4-isobutyl-1-(2-trifluoromethoxy-phenyl)-1,3-dihydro-imidazol-2-one;
46) 1-(2,4-Difluoro-phenyl)-4-isobutyl-1,3-dihydro-imidazol-2-one;
47) 4-Isobutyl-1-(2-methyl-6-trifluoromethyl-phenyl)-1,3-dihydro-imidazol-2-one;
48) 1-Adamantan-2-yl-3-cyclopropyl-4-isobutyl-1,3-dihydro-imidazol-2-one;
49) 3-Cyclopropyl-4-isopropyl-1-(2-trifluoromethyl-phenyl)-1,3-dihydro-imidazol-2-one;
50) 4-Isobutyl-1-(2-trifluoromethyl-phenyl)-imidazolidin-2-one;
51) 1-Adamantan-2-yl-4-isopropyl-imidazolidin-2-one;
52) (R)-1-Adamantan-2-yl-4-isopropyl-imidazolidin-2-one;
53) (S)-1-Adamantan-2-yl-4-isopropyl-imidazolidin-2-one;
54) (S)-1-Adamantan-2-yl-4-isopropyl-3-methyl-imidazolidin-2-one;
55) (R)-1-Adamantan-2-yl-4-isopropyl-3-methyl-imidazolidin-2-one;
56) 1-Adamantan-2-yl-3-isobutyl-4-isopropyl-imidazolidin-2-one;
57) 1-Adamantan-2-yl-3-cyclopropylmethyl-4-isopropyl-imidazolidin-2-one;
58) 1-Adamantan-2-yl-4-isobutyl-imidazolidin-2-one;
59) 1-Adamantan-2-yl-4-cyclopropylmethyl-imidazolidin-2-one;
60) 1-Adamantan-2-yl-4,4-dimethyl-imidazolidin-2-one;
61) 1-[(E/Z)-5-Hydroxy-adamantan-2-yl]-4,4-dimethyl-imidazolidin-2-one;
62) 3-Adamantan-2-yl-1,3-diaza-spiro[4.4]nonan-2-one;
63) 3-Cyclopropyl-4-isopropyl-1-(2-trifluoromethyl-phenyl)-imidazolidin-2-one;
64) 3,4-Dicyclopropyl-1-(2-trifluoromethyl-phenyl)-imidazolidin-2-one;
65) 1-Adamantan-2-yl-4-cyclopropyl-4-methyl-imidazolidin-2-one;

66) 1-Adamantan-2-yl-3,4-dicyclopropyl-imidazolidin-2-one;
67) 3,4-Dicyclopropyl-1-[(Z)-5-hydroxy-adamantan-2-yl]-imidazolidin-2-one;
68) 3,4-Dicyclopropyl-1-[(E)-5-hydroxy-adamantan-2-yl]-imidazolidin-2-one;
69) 4-Cyclopropyl-1-[(E)-5-hydroxy-adamantan-2-yl]-4-methyl-imidazolidin-2-one;
70) 4-Cyclopropyl-1-[(Z)-5-hydroxy-adamantan-2-yl]-4-methyl-imidazolidin-2-one;
71) 4-Cyclopropyl-1-[(E)-5-hydroxy-adamantan-2-yl]-3,4-dimethyl-imidazolidin-2-one;
72) 1-Adamantan-2-yl-4-isopropyl-4-methyl-imidazolidin-2-one;
73) 1-[(Z)-5-Hydroxy-adamantan-2-yl]-4-isopropyl-3-methyl-imidazolidin-2-one;
74) 1-[(E)-5-Hydroxy-adamantan-2-yl]-4-isopropyl-3-methyl-imidazolidin-2-one;
75) 1-Adamantan-2-yl-3,4-dicyclopropyl-4-methyl-imidazolidin-2-one;
76) 3-Cyclopropyl-1-[(Z)-5-hydroxy-adamantan-2-yl]-4,4-dimethyl-imidazolidin-2-one;
77) 3-Cyclopropyl-1-[(E)-5-hydroxy-adamantan-2-yl]-4,4-dimethyl-imidazolidin-2-one;
78) 1-Adamantan-2-yl-3-cyclopropyl-4,4-dimethyl-imidazolidin-2-one;
79) 3,4-Dicyclopropyl-1-[(Z)-5-hydroxy-adamantan-2-yl]-4-methyl-imidazolidin-2-one;
80) 3,4-Dicyclopropyl-1-[(E)-5-hydroxy-adamantan-2-yl]-4-methyl-imidazolidin-2-one;
81) 3-[(Z)-5-Hydroxy-adamantan-2-yl]-1,3-diaza-spiro[4,4]nonan-2-one;
82) 3-[(E)-5-Hydroxy-adamantan-2-yl]-1,3-diaza-spiro[4,4]nonan-2-one;
83) 4,4-Dicyclopropyl-1-[(Z)-5-hydroxy-adamantan-2-yl]-imidazolidin-2-one;
84) 4,4-Dicyclopropyl-1-[(E)-5-hydroxy-adamantan-2-yl]-imidazolidin-2-one;
85) 3-[(E)-5-Hydroxy-adamantan-2-yl]-1-methyl-1,3-diaza-spiro[4,4]nonan-2-one;
86) 4-Cyclopropyl-1-[(F)-5-methoxy-adamantan-2-yl]-3,4-dimethyl-imidazolidin-2-one;
87) 3-Ethyl-1-[(E)-5-hydroxy-adamantan-2-yl]-4,4-dimethyl-imidazolidin-2-one;
88) 3-(2-Fluoro-ethyl)-1-[(E)-5-hydroxy-adamantan-2-yl]-4,4-dimethyl-imidazolidin-2-one;
89) 1-[(F)-5-Hydroxy-adamantan-2-yl]-3,4,4-trimethyl-imidazolidin-2-one;
90) 1-[(Z)-5-Hydroxy-adamantan-2-yl]-4-isopropyl-4-methyl-imidazolidin-2-one;
91) 1-[(E)-5-Hydroxy-adamantan-2-yl]-4-isopropyl-4-methyl-imidazolidin-2-one;
92) 1-[(E)-5-Hydroxy-adamantan-2-yl]-4-isopropyl-3,4-dimethyl-imidazolidin-2-one;
93) 3-Ethyl-1-[(E)-5-hydroxy-adamantan-2-yl]-4-isopropyl-4-methyl-imidazolidin-2-one;
94) (R or S)-4-Cyclopropyl-3-ethyl-1-[(E)-5-hydroxy-adamantan-2-yl]-4-methyl-imidazolidin-2-one;
95) 1-Cyclopropyl-3-[(Z)-5-hydroxy-adamantan-2-yl]-1,3-diaza-spiro[4.4]nonan-2-one;
96) 1-Cyclopropyl-3-[(E)-5-hydroxy-adamantan-2-yl]-1,3-diaza-spiro[4.4]nonan-2-one;
97) 7-Benzyl-3-[(Z)-5-hydroxy-adamantan-2-yl]-1,3,7-triaza-spiro[4.5]decan-2-one;
98) 7-Benzyl-3-[(E)-5-hydroxy-adamantan-2-yl]-1,3,7-triaza-spiro[4.5]decan-2-one;
99) 7-Benzyl-3-[(E)-5-hydroxy-adamantan-2-yl]-1-methyl-1,3,7-triaza-spiro[4.5]decan-2-one;
100) 1',3'-Dihydro-1-[(Z)-5-hydroxy-adamantan-2-yl]-spiro[imidazolidine-4,2'-[2H]indene]-2-one;
101) 1',3'-Dihydro-1-[(E)-5-hydroxy-adamantan-2-yl]-spiro[imidazolidine-4,2'-[2H]indene]-2-one; and
102) 1',3'-Dihydro-1-[(E)-5-hydroxy-adamantan-2-yl]-3-methyl-spiro[imidazolidine-4,2'-[2H]indene]-2-one.

Examples of particularly preferred compounds of formula (I) are:
(S)-1-Adamantan-2-yl-4-isopropyl-imidazolidin-2-one;
(R)-1-Adamantan-2-yl-4-isopropyl-3-methyl-imidazolidin-2-one;
1-Adamantan-2-yl-4-cyclopropylmethyl-imidazolidin-2-one;
1-Adamantan-2-yl-4,4-dimethyl-imidazolidin-2-one;
3-Adamantan-2-yl-1,3-diaza-spiro[4.4]nonan-2-one;
3-Cyclopropyl-4-isopropyl-1-(2-trifluoromethyl-phenyl)-imidazolidin-2-one;
3,4-Dicyclopropyl-1-(2-trifluoromethyl-phenyl)-imidazolidin-2-one;
1-Adamantan-2-yl-4-cyclopropyl-4-methyl-imidazolidin-2-one;
1-Adamantan-2-yl-3,4-dicyclopropyl-imidazolidin-2-one;
3,4-Dicyclopropyl-1-[(E)-5-hydroxy-adamantan-2-yl]-imidazolidin-2-one;
4-Cyclopropyl-1-[(E)-5-hydroxy-adamantan-2-yl]-4-methyl-imidazolidin-2-one;
4-Cyclopropyl-1-[(E)-5-hydroxy-adamantan-2-yl]-3,4-dimethyl-imidazolidin-2-one;
1-Adamantan-2-yl-4-isopropyl-4-methyl-imidazolidin-2-one;
1-[(E)-5-Hydroxy-adamantan-2-yl]-4-isopropyl-3-methyl-imidazolidin-2-one;
1-Adamantan-2-yl-3,4-dicyclopropyl-4-methyl-imidazolidin-2-one;
3-Cyclopropyl-1-[(E)-5-hydroxy-adamantan-2-yl]-4,4-dimethyl-imidazolidin-2-one;
3,4-Dicyclopropyl-1-[(E)-5-hydroxy-adamantan-2-yl]-4-methyl-imidazolidin-2-one;
3-[(E)-5-Hydroxy-adamantan-2-yl]-1,3-diaza-spiro[4.4]nonan-2-one;
3-[(E)-5-Hydroxy-adamantan-2-yl]-1-methyl-1,3-diaza-spiro[4.4]nonan-2-one;
3-Ethyl-1-[(E)-5-hydroxy-adamantan-2-yl]-4,4-dimethyl-imidazolidin-2-one;
1-[(E)-5-Hydroxy-adamantan-2-yl]-3,4,4-trimethyl-imidazolidin-2-one;
1-[(E)-5-Hydroxy-adamantan-2-yl]-4-isopropyl-3,4-dimethyl-imidazolidin-2-one;
3-Ethyl-1-[(E)-5-hydroxy-adamantan-2-yl]-4-isopropyl-4-methyl-imidazolidin-2-one;
(R or S)-4-Cyclopropyl-3-ethyl-1-[(E)-5-hydroxy-adamantan-2-yl]-4-methyl-imidazolidin-2-one;
1-Cyclopropyl-3-[(E)-5-hydroxy-adamantan-2-yl]-1,3-diaza-spiro[4.4]nonan-2-one;
7-Benzyl-3-[(E)-5-hydroxy-adamantan-2-yl]-1-methyl-1,3,7-triaza-spiro[4.5]decan-2-one; and
1',3'-Dihydro-1-[(E)-5-hydroxy-adamantan-2-yl]-3-methyl-spiro[imidazolidine-4,2'-[2H]indene]-2-one.

Further examples of preferred compounds of the invention are:
1-[(E)-5-aminoadamantan-2-yl]-1',3'-dihydro-2H-spiro[imidazolidine-4,2'-inden]-2-one;
1-[(Z)-5-aminoadamantan-2-yl]-1',3'-dihydro-2H-spiro[imidazolidine-4,2'-inden]-2-one;

N-[(E)-4-(2-oxo-1',3'-dihydro-1H-spiro[imidazolidine-4,2'-inden]-1-yl)adamantan-1-yl]acetamide;
N-[(Z)-4-(2-oxo-1',3'-dihydro-1H-spiro[imidazolidine-4,2'-inden]-1-yl)adamantan-1-yl]acetamide;
N-[(E)-4-(2-oxo-1',3'-dihydro-1H-spiro[imidazolidine-4,2'-inden]-1-yl)adamantan-1-yl]methanesulfonamide;
N-[(Z)-4-(2-oxo-1',3'-dihydro-1H-spiro[imidazolidine-4,2'-inden]-1-yl)adamantan-1-yl]methanesulfonamide;
1,1,1-trifluoro-N-[(E)-4-(2-oxo-1',3'-dihydro-1H-spiro[imidazolidine-4,2'-inden]-1-yl)adamantan-1-yl]methanesulfonamide;
1,1,1-trifluoro-N-[(Z)-4-(2-oxo-1',3'-dihydro-1H-spiro[imidazolidine-4,2'-inden]-1-yl)adamantan-1-yl]methanesulfonamide;
tert-butyl({[(E)-4-(2-oxo-1',3'-dihydro-1H-spiro[imidazolidine-4,2'-inden]-1-yl)adamantan-1-yl]amino}sulfonyl)carbamate;
tert-butyl({[(Z)-4-(2-oxo-1',3'-dihydro-1H-spiro[imidazolidine-4,2'-inden]-1-yl)adamantan-1-yl]amino}sulfonyl)carbamate;
N-[(E)-4-(2-oxo-1,3'-dihydro-1H-spiro[imidazolidine-4,2'-inden]-1-yl)adamantan-1-yl]sulfamide;
N-[(Z)-4-(2-oxo-1',3'-dihydro-1H-spiro[imidazolidine-4,2'-inden]-1-yl)adamantan-1-yl]sulfamide;
2-hydroxy-N-[(E)-4-(2-oxo-1',3'-dihydro-1H-spiro[imidazolidine-4,2'-inden]-1-yl)adamantan-1-yl]acetamide;
2-hydroxy-N-[(Z)-4-(2-oxo-1',3'-dihydro-1H-spiro[imidazolidine-4,2'-inden]-1-yl)adamantan-1-yl]acetamide;
1-[(E)-4-(2-oxo-1',3'-dihydro-1H-spiro[imidazolidine-4,2'-inden]-1-yl)adamantan-1-yl]urea;
1-[(E)-5-(dimethylamino)adamantan-2-yl]-3-methyl-1',3'-dihydro-2H-spiro[imidazolidine-4,2'-inden]-2-one;
1-[(E)-5-(2,2,2-trifluoroethoxy)adamantan-2-yl]-1',3'-dihydro-2H-spiro[imidazolidine-4,2'-inden]-2-one;
1-[(Z)-5-(2,2,2-trifluoroethoxy)adamantan-2-yl]-1',3'-dihydro-2H-spiro[imidazolidine-4,2'-inden]-2-one;
3-chloro-4-(2-oxo-1',3'-dihydro-1H-spiro[imidazolidine-4,2'-inden]-1-yl)benzonitrile;
3-(5,7-Dihydroxy-adamantan-2-yl)-1,3-diazaspiro[4.4]nonan-2-one;
1',3'-Dihydro-1-[(Z)-5-hydroxy-adamantan-2-yl]-3-methyl-spiro[imidazolidine-4,2'-[2H] indene]-2-one;
1-[(E)-5-aminoadamantan-2-yl]-3-methyl-1',3'-dihydro-2H-spiro[imidazolidine-4,2'-inden]-2-one;
1-[(Z)-5-aminoadamantan-2-yl]-3-methyl-1',3'-dihydro-2H-spiro[imidazolidine-4,2'-inden]-2-one;
N-[(E)-4-(3-methyl-2-oxo-1',3'-dihydro-1H-spiro[imidazolidine-4,2'-inden]-1-yl)adamantan-1-yl]acetamide;
N-[(Z)-4-(3-methyl-2-oxo-1',3'-dihydro-1H-spiro[imidazolidine-4,2'-inden]-1-yl)adamantan-1-yl]acetamide;
N-[(E)-4-(3-methyl-2-oxo-1',3'-dihydro-1H-spiro[imidazolidine-4,2'-inden]-1-yl)adamantan-1-yl]methanesulfonamide;
N-[(Z)-4-(3-methyl-2-oxo-1',3'-dihydro-1H-spiro[imidazolidine-4,2'-inden]-1-yl)adamantan-1-yl]methanesulfonamide;
1,1,1-trifluoro-N-[(E)-4-(3-methyl-2-oxo-1',3'-dihydro-1H-spiro[imidazolidine-4,2'-inden]-1-yl)adamantan-1-yl]methanesulfonamide;
1,1,1-trifluoro-N-[(Z)-4-(3-methyl-2-oxo-1',3'-dihydro-1H-spiro[imidazolidine-4,2'-inden]-1-yl)adamantan-1-yl]methanesulfonamide;
N-[(E)-4-(3-methyl-2-oxo-1',3'-dihydro-1H-spiro[imidazolidine-4,2'-inden]-1-yl)adamantan-1-yl]sulfamide;
N-[(Z)-4-(3-methyl-2-oxo-1',3'-dihydro-1H-spiro[imidazolidine-4,2'-inden]-1-yl)adamantan-1-yl]sulfamide;
2-hydroxy-N-[(E)-4-(3-methyl-2-oxo-1',3'-dihydro-1H-spiro[imidazolidine-4,2'-inden]-1-yl)adamantan-1-yl]acetamide;
2-hydroxy-N-[(Z)-4-(3-methyl-2-oxo-1,3'-dihydro-1H-spiro[imidazolidine-4,2'-inden]-1-yl)adamantan-1-yl]acetamide;
1-[(E)-4-(3-methyl-2-oxo-1',3'-dihydro-1H-spiro[imidazolidine-4,2'-inden]-1-yl)adamantan-1-yl]urea;
1-[(Z)-4-(3-methyl-2-oxo-1',3'-dihydro-1H-spiro[imidazolidine-4,2'-inden]-1-yl)adamantan-1-yl]urea;
Methyl(E/Z)-4-(2-oxo-1',3'-dihydro-1H-spiro[imidazolidine-4,2'-inden]-1-yl)adamantane-1-carboxylate;
(E/Z)-4-(2-oxo-1',3'-dihydro-1H-spiro[imidazolidine-4,2'-inden]-1-yl)adamantane-1-carboxylic acid;
(E/Z)-4-(2-oxo-1',3'-dihydro-1H-spiro[imidazolidine-4,2'-inden]-1-yl)adamantane-1-carboxamide;
1-[5-(E/Z)-(hydroxymethyl)adamantan-2-yl]-1',3'-dihydro-2H-spiro[imidazolidine-4,2'-inden]-2-one;
(E/Z)-4-(2-Oxo-1,3-diaza-spiro[4.4]non-3-yl)-adamantane-1-carboxylic acid methyl ester;
(E/Z)-4-(2-Oxo-1,3-diaza-spiro[4.4]non-3-yl)-adamantane-1-carboxylic acid;
(E/Z)-4-(2-Oxo-1,3-diaza-spiro[4.4]non-3-yl)-adamantane-1-carboxylic acid amide;
3-[(E/Z)-5-Hydroxymethyl-adamantan-2-yl]-1,3-diazaspiro[4.4]nonan-2-one;
(E/Z)-4-(1-Ethyl-2-oxo-1,3-diaza-spiro[4.4]non-3-yl)-adamantane-1-carboxylic acid methyl ester;
(E/Z)-4-(1-Ethyl-2-oxo-1,3-diaza-spiro[4.4]non-3-yl)-adamantane-1-carboxylic acid;
(E/Z)-4-(2-Oxo-1,3-diaza-spiro[4.4]non-3-yl)-adamantane-1-carboxylic acid amide;
3-(3-Chloro-benzyl)-1-((E)-5-hydroxy-adamantan-2-yl)-4,4-dimethyl-imidazolidin-2-one;
1-((E)-5-Hydroxy-adamantan-2-yl)-4,4-dimethyl-3-(3-trifluoromethoxy-benzyl)-imidazolidin-2-one;
(R)-3-(4-Bromo-benzyl)-4-cyclopropyl-1-((E)-5-hydroxy-adamantan-2-yl)-4-methyl-imidazolidin-2-one;
N-[(E)-4-(4-Isopropyl-3-methyl-2-oxo-imidazolidin-1-yl)-adamantan-1-yl]-acetamide;
N-[(Z)-4-(4-Isopropyl-3-methyl-2-oxo-imidazolidin-1-yl)-adamantan-1-yl]-acetamide;
5-Benzyl-7-((E/Z)-5-hydroxy-adamantan-2-yl)-2-oxa-5,7-diaza-spiro[3.4]octan-6-one;
4-(1-Cyclopropyl-2-oxo-1,3-diaza-spiro[4.6]undec-3-yl)-benzamide;
1-Cyclopropyl-3-(4-methoxy-2-trifluoromethyl-phenyl)-1,3-diaza-spiro[4.6]undecan-2-one;
4-(3-Cyclopropyl-4-isopropyl-2-oxo-imidazolidin-1-yl)-benzamide;
4-(1-Cyclopropyl-3-(4-methoxy-phenyl)-1,3-diaza-spiro[4.5]decan-2-one;
4-(1-Cyclopropyl-3-(4-hydroxy-phenyl)-1,3-diaza-spiro[4.5]decan-2-one;
3-(3-Chloro-4-methoxy-phenyl)-1-cyclopropyl-1,3-diaza-spiro[4.5]decan-2-one;
3-(3-Chloro-4-hydroxy-phenyl)-1-cyclopropyl-1,3-diaza-spiro[4.5]decan-2-one;
1-Cyclopropyl-3-(2,4-dimethoxy-phenyl)-1,3-diaza-spiro[4.5]decan-2-one;
1-Cyclopropyl-3-(2-trifluoromethyl-phenyl)-1,3-diaza-spiro[4.5]decan-2-one;
3-Cyclopropyl-1-(2,5-dichloro-phenyl)-4-isopropyl-imidazolidin-2-one;
3-Cyclopropyl-4-isopropyl-1-(4-methoxy-phenyl)-imidazolidin-2-one;

3-Cyclopropyl-4-isopropyl-1-(4-hydroxy-phenyl)-imidazolidin-2-one;
3-Cyclopropyl-1-(3-fluoro-4-methoxy-phenyl)-4-isopropyl-imidazolidin-2-one;
1-Cyclopropyl-3-(4-methoxy-phenyl)-8-phenyl-1,3-diazaspiro[4.5]decan-2-one;
4-Benzyl-3-cyclopropyl-1-(2,5-dichloro-phenyl)-imidazolidin-2-one;
3-Benzyl-1-(2-chloro-5-fluoro-phenyl)-4-isopropyl-imidazolidin-2-one;
1-Allyl-3-(2-chloro-5-fluoro-phenyl)-5-isopropyl-imidazolidine-2-one;
1-Benzyl-3-(2,5-dichloro-phenyl)-5-isopropyl-imidazolidine-2-one;
1-(2,5-Dichloro-phenyl)-3-(4-fluoro-benzyl)-4-isopropyl-imidazolidin-2-one;
1-(4-methoxyphenyl)-3-methyl-1',3'-dihydro-2H-spiro[imidazolidine-4,2'-inden]-2-one;
1-(4-hydroxyphenyl)-3-methyl-1',3'-dihydro-2H-spiro[imidazolidine-4,2'-inden]-2-one;
(E/Z)-4-[4-(3-Chloro-phenyl)-4-methyl-2-oxo-imidazolidin-1-yl]-adamantane-1-carboxylic acid methyl ester;
(E)-4-[4-(3-Chloro-phenyl)-4-methyl-2-oxo-imidazolidin-1-yl]-adamantane-1-carboxylic acid amide;
4-(4-Fluoro-phenyl)-1-((E)-5-hydroxy-adamantan-2-yl)-4-methyl-imidazolidin-2-one;
4-(2-Fluoro-phenyl)-1-((E/Z)-5-hydroxy-adamantan-2-yl)-4-methyl-imidazolidin-2-one;
4-(3-Chloro-phenyl)-1-((E)-5-hydroxy-adamantan-2-yl)-4-methyl-imidazolidin-2-one;
(E/Z)-4-[4-(2-Fluoro-phenyl)-4-methyl-2-oxo-imidazolidin-1-yl]-adamantane-1-carboxylic acid methyl ester;
4-(2-Chloro-phenyl)-1-((E)-5-hydroxy-adamantan-2-yl)-4-methyl-imidazolidin-2-one;
1-[(E)-5-Hydroxyadamantan-2-yl]-3',4'-dihydro-2H,2'H-spiro[imidazolidine-4,1'-naphthalen]-2-one;
1-((E)-5-Hydroxy-adamantan-2-yl)-4-methyl-4-naphthalen-2-yl-imidazolidin-2-one;
(E/Z)-4-[4-(4-Fluoro-phenyl)-4-methyl-2-oxo-imidazolidin-1-yl]-adamantane-1-carboxylic acid methyl ester;
(E/Z)-4-[4-(4-Chloro-phenyl)-4-methyl-2-oxo-imidazolidin-1-yl]-adamantane-1-carboxylic acid methyl ester;
(E/Z)-4-(4-Methyl-4-naphthalen-2-yl-2-oxo-imidazolidin-1-yl)-adamantane-1-carboxylic acid methyl ester;
Methyl(E/Z)-4-(2-oxo-3',4'-dihydro-1H,2'H-spiro[imidazolidine-4,1'-naphthalen]-1-yl)adamantane-1-carboxylate;
(E/Z)-4-[4-(2-Chloro-phenyl)-4-methyl-2-oxo-imidazolidin-1-yl]-adamantane-1-carboxylic acid methyl ester;
(E)-4-(2-oxo-3',4'-dihydro-1H,2'H-spiro[imidazolidine-4,1'-naphthalen]-1-yl)adamantane-1-carboxamide;
(E)-4-[4-(2-Fluoro-phenyl)-4-methyl-2-oxo-imidazolidin-1-yl]-adamantane-1-carboxylic acid amide;
4-(3-Chloro-phenyl)-1-((Z)-5-hydroxy-adamantan-2-yl)-4-methyl-imidazolidin-2-one;
4-(4-Chloro-phenyl)-1-((E)-5-hydroxy-adamantan-2-yl)-4-methyl-imidazolidin-2-one;
(S)-4-(4-Chloro-phenyl)-1-((E)-5-hydroxy-adamantan-2-yl)-4-methyl-imidazolidin-2-one;
(R)-4-(4-Chloro-phenyl)-1-((E)-5-hydroxy-adamantan-2-yl)-4-methyl-imidazolidin-2-one;
(E/Z)-4-[4-(3,4-Difluoro-phenyl)-4-methyl-2-oxo-imidazolidin-1-yl]-adamantane-1-carboxylic acid methyl ester;
1-((Z)-5-Hydroxy-adamantan-2-yl)-4-methyl-4-phenyl-imidazolidin-2-one;
1-((E)-5-Hydroxy-adamantan-2-yl)-4-methyl-4-phenyl-imidazolidin-2-one;
4-Ethyl-1-((E)-5-hydroxy-adamantan-2-yl)-4-phenyl-imidazolidin-2-one;
1-((Z)-5-Hydroxy-adamantan-2-yl)-4-methyl-4-phenethyl-imidazolidin-2-one;
1-((E)-5-Hydroxy-adamantan-2-yl)-4-methyl-4-phenethyl-imidazolidin-2-one;
1-((Z)-5-Hydroxy-adamantan-2-yl)-4-(2-methoxy-phenyl)-4-methyl-imidazolidin-2-one;
1-((E)-5-Hydroxy-adamantan-2-yl)-4-(2-methoxy-phenyl)-4-methyl-imidazolidin-2-one;
(1-((Z)-5-Hydroxy-adamantan-2-yl)-4-methoxymethyl-4-phenyl-imidazolidin-2-one;
1-((E)-5-Hydroxy-adamantan-2-yl)-4-methoxymethyl-4-phenyl-imidazolidin-2-one;
4-(3,4-Difluoro-phenyl)-1-((Z)-5-hydroxy-adamantan-2-yl)-4-methyl-imidazolidin-2-one;
4-(3,4-Difluoro-phenyl)-1-((E)-5-hydroxy-adamantan-2-yl)-4-methyl-imidazolidin-2-one;
(E)-4-(4-Methyl-4-naphthalen-2-yl-2-oxo-imidazolidin-1-yl)-adamantane-1-carboxylic acid amide;
(E)-4-[4-(2-Chloro-phenyl)-4-methyl-2-oxo-imidazolidin-1-yl]-adamantane-1-carboxylic acid amide;
(E)-4-[4-(4-Chloro-phenyl)-4-methyl-2-oxo-imidazolidin-1-yl]-adamantane-1-carboxylic acid amide;
(E)-4-[4-(3,4-Difluoro-phenyl)-4-methyl-2-oxo-imidazolidin-1-yl]-adamantane-1-carboxylic acid amide;
4-(3-Fluoro-phenyl)-1-((Z)-5-hydroxy-adamantan-2-yl)-4-methyl-imidazolidin-2-one;
4-(3-Fluoro-phenyl)-1-((E)-5-hydroxy-adamantan-2-yl)-4-methyl-imidazolidin-2-one;
4-(3-Bromo-phenyl)-1-((Z)-5-hydroxy-adamantan-2-yl)-4-methyl-imidazolidin-2-one;
(4-(3-Bromo-phenyl)-1-((E)-5-hydroxy-adamantan-2-yl)-4-methyl-imidazolidin-2-one;
4-(2,4-Difluoro-phenyl)-1-((Z)-5-hydroxy-adamantan-2-yl)-4-methyl-imidazolidin-2-one;
4-(2,4-Difluoro-phenyl)-1-((E)-5-hydroxy-adamantan-2-yl)-4-methyl-imidazolidin-2-one;
(E)-4-[4-(3-Fluoro-phenyl)-4-methyl-2-oxo-imidazolidin-1-yl]-adamantane-1-carboxylic acid amide;
4-(3-Chloro-4-fluoro-phenyl)-1-((E)-5-hydroxy-adamantan-2-yl)-4-methyl-imidazolidin-2-one;
1-((E)-5-Hydroxy-adamantan-2-yl)-4-(3-methoxy-phenyl)-4-methyl-imidazolidin-2-one;
1-((E)-5-Hydroxy-adamantan-2-yl)-4-(4-methoxy-phenyl)-4-methyl-imidazolidin-2-one;
1-((Z)-5-Hydroxy-adamantan-2-yl)-4-methyl-4-(4-trifluoromethoxy-phenyl)-imidazolidin-2-one;
1-((E)-5-Hydroxy-adamantan-2-yl)-4-methyl-4-(4-trifluoromethoxy-phenyl)-imidazolidin-2-one;
1-((Z)-5-Hydroxy-adamantan-2-yl)-4-methyl-4-(3-trifluoromethyl-phenyl)-imidazolidin-2-one;
1-((E)-5-Hydroxy-adamantan-2-yl)-4-methyl-4-(3-trifluoromethyl-phenyl)-imidazolidin-2-one;
4-(4-Chloro-3-trifluoromethyl-phenyl)-1-((Z)-5-hydroxyadamantan-2-yl)-4-methyl-imidazolidin-2-one;
4-(4-Chloro-3-trifluoromethyl-phenyl)-1-((E)-5-hydroxyadamantan-2-yl)-4-methyl-imidazolidin-2-one;
(E/Z)-4-[4-(2,4-Difluoro-phenyl)-4-methyl-2-oxo-imidazolidin-1-yl]-adamantane-1-carboxylic acid methyl ester;
(E)-4-[4-(2,4-Difluoro-phenyl)-4-methyl-2-oxo-imidazolidin-1-yl]-adamantane-1-carboxylic acid amide;
(E/Z)-4-[4-(3-Fluoro-phenyl)-4-methyl-2-oxo-imidazolidin-1-yl]-adamantane-1-carboxylic acid methyl ester;
1-((E)-5-Hydroxy-adamantan-2-yl)-4-methyl-4-m-tolyl-imidazolidin-2-one;

1-((Z)-5-Hydroxy-adamantan-2-yl)-4-methyl-4-naphthalen-2-yl-imidazolidin-2-one;
(E/Z)-4-[4-(3-Bromo-phenyl)-4-methyl-2-oxo-imidazolidin-1-yl]-adamantane-1-carboxylic acid methyl ester;
(Z)-4-(4-Methyl-4-naphthalen-2-yl-2-oxo-imidazolidin-1-yl)-adamantane-1-carboxylic acid amide;
(E/Z)-4-[4-(3,4-Dimethoxy-phenyl)-4-methyl-2-oxo-imidazolidin-1-yl]-adamantane-1-carboxylic acid methyl ester;
1-((E/Z)-5-Hydroxy-adamantan-2-yl)-4-methyl-4-pyridin-3-yl-imidazolidin-2-one;
(E/Z)-4-[4-(3-Chloro-4-fluoro-phenyl)-4-methyl-2-oxo-imidazolidin-1-yl]-adamantane-1-carboxylic acid methyl ester;
(E)-4-[4-(3-Chloro-4-fluoro-phenyl)-4-methyl-2-oxo-imidazolidin-1-yl]-adamantane-1-carboxylic acid amide;
4-(3-Chloro-4-fluoro-phenyl)-1-((E)-5-hydroxy-adamantan-2-yl)-4-methyl-imidazolidin-2-one;
4-(3,4-Difluoro-phenyl)-1-((E)-5-hydroxymethyl-adamantan-2-yl)-4-methyl-imidazolidin-2-one;
4-(2-Chloro-phenyl)-1-((E)-5-hydroxymethyl-adamantan-2-yl)-4-methyl-imidazolidin-2-one;
4-(2-Fluoro-phenyl)-1-((E)-5-hydroxymethyl-adamantan-2-yl)-4-methyl-imidazolidin-2-one;
1-((E)-5-Hydroxy-adamantan-2-yl)-3,4-dimethyl-4-phenyl-imidazolidin-2-one;
1-((Z)-5-Hydroxy-adamantan-2-yl)-3,4-dimethyl-4-phenyl-imidazolidin-2-one;
4-(4-Chloro-phenyl)-1-((E/Z)-5-hydroxy-adamantan-2-yl)-3,4-dimethyl-imidazolidin-2-one;
4-(4-Fluoro-phenyl)-1-((Z)-5-hydroxy-adamantan-2-yl)-3,4-dimethyl-imidazolidin-2-one;
4-(4-Fluoro-phenyl)-1-((E)-5-hydroxy-adamantan-2-yl)-3,4-dimethyl-imidazolidin-2-one;
4-(4-Fluoro-phenyl)-1-((Z)-5-hydroxy-adamantan-2-yl)-3,4-dimethyl-imidazolidin-2-one;
4-(2-Fluoro-phenyl)-1-((E)-5-hydroxy-adamantan-2-yl)-3,4-dimethyl-imidazolidin-2-one;
3-Benzyl-1-((Z)-5-hydroxy-adamantan-2-yl)-4-methyl-4-phenyl-imidazolidin-2-one;
3-Benzyl-1-((E)-5-hydroxy-adamantan-2-yl)-4-methyl-4-phenyl-imidazolidin-2-one;
(E/Z)-4-(3,4-Dimethyl-2-oxo-4-phenyl-imidazolidin-1-yl)-adamantane-1-carboxylic acid methyl ester;
(E/Z)-4-[4-(4-Chloro-phenyl)-3,4-dimethyl-2-oxo-imidazolidin-1-yl]-adamantane-1-carboxylic acid methyl ester;
(E)-4-(3,4-Dimethyl-2-oxo-4-phenyl-imidazolidin-1-yl)-adamantane-1-carboxylic acid;
(E)-4-(4-Benzyloxymethyl-3-methyl-2-oxo-imidazolidin-1-yl)-adamantane-1-carboxylic acid amide;
1-((E)-5-Hydroxy-adamantan-2-yl)-4-hydroxymethyl-3-methyl-imidazolidin-2-one; and
6-[1-((E)-5-Hydroxy-adamantan-2-yl)-3-methyl-2-oxo-imidazolidin-4-ylmethoxy]-nicotinonitrile.

Further examples of particularly preferred compounds of the invention are:
1-[(E)-4-(2-oxo-1',3'-dihydro-1H-spiro[imidazolidine-4,2'-inden]-1-yl)adamantan-1-yl]urea;
N-[(E)-4-(3-methyl-2-oxo-1',3'-dihydro-1H-spiro[imidazolidine-4,2'-inden]-1-yl)adamantan-1-yl]acetamide;
N-[(E)-4-(3-methyl-2-oxo-1',3'-dihydro-1H-spiro[imidazolidine-4,2'-inden]-1-yl)adamantan-1-yl]methanesulfonamide;
N-[(E)-4-(3-methyl-2-oxo-1',3'-dihydro-1H-spiro[imidazolidine-4,2'-inden]-1-yl)adamantan-1-yl]sulfamide;
2-hydroxy-N-[(E)-4-(3-methyl-2-oxo-1',3'-dihydro-1H-spiro[imidazolidine-4,2'-inden]-1-yl)adamantan-1-yl]acetamide;
(E/Z)-4-(2-oxo-1',3'-dihydro-1H-spiro[imidazolidine-4,2'-inden]-1-yl)adamantane-1-carboxamide;
1-[5-(E/Z)-(hydroxymethyl)adamantan-2-yl]-1',3'-dihydro-2H-spiro[imidazolidine-4,2'-inden]-2-one;
3-[(E/Z)-5-Hydroxymethyl-adamantan-2-yl]-1,3-diaza-spiro[4.4]nonan-2-one;
4-(1-Cyclopropyl-2-oxo-1,3-diaza-spiro[4.6]undec-3-yl)-benzamide;
4-(3-Cyclopropyl-4-isopropyl-2-oxo-imidazolidin-1-yl)-benzamide;
4-(1-Cyclopropyl-3-(4-methoxy-phenyl)-1,3-diaza-spiro[4.5]decan-2-one;
4-(1-Cyclopropyl-3-(4-hydroxy-phenyl)-1,3-diaza-spiro[4.5]decan-2-one;
3-(3-Chloro-4-hydroxy-phenyl)-1-cyclopropyl-1,3-diaza-spiro[4.5]decan-2-one;
1-Cyclopropyl-3-(2-trifluoromethyl-phenyl)-1,3-diaza-spiro[4.5]decan-2-one;
3-Cyclopropyl-1-(2,5-dichloro-phenyl)-4-isopropyl-imidazolidin-2-one;
(E)-4-[4-(3-Chloro-phenyl)-4-methyl-2-oxo-imidazolidin-1-yl]-adamantane-1-carboxylic acid amide;
4-(2-Fluoro-phenyl)-1-((E/Z)-5-hydroxy-adamantan-2-yl)-4-methyl-imidazolidin-2-one;
4-(3-Chloro-phenyl)-1-((E)-5-hydroxy-adamantan-2-yl)-4-methyl-imidazolidin-2-one;
4-(2-Chloro-phenyl)-1-((E)-5-hydroxy-adamantan-2-yl)-4-methyl-imidazolidin-2-one;
(E)-4-[4-(2-Fluoro-phenyl)-4-methyl-2-oxo-imidazolidin-1-yl]-adamantane-1-carboxylic acid amide;
(S)-4-(4-Chloro-phenyl)-1-((E)-5-hydroxy-adamantan-2-yl)-4-methyl-imidazolidin-2-one;
(R)-4-(4-Chloro-phenyl)-1-((E)-5-hydroxy-adamantan-2-yl)-4-methyl-imidazolidin-2-one;
1-((E)-5-Hydroxy-adamantan-2-yl)-4-methyl-4-phenyl-imidazolidin-2-one;
1-((E)-5-Hydroxy-adamantan-2-yl)-4-methyl-4-phenethyl-imidazolidin-2-one;
(E)-4-(4-Methyl-4-naphthalen-2-yl-2-oxo-imidazolidin-1-yl)-adamantane-1-carboxylic acid amide;
(E)-4-[4-(2-Chloro-phenyl)-4-methyl-2-oxo-imidazolidin-1-yl]-adamantane-1-carboxylic acid amide;
(E)-4-[4-(4-Chloro-phenyl)-4-methyl-2-oxo-imidazolidin-1-yl]-adamantane-1-carboxylic acid amide;
(E)-4-[4-(3,4-Difluoro-phenyl)-4-methyl-2-oxo-imidazolidin-1-yl]-adamantane-1-carboxylic acid amide;
(E)-4-[4-(3-Fluoro-phenyl)-4-methyl-2-oxo-imidazolidin-1-yl]-adamantane-1-carboxylic acid amide;
(E)-4-[4-(3-Chloro-4-fluoro-phenyl)-4-methyl-2-oxo-imidazolidin-1-yl]-adamantane-1-carboxylic acid amide;
(E)-4-[(R)-4-(3,4-Difluoro-phenyl)-4-methyl-2-oxo-imidazolidin-1-yl]-adamantane-1-carboxylic acid amide;
(E)-4-[(S)-4-(3,4-Difluoro-phenyl)-4-methyl-2-oxo-imidazolidin-1-yl]-adamantane-1-carboxylic acid amide;
(E)-4-[(R)-4-(3-Fluoro-phenyl)-4-methyl-2-oxo-imidazolidin-1-yl]-adamantane-1-carboxylic acid amide; and
(E)-4-[(S)-4-(3-Fluoro-phenyl)-4-methyl-2-oxo-imidazolidin-1-yl]-adamantane-1-carboxylic acid amide.

Processes for the manufacture of compounds of formula I are an embodiment of the invention.

The preparation of compounds of formula I of the present invention may be carried out in sequential or convergent synthetic routes. Syntheses of the invention are shown in the following Schemes. The skills required for carrying out the reaction and purification of the resulting products are known to those persons skilled in the art. The substituents and indices used in the following description of the processes have the significance given above unless indicated to the contrary. In cases where the substituent index is followed by a prime or double prime (e.g. $R^{2'}$ or $R^{2''}$) it is implicated, that the reaction sequence has been carried out with a subset of the corresponding substituent $R^X$ which is defined in the section above. An alternative reaction sequence may have been used for a different subset of $R^X$ (refer to the examples section for details).

Compounds of formula (I) are consisting of imidazolones of formula (II) and of imidazolidinones of formula (III). Imidazolones of formula (II) are accessible according to the following general Scheme 1, entry 1]. A key structure in this first synthetic approach is a suitably substituted amino acid ester C. Derivatives of such compounds are known in the literature and can be accessed, for example, either from suitable α-halo acetic acid esters A by reaction with an appropriately substituted amine $R^{2'}$—$NH_2$ or by esterification of suitably substituted amino acids B under known conditions such as e.g. $SOCl_2$ in the presence of a lower alcohol $R^8$—OH such as methanol of ethanol. Amino acid esters C are then reacted with an appropriate isocyanate $R^1$—NCO D in a suitable solvent such as DMF, $CH_2Cl_2$, THF or diethylether or the like to give an urea E. This material is subsequently transformed to an imidazolone (IIa) by reduction with a suitable reducing agent such as diisobutylaluminium hydride or sodium dihydrido-bis-methoxy-ethoxy aluminate or the like followed by treatment with a strong mineral acid such as HCl, HBr or $H_2SO_4$ or the like. In some cases, this material is already one of the desired imidazolones of formula (IIa). Optionally, if $R^{2'}$ is H such as in structure F, an additional substituent $R^{2''}$ can be introduced by alkylation of the nitrogen under standard alkylation conditions. Standard alkylation conditions are consisting of treatment of an imidazolone F with a base such as e.g. NaH, KOtBu, $CsCO_3$, $Na_2CO_3$ or the like followed by an appropriate alkylation agent $R^{2''}$-X where X is a halide or a sulfonic acid ester to give the desired compound of formula (IId) (Scheme 1, entry 2]).

Scheme 1:

1]

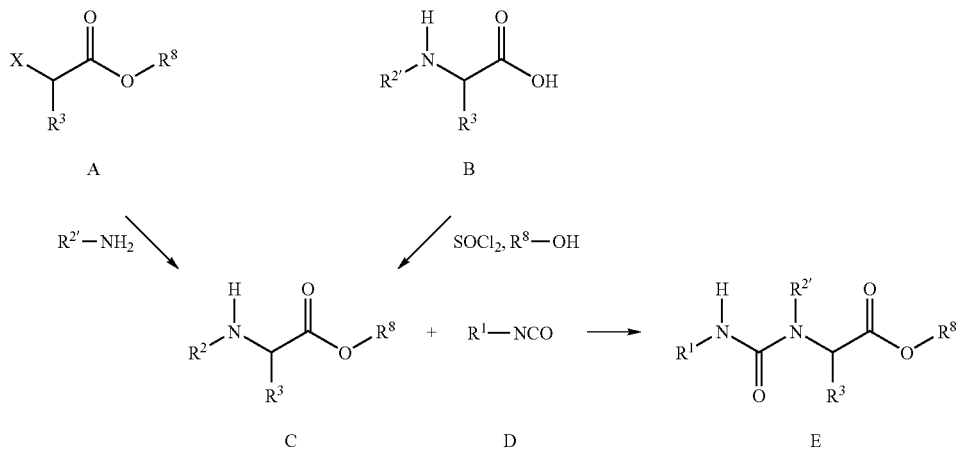

2]

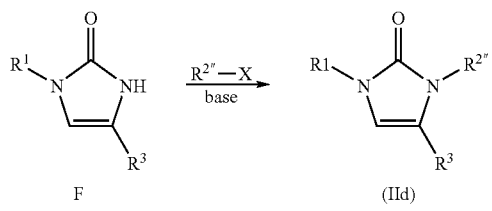

X = halogen (Cl, Br, I) or sulfonyl ester
R8 = lower alkyl

Isocyanates $R^1$—NCO D which are required for the coupling reaction described in Scheme 1 to provide the urea intermediates E are accessible from suitable carboxylic acid derivatives G by means of a degradation reaction such as Curtius or Hoffmann rearrangement under various conditions. Conditions for those reactions are well known and can be found in the literature. Scheme 2 exemplifies isocyanate formation starting from a carboxylic acid by treatment with e.g. diphenylphosphoryl azide and $NEt_3$. Alternatively, isocyanates D can also be made from suitable amines $R^1$—$NH_2H$ by treatment with phosgene or phosgene equivalents such as diphosgene or triphosgene under conditions that are known to those skilled in the art.

Scheme 2:

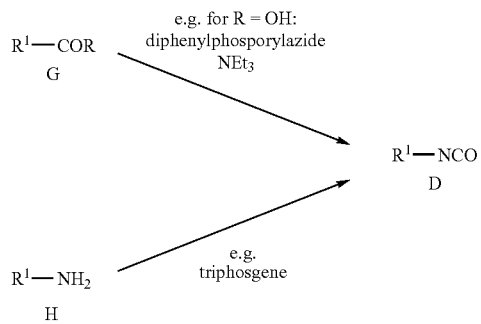

Compounds of formula (IIc) with $R^5 \neq H$ can be accessed via the following routes: An α-aminoketone I is used as a starting material instead of an ester C. Access to α-aminoketones I is known in the literature and can be based on e.g. Dakin-West reaction of suitably substituted amino acids and the proper carboxylic acid anhydride. In analogy to the sequence outlined in Scheme 1, aminoketone I is treated with a suitable isocyanate D to give an urea K which is cyclized to an imidazolone of formula (II) by treatment with a mineral acid such as HCl, HBr, $H_2SO_4$ or the like (Scheme 3, entry 1]).

In some individual cases which are strongly dependent on the nature of the alkylation agent, imidazolone compounds with $R^5 \neq H$ have been accessible via C-alkylation of the corresponding unsubstituted imidazolone precursor F under alkylation conditions that have been described previously (Scheme 3, entry 2]).

Imidazolone compounds of formula (IIb) in which $R^1$ is a benzyl type substituent are accessible via a special route that is described in Scheme 3, entry 3]. The imidazolone core carrying substituents $R^2$ and $R^3$, respectively, is accessible via a 3-component reaction of an α-chloroactone derivative L, an amine M and potassium isocyanate in a solvent such as DMF, THF or the like at temperatures ranging from 0° C. to 120° C. to give an imidazolone N. Alkylation of the unsubstituted nitrogen of the intermediate imidazolone N with a suitable benzylic alkylation agent $R^9$—X under conditions described previously leads to imidazolone compounds of formula (IIb) with benzyl type $R^1$ substituents.

Scheme 3:

1]

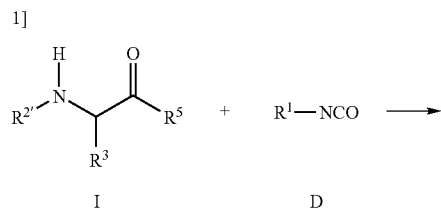

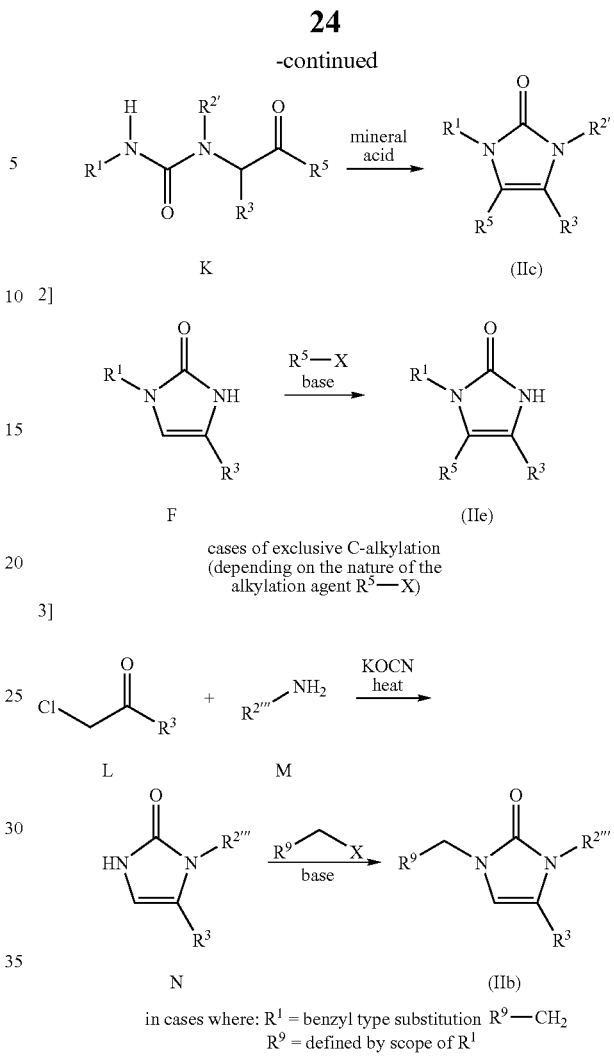

Some imidazolidinones of formula (III) are directly accessible from the corresponding imidazolones of formula (IIe) by catalytic hydrogenation with hydrogen in the presence of a catalyst such as platinum on charcoal, palladium on charcoal, or the like in a broad range of solvents at various temperatures and pressures (Scheme 4).

Scheme 4:

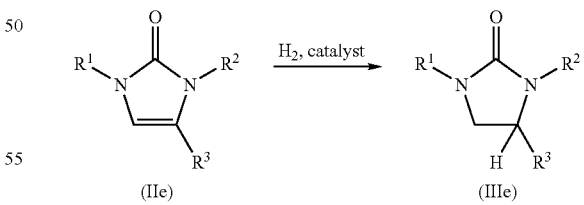

Other imidazolidinones of formula (III) can be made according to the following general reaction sequence which is outlined in Scheme 5: The initial step of the reaction sequence is consisting of a Strecker synthesis of an appropriate aldehyde or ketone O with ammonia or an amine P in the presence of sodium cyanide, potassium cyanide, trimethylsilylcyanide or the like to give a suitably substituted α-amino nitrile Q. Nitrile Q is then reduced to a diamine R by treatment with a suitable metal hydride such as diisobutylaluminium hydride, lithium aluminium hydride or the like or alternatively by catalytic hydrogenation. Diamine R is then regioselectively coupled to a suitable ketone S in a reductive amination process which consists of forming an intermediate imine that is then reduced to an amine T with suitable reducing agents such as sodium borohydride, sodium cyanoborohydride, sodium triacetoxyborohydride or the like. Treatment of this diamine T with phosgene or a phosgene equivalent such as diphosgene, triphosgene or carbonyldiimidazole at temperatures ranging from −10° C. to 150° C. in the presence of a base such as triethylamine, diisopropylamine, $K_2CO_3$, $Na_2CO_3$ or the like, if needed, results in the formation of an imidazolidinone which may already be a compound of the desired structure (IIIb). Optionally, if $R^{2'}$ is H such as in compound U, an additional substituent $R^{2''}$ can be introduced by alkylation of the nitrogen under standard alkylation conditions. Standard alkylation conditions are consisting of treatment of an imidazolidinone U with a base such as e.g. NaH, KOtBu, $CsCO_3$, $K_2CO_3$, $Na_2CO_3$ or the like followed by an appropriate alkylation agent $R^{2''}$—X where X is a halide or a sulfonic acid ester to give the desired compound of formula (IIIb). If $R^{2''}$ cannot be introduced via N-alkylation, e.g. due to the lack of suitable alkylation agents, the substituent $R^2$ needs to be introduced at the beginning of the reaction sequence, using the appropriate starting materials in the Strecker Synthesis.

Some diamine intermediates T are not accessible via this reductive amination route due to the fact that there are no ketone building blocks S for this type of $R^1$. An alternative route for making some of these examples with a particular set of $R^1$ substituents is shown in the following Scheme 6. This method consists of an initial amide bond formation between a suitable amine or aniline V and a protected aminoacid W using amide coupling conditions that are well known in the literature to give protected amide X. Deprotection of X under suitable conditions which are depending on the protecting group chosen gives deprotected amide Y. As exemplified in Scheme 6, a suitable protection group is for example a tert-butoxycarbonyl group (BOC-group) that can be removed e.g. by treatment with acids such as trifluoroacetic acid or HCl or the like in solvents such as $CH_2Cl_2$ or dioxane or the like). Deprotected amide Y can be reduced to diamine Z by treatment with appropriate reducing agents such as $BH_3$-THF complex, $BH_3$ dimethylsulfide complex, lithium aluminium hydride or the like. Diamine Z is then transformed to the desired imidazolidinones O or (III), respectively, as described and outlined earlier in Scheme 5.

Scheme 5:

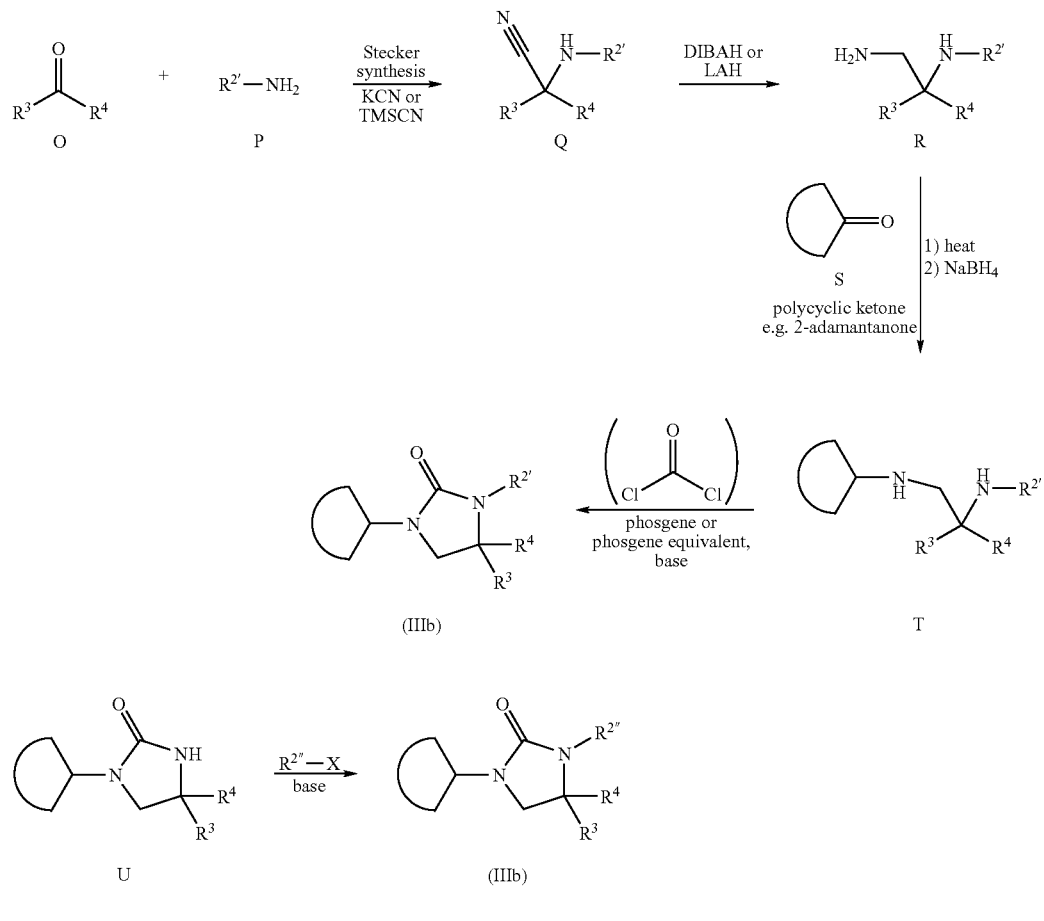

Scheme 6:

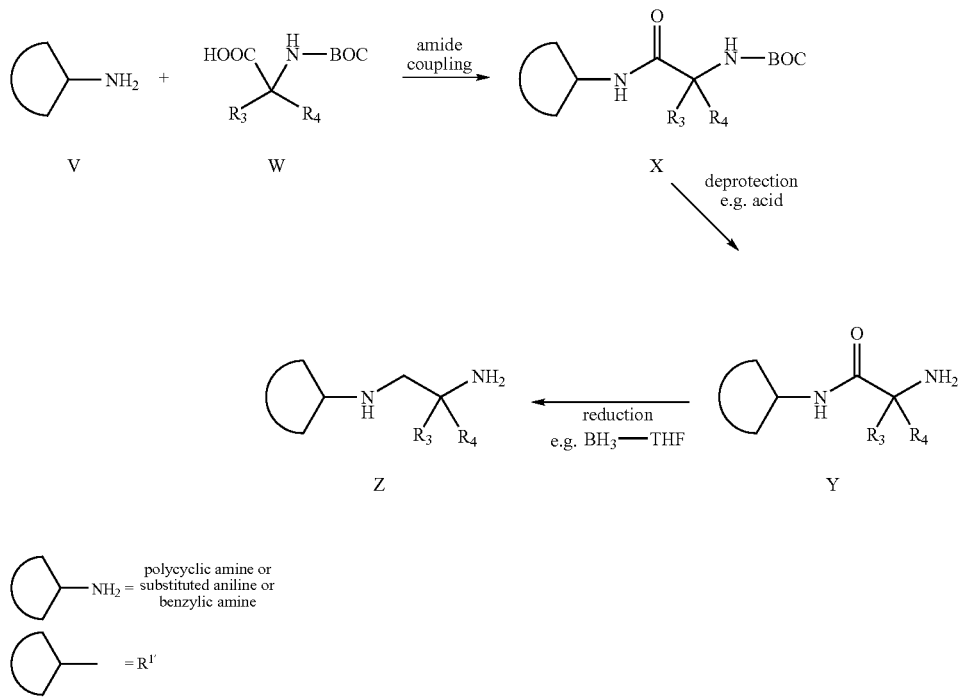

A yet another alternative route for making some of the examples of this invention is outlined in Scheme 7 below. α-Aminonitriles AA can be hydrolyzed to the free acid AB using methods well known in the literature. Direct reduction of the acid AB or, alternatively, an esterification/reduction sequence (via α-amino-ester AC) that may involve conditions outlined previously, will furnish aminoethanol AD. Coupling of building block AD with a suitable isocyanate $R^4$—NCO D under conditions described earlier will provide urea AE. Treatment of urea AE with a suitable base such a potassium tert-butylate, sodium ethylate, sodium hydride or the like in the presence of a sulfonyl chloride such as p-toluenesulfonyl chloride or methanesulfonyl chloride at temperatures ranging from −40° C. to 130° C. in THF, DMF or ether or the like results in the formation of an imidazolidinone of formula (IIIc). Note that if $R^{2'}$ is hydrogen, formation of regioisomeric cyclization products needs to be taken into account in the final cyclization step.

A yet further alternative route for making the compounds of this invention consists of coupling the α-aminonitriles AA with the isocanate D in the presence of a base such as triethyl amine or sodium hydride to give the imidazolidine-2,4-dione AF after hydrolysis (scheme 7). This can then be transformed to (IIIc) by selective reduction, either performed in a 2-step process as described in the experimental part, first treatment with sodium borohydride in methanol or DIBAH in THF followed by reduction of the hydroxyl imidazolidin-2-one intermediate with sodium borohydride in trifluoroacetic acid, or by using $LiAlH_4/AlCl_3$ as reducing agent in analogy to a procedure described by Shen et al (Biorg. Med. Chem. Lett., 2005, 4564).

The isocanates of formula D are either commercially available, known in the literature or can be obtained in analogy to known procedures. Thus, as described in the experimental part, compounds of formula D where R1 equals substituted aryl, can be obtained from the respective substituted amines upon reaction with trichloromethyl chloroformate. The respective substitutents at R1 as defined above are either present in the starting material or can be obtained by functional group conversion following known methods. Thus, compounds where R1 equals 4-aminocarbonyl phenyl can be prepared from the corresponding alkyloxy-carbonyl intermediates by ester hydrolysis with LiOH in $THF/H_2O$ and subsequent amide formation reaction with, e.g., ammonium acetate and 1,1-carbonyl diimidazole as a coupling reagent.

Scheme 7:

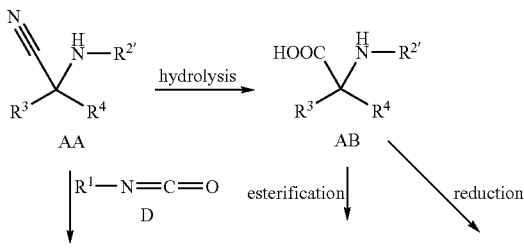

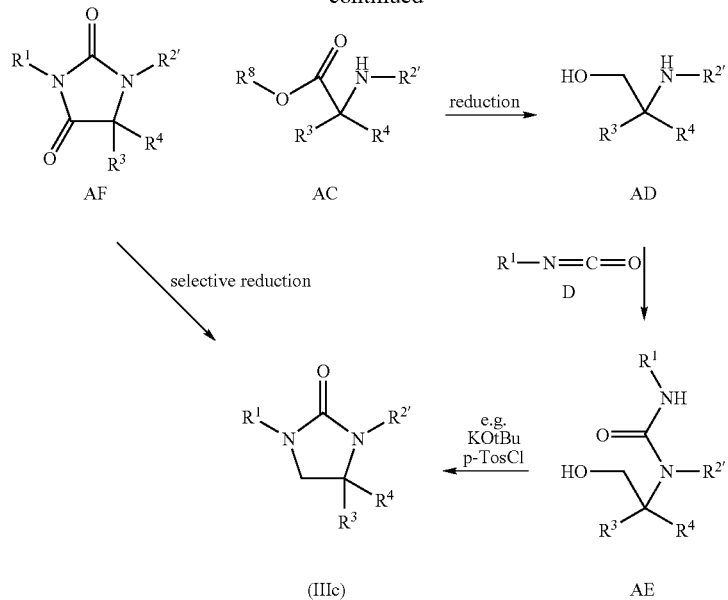

Compound according to formula (III), wherein $R^5$ and/or $R^6$ are not hydrogen can be prepared in analogy to Scheme 7, wherein appropriate analogues of intermediates AD and AE, respectively, are used which are substituted with $R^5$ and/or $R^6$ in α-position to the free hydroxy group. Such analogues can be made from suitably protected α-amino acid esters or acids or derivatives thereof (derivatives of AC) by addition of organometallic reagents or from suitably protected 2-aminoalkan-1-ols (derivatives of intermediate AD) by oxidation followed by addition of a suitable organometallic reagent to introduce $R^5$ and/or $R^6$. Depending on the substitution pattern of the amine function, an additional deprotection step may be needed before coupling with an isocyanate D. In addition to the conditions described previously, formation of imidazolidinone III in which non-hydrogen substituents $R^5$ and/or $R^6$ are present may need to be conducted under alternative reaction conditions such as treatment with acids, Lewis acids or suitable metals or eventually under activation by formation of a chloride, bromide, sulfonate or the like.

Compounds of this invention were $R^1$ equals substituted adamantyl as defined can be prepared either according to schemes 5, 6, or 7 starting from the respective substituted adamantyl amines or polycylic ketones or as described in scheme 8.

Scheme 8:

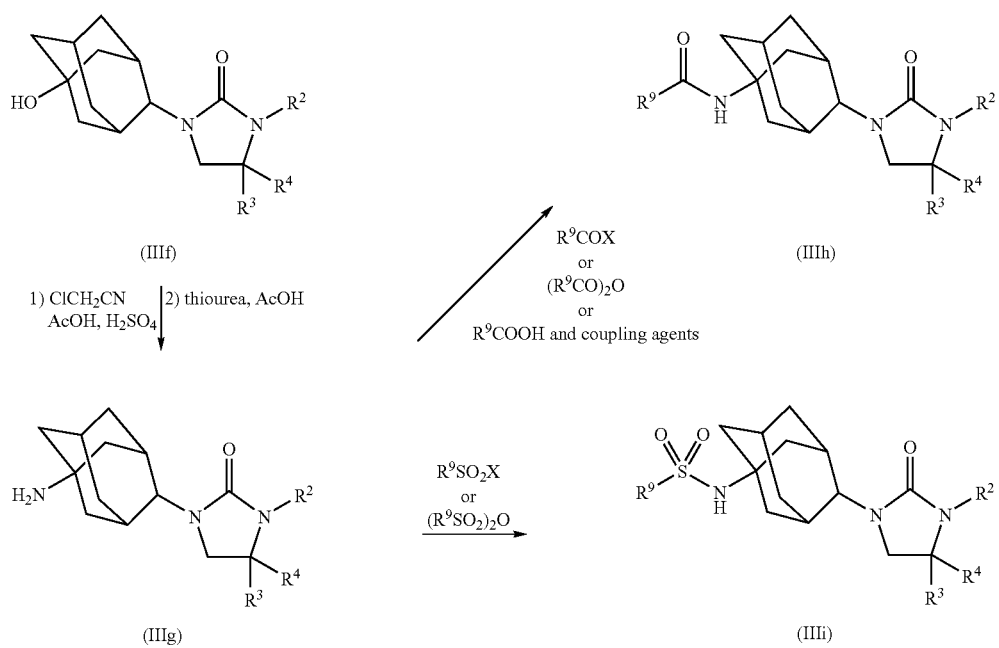

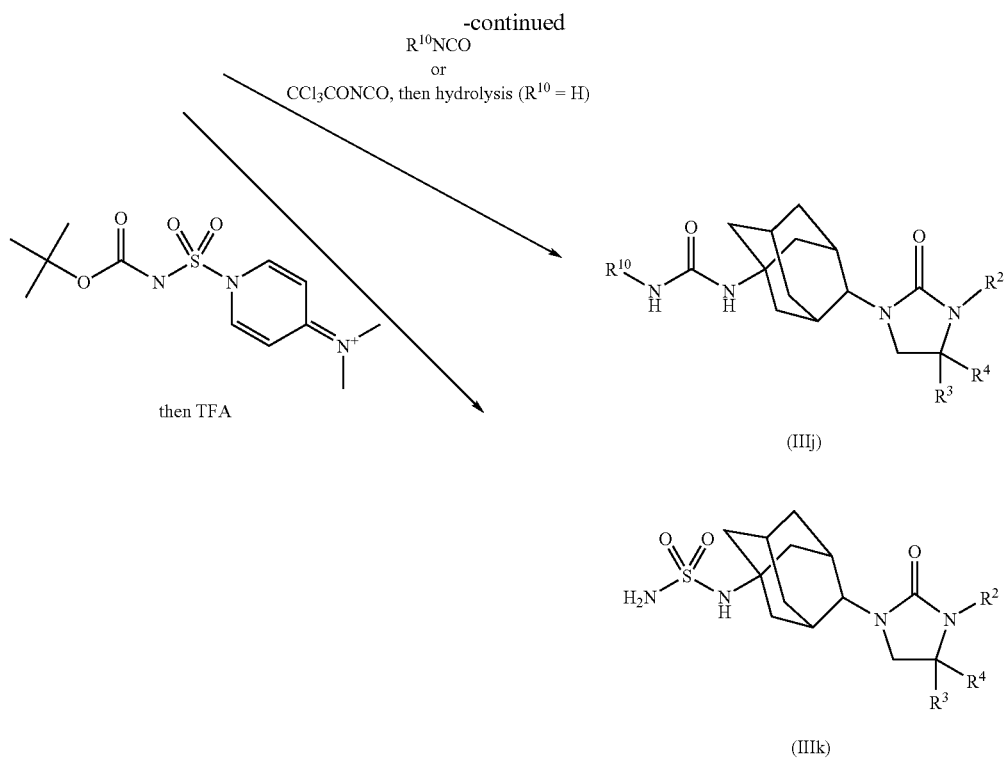

-continued (IIIj)

(IIIk)

Thus, the compound of general formula (IIIf), prepared according to schemes 5 and 6, may be reacted by the procedure of Jirgensons et al. (Synthesis, 12, 2000, 1709) with chloroacetonitrile in the presence of acetic acid and sulfuric acid, followed by cleavage of amide with thiourea and acetic acid to give a compound of general formula (IIIg).

The compound of general formula (IIIg) may be reacted with an acyl halide ($R^9COX$; $R^9$=an optionally substituted alkyl group, X=a halide) and a base, a carboxylic anhydride (($R^9CO)_2O$; $R^9$=an optionally substituted alkyl group) and a base or a carboxylic acid ($R^9COOH$; $R^9$=an optionally substituted alkyl group) in the presence of (a) coupling reagent(s) to give a amide derivative of general formula (IIIh). Suitable bases include triethylamine, N,N-diisopropylethylamine (DIPEA), pyridine, 2,6-lutidine, 2,4,6-collidine, N,N-dimethylaminopyridine, N-methylmorpholine, and the like. Suitable coupling reagents include EDC, TBTU, HATU, HOBT, and the like.

The compound of general formula (IIIg) may be reacted with an sulfonyl halide ($R^9SO_2X$; $R^9$=an optionally substituted alkyl group, X=a halide) and a base, and a sulfonic anhydride (($R^9SO_2)_2O$; $R^9$=an optionally substituted alkyl group to give a sulfonamide derivative of general formula (IIIi). Suitable bases include triethylamine, N,N-diisopropylethylamine (DIPEA), pyridine, 2,6-lutidine, 2,4,6-collidine, N,N-dimethylaminopyridine, N-methylmorpholine, and the like.

The compound of general formula (IIIg) may be reacted with an isocyanate ($R^{10}NCO$; $R^{10}$=an optionally substituted alkyl group to give a urea derivative of general formula (IIIj). For the formation of non-substituted urea of general formula (IIIj) ($R^{10}$=a hydrogen), the compound of general formula (IIIg) may be reacted with an trichloroacetyl isocyanate, followed by hydrolysis with a base. Suitable bases for hydrolysis include sodium hydroxide, potassium hydroxide, lithium hydroxide, and the like.

The compound of general formula (IIIg) may be reacted with 4-(dimethylamino)-1-[[[(1,1-dimethylethoxy)carbonyl]amino]sulfonyl]-pyridinium inner salt and a base, followed by treatment with acid to give a sulfamide derivative of general formula (IIIk). Suitable bases include triethylamine, N,N-diisopropylethylamine (DIPEA), pyridine, 2,6-lutidine, 2,4,6-collidine, N,N-dimethylaminopyridine, N-methylmorpholine, and the like. Suitable acids include trifluoroacetic acid, hydrochloric acid, sulfuric acid, methanesulfonic acid, and the like.

In cases were compounds of formula I are present in form of mixtures of enantiomers as racemates, these can be separated into the corresponding optically pure enantiomers by chiral HPLC.

A preferred process for the preparation of a compound of formula I as described before comprises one of the following reactions, wherein $R^1$ to $R^6$ are defined as before:

a) reaction of a compound according to formula

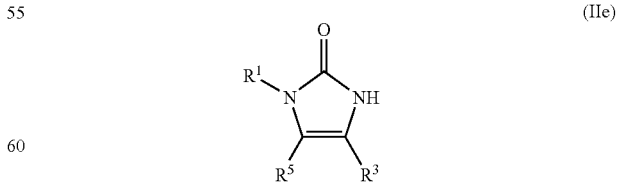

(IIe)

in the presence of $R^2$—X, wherein X is halide or sulfonic acid, preferably chloro or bromo, and preferably in the presence of a base, preferably NaH, KOtBu, $CsCO_3$ or $Na_2CO_3$, in order to obtain a compound of formula

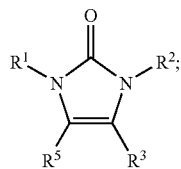
(II)

b) reaction of a compound according to formula

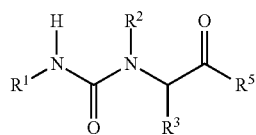
$K_a$ in the presence of an acid, preferably a mineral acid such as e.g. HCl, HBr or $H_2SO_4$ in order to obtain a compound of formula

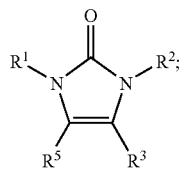
(II)

c) reaction of a compound according to formula

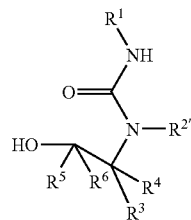
(IV)

in the presence of a base, preferably e.g. potassium tert-butylate, sodium ethylate, sodium hydride and preferably in the presence of a sulfonylchloride such as p-toluenesulfonylchloride or methanesulfonylchloride, in order to obtain a compound of formula

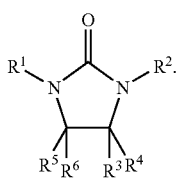
(III)

Preferred intermediates are:
(3-Adamantan-2-yl-1-benzyl-ureido)-acetic acid ethyl ester
(3-Adamantan-2-yl-1-pyridin-2-ylmethyl-ureido)-acetic acid ethyl ester
(3-Adamantan-2-yl-1-isopropyl-ureido)-phenyl-acetic acid methyl ester
Cyclopropylamino-phenyl-acetic acid methyl ester
(3-Adamantan-2-yl-1-cyclopropyl-ureido)-phenyl-acetic acid methyl ester
Cyclopropylamino-(3-fluoro-phenyl)-acetic acid methyl ester
(3-Adamantan-2-yl-1-cyclopropyl-ureido)-(3-fluoro-phenyl)-acetic acid methyl ester
Cyclopropylamino-pyridin-2-yl-acetic acid methyl ester
(3-Adamantan-2-yl-1-cyclopropyl-ureido)-pyridin-2-yl-acetic acid methyl ester
(S)-2-(3-Adamantan-2-yl-ureido)-3,3-dimethyl-butyric acid methyl ester
2-(3-Adamantan-2-yl-ureido)-3-methyl-butyric acid methyl ester
(3-Adamantan-2-yl-ureido)-phenyl-acetic acid methyl ester
(S)-2-(3-Adamantan-2-yl-ureido)-4-methyl-pentanoic acid methyl ester
(R)-2-(3-Adamantan-2-yl-ureido)-3-(3-fluoro-phenyl)-propionic acid methyl ester
(2S,3S)-2-(3-Adamantan-2-yl-ureido)-3-methyl-pentanoic acid methyl ester
H-beta-tert-butyl-D,L-alanine methyl ester hydrochloride
2-(3-Adamantan-2-yl-ureido)-4,4-dimethyl-pentanoic acid methyl ester
(3-Adamantan-2-yl-ureido)-cyclohexyl-acetic acid methyl ester
(S)-(3-Adamantan-2-yl-ureido)-cyclopropyl-acetic acid methyl ester
2-Amino-4,4,4-trifluoro-butyric acid methyl ester hydrochloride
2-(3-Adamantan-2-yl-ureido)-4,4,4-trifluoro-butyric acid methyl ester
(S)-2-Amino-3-cyclopropyl-propionic acid methyl ester hydrochloride
(S)-2-(3-Adamantan-2-yl-ureido)-3-cyclopropyl-propionic acid methyl ester
(S)-4-Methyl-2-[3-(2-trifluoromethyl-phenyl)-ureido]-pentanoic acid methyl ester
3-Methyl-2-[3-(2-trifluoromethyl-phenyl)-ureido]-butyric acid methyl ester ester
(S)-2-(3-Adamantan-1-yl-ureido)-4-methyl-pentanoic acid methyl ester
2-(3-Adamantan-1-yl-ureido)-3-methyl-butyric acid methyl ester
(S)-2-((1R,2S,4S/1S, 2R,4R)-3-Bicyclo[2.2.1]hept-2-ylureido)-3,3-dimethyl-butyric acid methyl ester (1:1 mixture of 2 diastereomers)
2-Cyclopropylamino-3-methyl-butyric acid ethyl ester
2-(3-Adamantan-2-yl-1-cyclopropyl-ureido)-3-methyl-butyric acid ethyl ester
1-Cyclopropyl-5-methyl-1,3-dihydro-imidazol-2-one
2-{3-[1-(4-Chloro-phenyl)-cyclopropyl]-ureido}-3-methyl-butyric acid methyl ester
1-Adamantan-2-yl-3-(1-benzyl-3-methyl-2-oxo-butyl)-urea
(S)-2-[3-[(E)-5-hydroxy-adamantan-2-yl]-ureido]-4-methyl-pentanoic acid methyl ester
(S)-2-[3-[(Z)-5-hydroxy-adamantan-2-yl]-ureido]-4-methyl-pentanoic acid methyl ester
(S)-2-[3-(2-Methoxy-phenyl)-ureido]-4-methyl-pentanoic acid methyl ester
(S)-4-Methyl-2-[3-(2-trifluoromethoxy-phenyl)-ureido]-pentanoic acid methyl ester
(S)-2-[3-(2,4-Difluoro-phenyl)-ureido]-4-methyl-pentanoic acid methyl ester
2-Methyl-6-trifluoromethyl-phenyl-isocyanate (S)-4-Methyl-2-[3-(2-methyl-6-trifluoromethyl-phenyl)-ureido]-pentanoic acid methyl ester
2-Cyclopropylamino-4-methyl-pentanenitrile hydrochloride
3-Adamantan-2-yl-1-(1-cyano-3-methyl-butyl)-1-cyclopropyl-urea
2-[1-Cyclopropyl-3-(2-trifluoromethyl-phenyl)-ureido]-3-methyl-butyric acid methyl ester
$N^1$-Adamantan-2-yl-2-methyl-propane-1,2-diamine
(E/Z)-4-(2-Amino-2-methyl-propylamino)-adamantan-1-ol
[1-(Adamantan-2-ylcarbamoyl)-cyclopentyl]-carbamic acid tert-butyl ester
1-Amino-cyclopentanecarboxylic acid adamantan-2-ylamide
Adamantan-2-yl-(1-amino-cyclopentylmethyl)-amine
2-Cyclopropylamino-3-methyl-butan-1-ol
1-Cyclopropyl-1-(1-hydroxymethyl-2-methyl-propyl)-3-(2-trifluoromethyl-phenyl)-urea
Cyclopropyl-cyclopropylamino-acetonitrile
Cyclopropyl-cyclopropylamino-acetic acid
2-Cyclopropyl-2-cyclopropylamino-ethanol
1-Cyclopropyl-1-(1-cyclopropyl-2-hydroxy-ethyl)-3-(2-trifluoromethyl-phenyl)-urea
2-Cyclopropyl-propane-1,2-diamine
$N^1$-Adamantan-2-yl-2-cyclopropyl-propane-1,2-diamine
1,$N^1$-Dicyclopropyl-ethane-1,2-diamine
$N^2$-Adamantan-2-yl-1,$N^1$-dicyclopropyl-ethane-1,2-diamine
(E/Z)-4-(2-Cyclopropyl-2-cyclopropylamino-ethylamino)-adamantan-1-ol
(E/Z)-4-(2-Amino-2-cyclopropyl-propylamino)-adamantan-1-ol
[1-(Adamantan-2-ylcarbamoyl)-1,2-dimethyl-propyl]-carbamic acid tert-butyl ester
N-Adamantan-2-yl-2-amino-2,3-dimethyl-butyramide
$N^1$-Adamantan-2-yl-2,3-dimethyl-butane-1,2-diamine
3,$N^2$-Dimethyl-butane-1,2-diamine
(E/Z)-4-(3-Methyl-2-methylamino-butylamino)-adamantan-1-ol
2-Cyclopropyl-2-cyclopropylamino-propionitrile
2,$N^2$-Dicyclopropyl-propane-1,2-diamine
$N^1$-Adamantan-2-yl-2,$N^2$-dicyclopropyl-propane-1,2-diamine
2-(Cyclopropylamino)-2-methyl-propanenitrile
$N^2$-Cyclopropyl-2-methyl-propane-1,2-diamine
(E/Z)-4-(2-Cyclopropylamino-2-methyl-propylamino)-adamantan-1-ol
$N^1$-Adamantan-2-yl-$N^2$-cyclopropyl-2-methyl-propane-1,2-diamine
2-Cyclopropyl-2-cyclopropylamino-propionitrile
2,$N^2$-Dicyclopropyl-propane-1,2-diamine
(E/Z)-4-(2-Cyclopropyl-2-cyclopropylamino-propylamino)-adamantan-1-ol
1-Aminomethyl-cyclopentylamine
(E/Z)-4-[(1-Amino-cyclopentylmethyl)-amino]-adamantan-1-ol
α-Amino-α-cyclopropyl-cyclopropaneacetonitrile
1,1-Dicyclopropyl-ethane-1,2-diamine
(E/Z)-4-(2-Amino-2,2-dicyclopropyl-ethylamino)-adamantan-1-ol
(E/Z)-4-(2-Amino-2,3-dimethyl-butylamino)-adamantan-1-ol
1-Cyclopropylamino-cyclopentanecarbonitrile
(1-Aminomethyl-cyclopentyl)-cyclopropyl-amine
(E/Z)-4-[(1-Amino-cyclopentylmethyl)-amino]-adamantan-1-ol
3-Aminomethyl-1-benzyl-piperidin-3-ylamine
(E/Z)-4-[(3-Amino-1-benzyl-piperidin-3-ylmethyl)-amino]-adamantan-1-ol and
(E/Z)-4-[(2-Amino-indan-2-ylmethyl)-amino]-adamantan-1-ol.

The compounds of formula I as described above for use as therapeutically active substance are a further embodiment of the invention.

Also an embodiment of the present invention are compounds as described above for the preparation of medicaments for the prophylaxis and therapy of illnesses which are caused by disorders associated with the enzyme 11beta-hydroxysteroid dehydrogenaseI (1bHSD1).

Likewise an embodiment of the invention are pharmaceutical compositions comprising a compound of the formula I as described above and a therapeutically inert carrier.

A further preferred embodiment of the present invention is the use of a compound of the formula I as described above for the preparation of medicaments for the treatment and prophylaxis of diabetes, obesity, eating disorders, dyslipidemiae and hypertension.

Particularly preferred is the use of a compound according to formula I as described above for the preparation of medicaments for the treatment and prophylaxis of diabetes Type II.

A further embodiment of the present invention comprises a compound according to formula I as described above, when manufactured according to any one of the described processes.

Also an embodiment of the invention is a method for the treatment and prophylaxis of diabetes, obesity, eating disorders, dyslipidemiae and hypertension, which method comprises administering an effective amount of a compound of formula I as described above.

Particularly preferred is a method for the treatment and prophylaxis of diabetes Type II, which method comprises administering an effective amount of a compound according to formula I as described above.

Assay Procedures

Transient Expression and Partial Purification:

The cDNA encoding the human 11beta-HSD1 protein was cloned into the expression vector pcDNA3 (Stratagene). This construct (for details see Alex Odermatt et al.; J Biol. Chem., 1999, Vol. 274, Issue 40, 28762-28770) was used to transiently express the protein in HEK293 cells (ATCC number: CRL-1573, described in Graham, F. L., Smiley, J., Russell, W. C., Nairn, R.; (1977)) using lipofectamine. 48 h after transfection cells were washed twice with ice-cold PBS (Phsophate buffered Saline). To 1 volume of cell suspension in PBS 2 volumes of ice-cold lysis buffer (50 mM Tris; pH7.5; 1 mM EDTA; 100 mM NaCl) were added. The cells were lysed by Potter-homogenization (20 strokes). The resulting homogenate was sonicated with a tip sonicator (10% output; 2×30 sec.) and cleared by a low speed centrifugation (10 min×9000 g; 4° C.). The microsomal fraction was collected by a high speed centrifugation (60 min×110,000 g). The resulting pellet was resuspended in storage buffer (20 mM Tris pH 7.5; 1 mM EDTA; 10% Glycerol) and the centrifugation was repeated. The resulting pellet containing the microsomal fraction was again taken up into storage buffer and aliquots were kept frozen in liquid Nitrogen until use.

Generation of Stable Cell Lines Expressing 11beta-HSD1:

The same construct used for transient expression of human 11beta-HSD1 was also used to establish cell lines stably expressing the protein. Briefly, (HEK293) cells were transfected with 11beta-HSD1 construct using the lipofectamine reagent (Gibco BRL) according to the manufacturer's instruction. Two days after transfection, geneticin selection (0.8 mg/ml) was initiated and several stable clones were isolated. One clone was further used for pharmacological characterization.

Microsome Assay

Microsomes isolated from HEK293 cells transiently expressing human 11beta-HSD1 (for details see above) were incubated in assay buffer (100 mM NaCl; 1 mM EDTA; 1 mM EGTA; 1 mM MgCl; 250 mM Sucrose; 20 mM Tris pH 7.4; Cortisone 50-200 nM and NADPH 1 mM) together with different concentrations of test substances. After 60 min. of incubation at 37° C. the assay was stopped by heating to 80° C. (5 min.) and by addition of the inhibitor Carbenoxolone (1 uM). The amount of Cortisol produced in this assay was determined using a commercially available, ELISA-based Cortisol-detection kit (Distributed by Assay Design, Inc.). Inhibitors were characterized by their IC50 values, e.g. the concentration at which the production of cortisol was 50% reduced.

In this test preferred compounds as described above have IC50 values below 1000 nM; more preferred compounds have IC50 values below 100 nM. Most preferred compounds have IC50 values below 10 nM.

Cellular Assay

To measure the effect of inhibitors in intact cells HEK293 cells stably expressing human 11beta-HSD1 (see above) were cultivated in 96 well plates in DMEM. First inhibitors and 60 min later Cortisone was added to the cells. After 60 min of incubation at 37° C. in a 5% CO2 atmosphere part of the medium was removed and the conversion from Cortisone to Cortisol was measured using a commercially available ELISA kit (Distributed by Assay Design, Inc.).

Results obtained in the microsome assay using representative compounds of the invention as the test compounds are shown in the following table:

| Compound | h 11-beta-HSD 1 $IC_{50}$ (nM) |
| --- | --- |
| Example 16 | 39 |
| Example 45 | 192 |
| Example 80 | 3 |

These results have been obtained by using the foregoing test. Compounds as described above have $IC_{50}$ values of 0.01 nM to 5000 nM; preferred compounds have $IC_{50}$ values of 0.01 nM to 100 nM. More preferred compounds have $IC_{50}$ values below 10 nM.

The compounds of formula I and their pharmaceutically acceptable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula I and their pharmaceutically acceptable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutically acceptable salts can be used for the prophylaxis and treatment of arthritis, cardiovascular diseases, diabetes, renal failure and particularly eating disorders and obesity. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

EXAMPLES

General Remarks (E/Z)-Stereochemistry in 5-hydroxy-2-amino-adamantane derivatives: Assignment of (E) stereochemistry at the 2-amino-5-hydroxyadamantane portion was confirmed by an X-ray structure of 4-cyclopropyl-1-[(E)-5-hydroxy-adamantan-2-yl]-3,4-dimethyl-imidazolidin-2-one (Example 71) and, as a consequence, also for its direct precursor 4-cyclopropyl-1-[(E)-5-hydroxy-adamantan-2-yl]-4-methyl-imidazolidin-2-one (example 69). All other assignments of (E) and (Z) stereochemistry were done in analogy with these examples. Assignments were based on the following findings: 1) During chromatographical separations of (Z) and (E) imidazolidinones, the (Z) isomer eluted first as the less polar component, followed by the (E)-isomer as the more polar component; 2) the (Z) derivative was always less active in the biological in vitro assay than the (E) derivative and 3) X-ray confirmed the (E) stereochemistry for examples 71 and 69.

Absolute configurations: Stereodescriptors for absolute configurations in final products, where given, indicate that enantiomers have been separated. However, in those cases, absolute stereochemistry has usually been assigned tentatively.

Example 1

1-Adamantan-2-yl-3-benzyl-1,3-dihydro-imidazol-2-one

Step A] (3-Adamantan-2-yl-1-benzyl-ureido)-acetic acid ethyl ester

2-Adamantyl-isocyanate (CAS 71189-14-5, made from 2-aminoadamantane according to Eur. J. Med. Chem. 28 (1), 1993, 37-45, 500 mg) and commercially available benzylamino-acetic acid ethyl ester (572 mg) were dissolved in absolute ether (25 mL) under argon and stirred at RT for 12 hours. A colorless precipitate was formed. The reaction mixture was concentrated in vacuo and the residue was triturated with hexanes (30 mL) for one hour. The suspension was filtered and the solid was dried in vacuo to give (3-adamantan-2-yl-1-benzyl-ureido)-acetic acid ethyl ester (823 mg). MS (ESI): 371.2 (MH$^+$).

Step B] 1-Adamantan-2-yl-3-benzyl-1,3-dihydro-imidazol-2-one (3-Adamantan-2-yl-1-benzyl-ureido)-acetic acid ethyl ester (450 mg) was dissolved in dry DCM (5 mL) and toluene (5 mL) under argon and cooled to −78° C. Diisobutylaluminium hydride (1 M solution in DCM, 1.46 mL) was added drop by drop over 5 minutes and the mixture was allowed to stir at −78° C. for 30 minutes. The cooling bath was removed and after 10 minutes, the reaction mixture was quenched by addition of aqueous potassium sodium tartrate solution (1M, 15 mL). The mixture was extracted with chloroform twice and the combined organic extracts were washed with brine. The combined organic layers were shaken with 25% HCl (30 mL) for 5 minutes and the layers were separated. The organic solution was dried with sodium sulfate, filtered and evaporated to give a crude product that was purified by flash chromatography using a gradient of 20% to 80% ethyl acetate in heptane as an eluent. The fractions containing the product were combined and evaporated to give 1-adamantan-2-yl-3-benzyl-1,3-dihydro-imidazol-2-one as a white solid (276 mg). MS (EI): 308.2 (M$^+$).

Example 2

1-Adamantan-2-yl-3-pyridin-2-ylmethyl-1,3-dihydro-imidazol-2-one

Step A] (3-Adamantan-2-yl-1-pyridin-2-ylmethyl-ureido)-acetic acid ethyl ester

This material was obtained in analogy to example 1, step A] from 2-adamantyl isocyanate (500 mg) and commercially available (pyridin-2-ylmethyl)amino-acetic acid ethyl ester (575 mg) as a light yellow powder (680 mg). MS (ESI): 372.1 (MH$^+$).

Step B] 1-Adamantan-2-yl-3-pyridin-2-ylmethyl-1,3-dihydro-imidazol-2-one

This material was obtained in analogy to example 1, step B] from (3-adamantan-2-yl-1-pyridin-2-ylmethyl-ureido)-acetic acid ethyl ester (350 mg) by treatment with diisobutylaluminium hydride (1.13 mL of a 1M solution in DCM). Purification of the crude material was done by flash chromatography using a gradient of 20% to 80% ethyl acetate in heptane, followed by 5% methanol in ethyl acetate and 5% methanol in ethyl acetate containing 0.5% NH$_4$OH as eluents. 1-Adamantan-2-yl-3-pyridin-2-ylmethyl-1,3-dihydro-imidazol-2-one was obtained as a light yellow solid (73 mg). MS (EI): 309.1 (M$^+$).

Example 3

1-Adamantan-2-yl-3-isopropyl-4-phenyl-1,3-dihydro-imidazol-2-one

Step A] (3-Adamantan-2-yl-1-isopropyl-ureido)-phenyl-acetic acid methyl ester

This material was obtained in analogy to example 1, step A] from 2-adamantyl isocyanate (500 mg) and isopropylamino-phenyl-acetic acid methyl ester (585 mg, CAS 78907-08-1, made from methyl-α-bromophenyl acetic acid and isopropyl amine according to J. Chem. Soc. Perkin Trans. 1, 22, 1993, 2761-2772) with the following modification: purification was achieved by flash chromatography using a gradient of 10 to 50% ethyl acetate in heptane as an eluent. (3-Adamantan-2-yl-1-isopropyl-ureido)-phenyl-acetic acid methyl ester was obtained as a light yellow liquid (948 mg). MS (EI): 385.2 (M+H$^+$).

Step B] 1-Adamantan-2-yl-3-isopropyl-4-phenyl-1,3-dihydro-imidazol-2-one

In this case, treatment of (3-adamantan-2-yl-1-isopropyl-ureido)-phenyl-acetic acid methyl ester with diisobutylaluminium hydride as described in example 1, step B] did not result in the formation of the desired material. Alternatively, (3-adamantan-2-yl-1-isopropyl-ureido)-phenyl-acetic acid methyl ester (200 mg) was dissolved in DCM (3 mL) and toluene (3 mL) under argon and treated with sodium dihydrido-bis-(2-methoxyethoxy)-aluminate (Red-Al™, 3.5 M in toluene, 0.09 mL) at −78° C. After addition of the reducing agent, the mixture was stirred at −78° C. for 30 minutes and was then allowed to warm to 0° C. The reaction mixture was quenched with 1M potassium sodium tartrate solution (10 mL) and then poured into 25% HCl (25 mL) containing a small amount of ice. The aqueous mixture was saturated with NaCl and extracted with ethyl acetate. The organic layer was separated, washed with brine, dried over Na$_2$SO$_4$, and evaporated to give a crude product. This material was subjected to flash chromatography using a gradient of 10 to 40% ethyl acetate in heptane followed by a second flash chromatography using DCM and by DCM/CH$_3$CN 9:1 as eluents. This procedure provided 3-adamantan-2-yl-1-isopropyl-5-phenyl-imidazolidine-2,4-dione (116 mg) as the major product whereas the desired material 1-adamantan-2-yl-3-isopropyl-4-phenyl-1,3-dihydro-imidazol-2-one was obtained as the minor component (colorless oil, 14 mg). MS (EI): 336.2 (M$^+$).

Example 4

1-Adamantan-2-yl-3-cyclopropyl-4-phenyl-1,3-dihydro-imidazol-2-one

Step A] Cyclopropylamino-phenyl-acetic acid methyl ester

In analogy to a procedure outlined in J. Chem. Soc. Perkin Trans. 1, 22, 1993, 2761-2772, methyl-α-bromophenylacetic acid (2.0 g) was dissolved in CH$_3$CN and cooled to 0° C. by means of an ice bath. To this solution was added triethylamine (1.7 mL) dropwise and the mixture was stirred for 30 minutes. A solution of cyclopropylamine in CH$_3$CN was then added dropwise at 0° C. over 5 minutes and stirring was continued for 2 hours. The mixture was poured into ice/water, saturated with NaCl and extracted with ethyl acetate. The organic layer was separated, washed with brine, dried over Na$_2$SO$_4$ and evaporated. The residue was purified by flash chromatography, eluting with a gradient of ethyl acetate in heptane (0 to 50% ethyl acetate). Fractions containing the product were combined and evaporated to give cyclopropylamino-phenyl-acetic acid methyl ester as a light yellow liquid (1.74 g). MS (ESI): 206.0 (MH$^+$).

Step B] (3-Adamantan-2-yl-1-cyclopropyl-ureido)-phenyl-acetic acid methyl ester

This material was obtained in analogy to example 3, step A] from 2-adamantyl isocyanate (500 mg) and cyclopropylamino-phenyl-acetic acid methyl ester (579 mg). (3-Adamantan-2-yl-1-cyclopropyl-ureido)-phenyl-acetic acid methyl ester was obtained as a colorless gum (396 mg). MS (EI): 383.3 (M+H$^+$).

Step C] 1-Adamantan-2-yl-3-cyclopropyl-4-phenyl-1,3-dihydro-imidazol-2-one

This material was obtained in analogy to example 1, step B] from (3-adamantan-2-yl-1-cyclopropyl-ureido)-phenyl-acetic acid methyl ester ester (100 mg) by treatment with diisobutylaluminium hydride (0.31 mL of a 1M solution in DCM) and conc. HCl. 1-Adamantan-2-yl-3-cyclopropyl-4-phenyl-1,3-dihydro-imidazol-2-one was obtained as a colorless gum (43 mg). MS (EI): 334.2 (M$^+$).

Example 5

1-Adamantan-2-yl-3-cyclopropyl-4-(3-fluoro-phenyl)-1,3-dihydro-imidazol-2-one

Step A] Cyclopropylamino-(3-fluoro-phenyl)-acetic acid methyl ester

This material was obtained in analogy to example 4, step A] from α-bromo-(3-fluorophenyl)-acetic acid methyl ester (1.0 g, CAS 503541-03-5, made by bromination of (3-fluorophenyl)-acetic acid methyl ester according to Tetrahedron, 58, 2002, 10113-10126) and cyclopropylamine (347 mg) to give cyclopropylamino-(3-fluoro-phenyl)-acetic acid methyl ester as a light yellow liquid (627 mg). MS (ESI): 223.9 (MH$^+$).

Step B] (3-Adamantan-2-yl-1-cyclopropyl-ureido)-(3-fluoro-phenyl)-acetic acid methyl ester This material was obtained in analogy to example 3, step A] from 2-adamantyl isocyanate (487 mg) and cyclopropylamino-(3-fluoro-phenyl)-acetic acid methyl ester (614 mg). (3-Adamantan-2-yl-1-cyclopropyl-ureido)-(3-fluoro-phenyl)-acetic acid methyl ester was obtained as a white foam (880 mg). MS (ISP): 401.5 (MH$^+$).

Step C] 1-Adamantan-2-yl-3-cyclopropyl-4-(3-fluoro-phenyl)-1,3-dihydro-imidazol-2-one This material was obtained in analogy to example 1, step B] from (3-adamantan-2-yl-1-cyclopropyl-ureido)-(3-fluoro-phenyl)-acetic acid methyl ester (520 mg) by treatment with diisobutylaluminium hydride (1.56 mL of a 1 M solution in DCM) and conc. HCl. 1-Adamantan-2-yl-3-cyclopropyl-4-(3-fluoro-phenyl)-1,3-dihydro-imidazol-2-one was obtained as a colorless gum (199 mg). MS (EI): 352.2 (M$^+$).

Example 6

1-Adamantan-2-yl-3-cyclopropyl-4-pyridin-2-yl-1,3-dihydro-imidazol-2-one

Step A] Cyclopropylamino-pyridin-2-yl-acetic acid methyl ester

This material was obtained in analogy to example 4, step A] from α-bromo-pyridin-2-yl-acetic acid methyl ester (1.0 g, CAS 52458-81-8, made by bromination of pyridine-2-yl-acetic acid methyl ester according to Tetrahedron, 58, 2002, 10113-10126) and cyclopropylamine (372 mg) to cyclopropylamino-pyridin-2-yl-acetic acid methyl ester as a light yellow liquid (515 mg). MS (ESI): 206.9 (MH$^+$).

Step B] (3-Adamantan-2-yl-1-cyclopropyl-ureido)-pyridin-2-yl-acetic acid methyl ester This material was obtained in analogy to example 3, step A] from 2-adamantyl isocyanate (715 mg) and cyclopropylamino-pyridin-2-yl-acetic acid methyl ester (370 mg). (3-Adamantan-2-yl-1-cyclopropyl-ureido)-pyridin-2-yl-acetic acid methyl ester was obtained as a yellow foam (279 mg). MS (EI): 384.3 (M+H$^+$).

Step C] 1-Adamantan-2-yl-3-cyclopropyl-4-pyridin-2-yl-1,3-dihydro-imidazol-2-one This material was obtained in analogy to example 1, step B] from (3-adamantan-2-yl-1-cyclopropyl-ureido)-pyridin-2-yl-acetic acid methyl ester (273 mg) by treatment with diisobutylaluminium hydride (0.85 mL of a 1M solution in DCM) and conc. HCl. 1-Adamantan-2-yl-3-cyclopropyl-4-pyridin-2-yl-1,3-dihydro-imidazol-2-one was obtained as a white solid (50 mg). MS (EI): 336.1 (MH$^+$).

3-Adamantan-2-yl-1-cyclopropyl-5-pyridin-2-yl-imidazolidine-2,4-dione was obtained as a side product in this reaction step (66 mg). MS (ESI): 352.2 (MH$^+$).

Example 7

1-Adamantan-2-yl-4-tert-butyl-1,3-dihydro-imidazol-2-one

Step A] (S)-2-(3-Adamantan-2-yl-ureido)-3,3-dimethyl-butyric acid methyl ester L-(+)-Methyl-tert-leucinate hydrochloride (564 mg) was dissolved in abs. DMF and then N-ethyl-diisopropylamine (0.68 mL) was added drop by drop. The mixture was allowed to stir for 30 minutes at RT and then 2-adamantyl isocyanate (500 mg) was added in one portion. Stirring was continued over night at RT. The reaction mixture was evaporated to dryness and residual DMF was removed by co-evaporation with toluene. The residue was purified by flash chromatography using 5% methanol in DCM as an eluent to give (S)-2-(3-adamantan-2-yl-ureido)-3,3-dimethyl-butyric acid methyl ester (834 mg) as a white solid. MS (EI): 322.4 (M$^+$).

Step B] 1-Adamantan-2-yl-4-tert-butyl-1,3-dihydro-imidazol-2-one

This material was obtained in analogy to example 1, step B] from (S)-2-(3-adamantan-2-yl-ureido)-3,3-dimethyl-butyric acid methyl ester (400 mg) by treatment with diisobutylaluminium hydride (1.49 mL of a 1M solution in DCM) and conc. HCl. 1-Adamantan-2-yl-4-tert-butyl-1,3-dihydro-imidazol-2-one was obtained as a white solid (80 mg). MS (EI): 274.3 (M$^+$).

Example 8

1-Adamantan-2-yl-4-isopropyl-1,3-dihydro-imidazol-2-one

Step A] 2-(3-Adamantan-2-yl-ureido)-3-methyl-butyric acid methyl ester

This material was obtained in analogy to example 7, step A] from D,L-valine methyl ester hydrochloride (416 mg) and 2-adamantyl isocyanate (400 mg). 2-(3-Adamantan-2-yl-ureido)-3-methyl-butyric acid methyl ester was isolated as a white solid (773 mg). MS (ESI): 309.3 (MH$^+$).

Step B] 1-Adamantan-2-yl-4-isopropyl-1,3-dihydro-imidazol-2-one

This material was obtained in analogy to example 1, step B] from 2-(3-adamantan-2-yl-ureido)-3-methyl-butyric acid methyl ester (400 mg) by treatment with diisobutylaluminium hydride (1.56 mL of a 1M solution in DCM) and conc. HCl. 1-Adamantan-2-yl-4-isopropyl-1,3-dihydro-imidazol-2-one was obtained as a white solid (166 mg). MS (EI): 260.3 (M$^+$).

Example 9

1-Adamantan-2-yl-4-phenyl-1,3-dihydro-imidazol-2-one

Step A] (3-Adamantan-2-yl-ureido)-phenyl-acetic acid methyl ester

This material was obtained in analogy to example 7, step A] from (S)-(+)-phenylglycine methyl ester hydrochloride (478 mg) and 2-adamantyl isocyanate (400 mg) as a light yellow semi-solid (852 mg). MS (ESI): 343.1 (MH$^+$).

Step B] 1-Adamantan-2-yl-4-phenyl-1,3-dihydro-imidazol-2-one

This material was obtained in analogy to example 1, step B] from (3-adamantan-2-yl-ureido)-phenyl-acetic acid methyl ester (480 mg) by treatment with diisobutylaluminium hydride (1.68 mL of a 1M solution in DCM) and conc. HCl as a white solid (30 mg). MS (ESI): 295.3 (MH$^+$).

Example 10

1-Adamantan-2-yl-4-isobutyl-1,3-dihydro-imidazol-2-one

Step A] (S)-2-(3-Adamantan-2-yl-ureido)-4-methyl-pentanoic acid methyl ester

This material was obtained in analogy to example 7, step A] from L-leucine methyl ester hydrochloride (430 mg) and 2-adamantyl isocyanate (400 mg) as a light yellow semi-solid (902 mg). MS (ESI): 323.5 (MH$^+$).

Step B] 1-Adamantan-2-yl-4-isobutyl-1,3-dihydro-imidazol-2-one

This material was obtained in analogy to example 1, step B] from (S)-2-(3-adamantan-2-yl-ureido)-4-methyl-pentanoic acid methyl ester (893 mg) by treatment with diisobutylaluminium hydride (3.32 mL of a 1M solution in DCM) and conc. HCl as a light yellow solid (93 mg). MS (EI): 274.2 (M$^+$).

Example 11

1-Adamantan-2-yl-4-(3-fluoro-benzyl)-1,3-dihydro-imidazol-2-one

Step A] (R)-2-(3-Adamantan-2-yl-ureido)-3-(3-fluoro-phenyl)-propionic acid methyl ester This material was obtained in analogy to example 7, step A] from meta-fluoro-D-phenylalanine methyl ester hydrochloride (554 mg) and 2-adamantyl isocyanate (400 mg) as a light yellow solid (784 mg). MS (ESI): 375.4 (MH$^+$).

Step B] 1-Adamantan-2-yl-4-(3-fluoro-benzyl)-1,3-dihydro-imidazol-2-one

This material was obtained in analogy to example 1, step B] from (R)-2-(3-adamantan-2-yl-ureido)-3-(3-fluoro-phenyl)-propionic acid methyl ester (780 mg) by treatment with diisobutylaluminium hydride (2.5 mL of a 1M solution in DCM) and conc. HCl as a light yellow solid (220 mg). MS (EI): 326.3 (M$^+$).

Example 12

1-Adamantan-2-yl-4-[(S)-sec-butyl]-1,3-dihydro-imidazol-2-one

Step A] (2S,3S)-2-(3-Adamantan-2-yl-ureido)-3-methyl-pentanoic acid methyl ester This material was obtained in analogy to example 7, step A] from L-isoleucine methyl ester hydrochloride (410 mg) and 2-adamantyl isocyanate (400 mg) as a light yellow liquid (945 mg). MS (ISP): 323.4 (MH$^+$).

Step B] 1-Adamantan-2-yl-4-[(S)-sec-butyl]-1,3-dihydro-imidazol-2-one

This material was obtained in analogy to example 1, step B] from (2S,3S)-2-(3-adamantan-2-yl-ureido)-3-methyl-pentanoic acid methyl ester (290 mg) by treatment with diisobutylaluminium hydride (1.08 mL of a 1M solution in DCM) and conc. HCl as a white solid (78 mg). MS (EI): 274.3 (M$^+$).

Example 13

1-Adamantan-2-yl-4-(2,2-dimethyl-propyl)-1,3-dihydro-imidazol-2-one

Step A] H-beta-tert-butyl-D,L-alanine methyl ester hydrochloride

Thionylchloride (2.0 mL) was added drop by drop to methanol (23 mL) under argon with cooling by means of an ice/methanol bath (−10° C.). After 5 minutes, H-beta-tert-butyl-D,L-alanine (2.0 g) was added in one portion. The mixture was heated to reflux and kept at this temperature over night. It was then cooled to RT and evaporated in vacuo. The residue was triturated with ethyl acetate/hexanes 2:8 for 1 hour and then filtered. The resulting white solid was dried in vacuo to afford H-beta-tert-butyl-D,L-alanine methyl ester hydrochloride (1.81 g). MS (ESI): 160.3 (MH$^+$, free base).

Step B] 2-(3-Adamantan-2-yl-ureido)-4,4-dimethyl-pentanoic acid methyl ester

This material was obtained in analogy to example 7, step A] from H-beta-tert-butyl-D,L-alanine methyl ester hydrochloride (552 mg) and 2-adamantyl isocyanate (500 mg) as a light yellow foam (814 mg). MS (ISP): 337.4 (MH$^+$).

Step C] 1-Adamantan-2-yl-4-(2,2-dimethyl-propyl)-1,3-dihydro-imidazol-2-one

This material was obtained in analogy to example 1, step B] from 2-(3-adamantan-2-yl-ureido)-4,4-dimethyl-pentanoic acid methyl ester (798 mg) by treatment with diisobutylaluminium hydride (2.85 mL of a 1M solution in DCM) and conc. HCl as a white solid (227 mg). MS (EI): 288.3 (M$^+$).

Example 14

1-Adamantan-2-yl-4-cyclohexyl-1,3-dihydro-imidazol-2-one

Step A] D,L-Cyclohexylglycine methyl ester hydrochloride

This known material (CAS 322392-74-5) was obtained in analogy to example 13, step A] from D,L-cyclohexyl glycine (552 mg) by treatment with SOCl$_2$ in methanol as a white powder (1.46 g). MS (ISP): 172.4 (MH$^+$, free base).

Step B] (3-Adamantan-2-yl-ureido)-cyclohexyl-acetic acid methyl ester

This material was obtained in analogy to example 7, step A] from D,L-cyclohexylglycine methyl ester hydrochloride (527 mg) and 2-adamantyl isocyanate (450 mg) as a white foam (866 mg). MS (ESI): 349.3 (MH$^+$).

Step C] 1-Adamantan-2-yl-4-cyclohexyl-1,3-dihydro-imidazol-2-one

This material was obtained in analogy to example 1, step B] from (3-adamantan-2-yl-ureido)-cyclohexyl-acetic acid methyl ester (859 mg) by treatment with diisobutylaluminium hydride (2.96 mL of a 1M solution in DCM) and conc. HCl as a white solid (44 mg). MS (ESI): 301.1 (MH$^+$).

Example 15

1-Adamantan-2-yl-4-cyclopropyl-1,3-dihydro-imidazol-2-one

Step A] L-Cyclopropylglycine methyl ester hydrochloride

This known material (CAS 138326-68-8) was obtained in analogy to example 13, step A] from L-cyclopropylglycine (500 mg) by treatment with SOCl$_2$ in methanol as a white solid (614 mg). MS (ESI): 259.1 (2M+H$^+$, free base).

Step B] (S)-(3-Adamantan-2-yl-ureido)-cyclopropyl-acetic acid methyl ester

This material was obtained in analogy to example 7, step A] from L-cyclopropylglycine methyl ester hydrochloride (650 mg) and 2-adamantyl isocyanate (607 mg) as a white solid (987 mg). MS (ESI): 307.2 (MH$^+$).

Step C] 1-Adamantan-2-yl-4-cyclopropyl-1,3-dihydro-imidazol-2-one

This material was obtained in analogy to example 1, step B] from (S)-(3-adamantan-2-yl-ureido)-cyclopropyl-acetic acid methyl ester (978 mg) by treatment with diisobutylaluminium hydride (3.83 mL of a 1M solution in DCM) and conc. HCl as a light yellow solid (282 mg). MS (ESI): 259.0 (MH$^+$).

Example 16

1-Adamantan-2-yl-4-(2,2,2-trifluoro-ethyl)-1,3-dihydro-imidazol-2-one

Step A] 2-Amino-4,4,4-trifluoro-butyric acid methyl ester hydrochloride

This material (which is known as the free base; CAS 188010-09-5) was obtained in analogy to example 13, step A] from 2-amino-4,4,4-trifluoro-butyric acid (2.0 g) by treatment with SOCl$_2$ in methanol as a white solid (2.38 g). MS (ESI): 172.1 (MH$^+$, free base).

Step B] 2-(3-Adamantan-2-yl-ureido)-4,4,4-trifluoro-butyric acid methyl ester

This material was obtained in analogy to example 7, step A] from 2-amino-4,4,4-trifluoro-butyric acid methyl ester hydrochloride (586 mg) and 2-adamantyl isocyanate (500 mg) as a white solid (854 mg). MS (ESI): 349.4 (MH$^+$).

Step C] 1-Adamantan-2-yl-4-(2,2,2-trifluoro-ethyl)-1,3-dihydro-imidazol-2-one

This material was obtained in analogy to example 1, step B] from 2-(3-adamantan-2-yl-ureido)-4,4,4-trifluoro-butyric acid methyl ester (855 mg) by treatment with diisobutylaluminium hydride (2.95 mL of a 1M solution in DCM) and conc. HCl as a light yellow solid (345 mg). MS (ESI): 301.1 (MH$^+$).

Example 17

1-Adamantan-2-yl-4-cyclopropylmethyl-1,3-dihydro-imidazol-2-one

Step A] (S)-2-Amino-3-cyclopropyl-propionic acid methyl ester hydrochloride

This known material (CAS 206438-31-5) was obtained in analogy to example 13, step A] from (S)-2-amino-3-cyclopropyl-propionic acid (1.0 g) by treatment with SOCl$_2$ in methanol as a white solid (1.34 g). MS (ESI): 144.1 (MH$^+$, free base).

Step B] (S)-2-(3-Adamantan-2-yl-ureido)-3-cyclopropyl-propionic acid methyl ester This material was obtained in analogy to example 7, step A] from (S)-2-amino-3-cyclopropyl-propionic acid methyl ester hydrochloride (608 mg) and 2-adamantyl isocyanate (600 mg) as a light yellow solid (994 mg). MS (EI): 320.2 (M$^+$).

Step C] 1-Adamantan-2-yl-4-cyclopropylmethyl-1,3-dihydro-imidazol-2-one

This material was obtained in analogy to example 1, step B] from (S)-2-(3-adamantan-2-yl-ureido)-3-cyclopropyl-propionic acid methyl ester (992 mg) by treatment with diisobutylaluminium hydride (3.71 mL of a 1M solution in DCM) and conc. HCl as a pink solid (183 mg). MS (ESI): 273.0 (MH$^+$).

Example 18

4-Isobutyl-1-(2-trifluoromethyl-phenyl)-1,3-dihydro-imidazol-2-one

Step A] (S)-4-Methyl-2-[3-(2-trifluoromethyl-phenyl)-ureido]-pentanoic acid methyl ester This material was obtained in analogy to example 7, step A] from L-leucine methyl ester hydrochloride (340 mg) and 2-trifluoromethylphenylisocyanate (350 mg) as a colorless solid (586 mg). MS (ESI): 333.3 (MH$^+$).

Step B] 4-Isobutyl-1-(2-trifluoromethyl-phenyl)-1,3-dihydro-imidazol-2-one

This material was obtained in analogy to example 1, step B] from (S)-4-methyl-2-[3-(2-trifluoromethyl-phenyl)-ureido]-pentanoic acid methyl ester (586 mg) by treatment with diisobutylaluminium hydride (2.11 mL of a 1M solution in DCM) and conc. HCl as a colorless solid (134 mg). MS (ESI): 285.3 (MH$^+$).

Example 19

4-Isopropyl-1-(2-trifluoromethyl-phenyl)-1,3-dihydro-imidazol-2-one

Step A] 3-Methyl-2-[3-(2-trifluoromethyl-phenyl)-ureido]-butyric acid methyl ester ester This material was obtained in analogy to example 7, step A] from D,L-valine methyl ester hydrochloride (314 mg) and 2-trifluoromethylphenylisocyanate (350 mg) as a colorless solid (537 mg). MS (ESI): 319.0 (MH$^+$).

Step B] 4-Isopropyl-1-(2-trifluoromethyl-phenyl)-1,3-dihydro-imidazol-2-one This material was obtained in analogy to example 1, step B] from 3-methyl-2-[3-(2-trifluoromethyl-phenyl)-ureido]-butyric acid methyl ester (537 mg) by treatment with diisobutylaluminium hydride (2.02 mL of a 1M solution in DCM) and conc. HCl as a colorless solid (123 mg). MS (ESI): 271.3 (MH$^+$).

Example 20

1-Adamantan-1-yl-4-isobutyl-1,3-dihydro-imidazol-2-one

Step A] (S)-2-(3-Adamantan-1-yl-ureido)-4-methyl-pentanoic acid methyl ester This material was obtained in analogy to example 7, step A] from L-leucine methyl ester hydrochloride (340 mg) and 1-adamantylisocyanate (331 mg) as a colorless solid (564 mg). MS (ESI): 323.3 (MH$^+$).

Step B] 1-Adamantan-1-yl-4-isobutyl-1,3-dihydro-imidazol-2-one

This material was obtained in analogy to example 1, step B] from (S)-2-(3-adamantan-1-yl-ureido)-4-methyl-pentanoic acid methyl ester (564 mg) by treatment with diisobutylaluminium hydride (2.10 mL of a 1M solution in DCM) and conc. HCl as a colorless solid (74 mg). MS (ESI): 275.3 (MH$^+$).

Example 21

1-Adamantan-1-yl-4-isopropyl-1,3-dihydro-imidazol-2-one

Step A] 2-(3-Adamantan-1-yl-ureido)-3-methyl-butyric acid methyl ester

This material was obtained in analogy to example 7, step A] from D,L-valine methyl ester hydrochloride (390 mg) and 1-adamantylisocyanate (300 mg) as a colorless solid (424 mg). MS (ESI): 309.4 (MH$^+$).

Step B] 1-Adamantan-1-yl-4-isopropyl-1,3-dihydro-imidazol-2-one

This material was obtained in analogy to example 1, step B] from 2-(3-adamantan-1-yl-ureido)-3-methyl-butyric acid methyl ester (424 mg) by treatment with diisobutylaluminium hydride (1.65 mL of a 1M solution in DCM) and conc. HCl as a colorless solid (24 mg). MS (ESI): 261.3 (MH$^+$).

Example 22

1-(1R,2S,4S/1S, 2R,4R)-Bicyclo[2.2.1]hept-2-yl-4-tert-butyl-1,3-dihydro-imidazol-2-one

Step A] (S)-2-((1R,2S,4S/1S, 2R,4R)-3-Bicyclo[2.2.1]hept-2-ylureido)-3,3-dimethyl-butyric acid methyl ester (1:1 mixture of 2 diastereomers)

This material was obtained in analogy to example 7, step A] from L-(+)-methyl-tert-leucinate hydrochloride (390 mg) and known (+/−)-endo-2-isocyanato-bicyclo[2.2.1]heptane (CAS 57561-64-5, made from (+/−)-endo-2-norbornylamine hydrochloride according to Eur. J. Med. Chem. 28 (1), 1993, 37-45, 237 mg) as a light yellow (417 mg). MS (ESI): 383.4 (MH$^+$).

Step B] 1-(1R,2S,4S/1S, 2R,4R)-Bicyclo[2.2.1]hept-2-yl-4-tert-butyl-1,3-dihydro-imidazol-2-one This material was obtained in analogy to example 1, step B] from (S)-2-(endo-3-bicyclo[2.2.1]hept-2-ylureido)-3,3-dimethyl-butyric acid methyl ester (408 mg) by treatment with diisobutylaluminium hydride (1.73 mL of a 1M solution in DCM) and conc. HCl as a colorless solid (30 mg). MS (EI): 234.2 (M$^+$).

Example 23

1-Adamantan-2-yl-3-cyclopropylmethyl-4-isopropyl-1,3-dihydro-imidazol-2-one

1-Adamantan-2-yl-4-isopropyl-1,3-dihydro-imidazol-2-one (obtained in example 8, 100 mg) was dissolved in dry DMF under argon and sodium hydride (55% in mineral oil) was added. The mixture was allowed to stir for 45 minutes and then bromomethylcyclopropane (0.04 ml) was added drop by drop. Stirring was continued at RT for another 4 hours. The reaction mixture was poured into ice/water, saturated with NaCl and extracted with ethyl acetate. The organic layer was washed with brine, dried over $Na_2SO_4$ and evaporated to give a residue that was purified by flash chromatography using a gradient of 10 to 80% ethyl acetate in heptane as an eluent. Fractions containing the desired material were combined and evaporated to give 1-adamantan-2-yl-3-cyclopropylmethyl-4-isopropyl-1,3-dihydro-imidazol-2-one as a colorless oil (87 mg). MS (ESI): 315.2 ($MH^+$).

Example 24

1-Adamantan-2-yl-4-isopropyl-3-pyridin-2-ylmethyl-1,3-dihydro-imidazol-2-one

1—This material was obtained as described in example 23 from 1-adamantan-2-yl-4-isopropyl-1,3-dihydro-imidazol-2-one (obtained in example 8, 100 mg) by alkylation with 2-chloromethylpyridine hydrochloride (73 mg) with the following modification: 2.5 equivalents of NaH dispersion (42 mg) was used such as to compensate for the HCl content in the alkylating agent. 1-Adamantan-2-yl-4-isopropyl-3-pyridin-2-ylmethyl-1,3-dihydro-imidazol-2-one was obtained as a light yellow gum (64 mg). MS (ESI): 352.2 ($MH^+$).

Example 25

1-Adamantan-2-yl-3-cyclopropyl-4-isopropyl-1,3-dihydro-imidazol-2-one

Step A] 2-Cyclopropylamino-3-methyl-butyric acid ethyl ester

In analogy to a procedure outlined in J. Org. Chem. 46 (26), 1981, 5445-5447, ethyl 2-bromoisovaleriate (2.0 g) was dissolved in $CH_3CN$ (10 mL). To this solution were added cyclopropyl amine (0.74 mL) and triethyl amine (1.46 mL) and the resulting mixture was heated to reflux for 20 hours. It was then cooled to RT and evaporated in vacuo. The residue was dissolved in ethyl acetate (100 mL) and the organic layer was extracted with 2M HCl twice. The aqueous extracts were combined and made basic (pH 10 to 11) with conc. NaOH, followed by extraction with ethyl acetate. The organic layer was separated, washed with brine, dried over $Na_2SO_4$ and evaporated to give 2-cyclopropylamino-3-methyl-butyric acid ethyl ester that was used without further purification (209 mg). MS (ISP): 186.4 ($MH^+$).

Step B] 2-(3-Adamantan-2-yl-1-cyclopropyl-ureido)-3-methyl-butyric acid ethyl ester This material was obtained in analogy to example 7, step A] from 2-cyclopropylamino-3-methyl-butyric acid ethyl ester (198 mg) and 2-adamantyl isocyanate (189 mg) with the following modification: the reaction was carried out at 60° C. for 12 hours. 2-(3-Adamantan-2-yl-1-cyclopropyl-ureido)-3-methyl-butyric acid ethyl ester was obtained as a light brown solid (241 mg). MS (ESI): 363.2 ($MH^+$).

Step C] 1-Adamantan-2-yl-3-cyclopropyl-4-isopropyl-1,3-dihydro-imidazol-2-one 2-(3-Adamantan-2-yl-1-cyclopropyl-ureido)-3-methyl-butyric acid ethyl ester (110 mg) was dissolved in ethanol (5 mL) under argon and then sodium borohydride (92 mg) was added in one portion. The mixture was heated to 55° C. and stirred over night. TLC analysis confirmed complete consumption of the starting material. The mixture was concentrated in vacuo and the residue was dissolved in ethyl acetate and was then vigorously shaken with 25% HCl. The organic layer was separated, washed with brine, dried over $Na_2SO_4$ and evaporated to dryness. The residue was purified by flash chromatography: a first column was eluted with a gradient of methanol in DCM (0 to 5%) and a second column with a gradient of 0 to 10% methanol in $DCM/CH_3CN$ (85:15). 1-Adamantan-2-yl-3-cyclopropyl-4-isopropyl-1,3-dihydro-imidazol-2-one was obtained as a colorless oil (23 mg). MS (ESI): 301.4 ($MH^+$).

Example 26

1-Adamantan-2-yl-3-cyclobutylmethyl-4-isopropyl-1,3-dihydro-imidazol-2-one

This material was obtained in analogy to the procedure outlined in example 23 from 1-adamantan-2-yl-4-isopropyl-1,3-dihydro-imidazol-2-one (obtained in example 8, 100 mg) by alkylation with bromomethylcyclobutane (86 mg). 1-Adamantan-2-yl-3-cyclobutylmethyl-4-isopropyl-1,3-dihydro-imidazol-2-one was obtained as a light yellow oil (51 mg). MS (EI): 328.3 ($M^+$).

Example 27

1-Adamantan-2-yl-4-cyclopropyl-3-cyclopropylmethyl-1,3-dihydro-imidazol-2-one

This material was obtained in analogy to the procedure outlined in example 23 from 1-adamantan-2-yl-4-cyclopropyl-1,3-dihydro-imidazol-2-one (obtained in example 15, 100 mg) by alkylation with bromomethylcyclopropane (57 mg). 1-Adamantan-2-yl-4-cyclopropyl-3-cyclopropylmethyl-1,3-dihydro-imidazol-2-one was obtained as a light yellow oil (11 mg). MS (EI): 312.3 ($M^+$).

Example 28

3-Cyclopropyl-1-(5-fluoro-2-trifluoromethyl-benzyl)-4-methyl-1,3-dihydro-imidazol-2-one Step A]
1-Cyclopropyl-5-methyl-1,3-dihydro-imidazol-2-one Chloroacetone (2.0 g), potassium cyanate (1.84 g) and cyclopropylamine (6.17 g) were dissolved or suspended in DMF (25 mL) and heated to 50° C. over night. The appearance of the suspension changed and on the second day a fine precipitate was observed. The suspension was concentrated in vacuo and the residue was treated with 25% HCl (25 mL) and DCM (50 mL) for one hour with vigorous stirring. The layers were separated and the organic phase was washed with brine, dried over $Na_2SO_4$ and evaporated. The residue was purified by flash chromatography using a gradient of methanol in ethyl acetate (0 to 5%) as an eluent to give 1-cyclopropyl-5-methyl-1,3-dihydro-imidazol-2-one as colorless solid (1.05 g). $^1$H-NMR (δ, $CDCl_3$): 9.80 (br s, 1H), 5.79 (d, J=1.2 Hz, 1H), 2.91 (m, 1H), 2.012 (d, J=1.2 Hz, 3H), 0.92-0.84 (m, 2H), 0.82-0.77 (m, 2H).

Step B] 3-Cyclopropyl-1-(5-fluoro-2-trifluoromethyl-benzyl)-4-methyl-1,3-dihydro-imidazol-2-one Cyclopropyl-5-methyl-1,3-dihydro-imidazol-2-one (150 mg) was dissolved in DMF (5 mL) under argon and sodium hydride (55% in mineral oil, 71 mg) was added in one portion.

The mixture was stirred until gas evolution stopped (approx. 20 minutes) and then a solution of 2-trifluoromethyl-5-fluorobenzyl bromide (307 mg) in DMF (2 mL) was added over 5 minutes. Stirring was continued for 1 hour and then the reaction mixture was poured into brine. The aqueous solution was extracted with ethyl acetate and the organic layer was separated and washed with brine. The combined organic extracts were dried over $Na_2SO_4$ and evaporated. Residual DMF was removed by co-evaporation with toluene. The crude material was purified by flash chromatography using a gradient of 20 to 50% ethyl acetate in heptane as an eluent. Fractions containing the desired product were combined and evaporated to give 3-cyclopropyl-1-(5-fluoro-2-trifluoromethyl-benzyl)-4-methyl-1,3-dihydro-imidazol-2-one as a colorless oil (201 mg). MS (ESI): 315.1 ($MH^+$).

Example 29

3-Cyclopropyl-4-methyl-1-(2-trifluoromethyl-benzyl)-1,3-dihydro-imidazol-2-one

This material was obtained in analogy to the procedure outlined in example 28, Step B] from 1-cyclopropyl-5-methyl-1,3-dihydro-imidazol-2-one (obtained in example 28, step A), 150 mg) by alkylation with 2-trifluoromethylbenzyl bromide (285 mg). 3-Cyclopropyl-4-methyl-1-(2-trifluoromethyl-benzyl)-1,3-dihydro-imidazol-2-one was obtained as a colorless liquid (121 mg). MS (ESI): 297.1 ($MH^+$).

Example 30

1-[1-(4-Chloro-phenyl)-cyclopropyl]-4-isopropyl-1,3-dihydro-imidazol-2-one

Step A]: 2-{3-[1-(4-Chloro-phenyl)-cyclopropyl]-ureido}-3-methyl-butyric acid methyl ester To a suspension of 1-(4-Chlorophenyl)-1-cyclopropane carboxylic acid (400 mg) in benzene (8 mL) was added triethylamine (0.23 mL) and diphenylphosphoryl azide (0.44 mL) over 5 minutes under argon. The mixture was the allowed to stir at 90° C. for 2 hours. D,L-valine methyl ester hydrochloride was added in one portion and stirring was continued at 90° C. for 20 hours. The mixture was cooled and added to ethyl acetate and 1 M NaOH. The layers were separated and the organic phase was washed with brine, dried over $Na_2SO_4$ and evaporated. The residue was purified by flash chromatography using methanol/ethyl acetate 9:1 as an eluent. Fractions containing the desired material were combined and evaporated to give 2-{3-[1-(4-chloro-phenyl)-cyclopropyl]-ureido}-3-methyl-butyric acid methyl ester as colorless solid (500 mg). MS (ESI): 325.2 ($MH^+$).

Step B] 1-[1-(4-Chloro-phenyl)-cyclopropyl]-4-isopropyl-1,3-dihydro-imidazol-2-one This material was obtained in analogy to example 1, step B] from 2-{3-[1-(4-chloro-phenyl)-cyclopropyl]-ureido}-3-methyl-butyric acid methyl ester (500 mg) by treatment with diisobutylaluminium hydride (1.85 mL of a 1M solution in DCM) and conc. HCl as a colorless solid (20 mg). MS (ESI): 277.2 ($MH^+$).

Example 31

1-Adamantan-2-yl-4-benzyl-5-isopropyl-1,3-dihydro-imidazol-2-one

Step A] 1-Adamantan-2-yl-3-(1-benzyl-3-methyl-2-oxo-butyl)-urea

This material was obtained in analogy to example 7, step A] from known 2-amino-4-methyl-1-phenyl-pentan-3-one hydrochloride (CAS 472995-82-7, see J. Heterocyclic Chem. 39 (2), 2002, 375-382, 249 mg) and 2-adamantyl isocyanate (194 mg). 1-Adamantan-2-yl-3-(1-benzyl-3-methyl-2-oxobutyl)-urea was obtained as a white solid (245 mg). MS (ISP): 369.5 ($MH^+$).

Step B] 1-Adamantan-2-yl-4-benzyl-5-isopropyl-1,3-dihydro-imidazol-2-one

Adamantan-2-yl-3-(1-benzyl-3-methyl-2-oxo-butyl)-urea (100 mg) was dissolved in dry THF (2 mL) and treated with 25% HCl (5 mL) at 60° C. for 3.5 hours. The mixture was cooled, poured into ice cold 3M NaOH, saturated with NaCl. The mixture was extracted with ethyl acetate and the organic layer was separated, washed with brine, dried over $Na_2SO_4$ and evaporated. The residue was purified by flash chromatography using a gradient of 10 to 40% ethyl acetate in heptane as an eluent. Fractions containing the desired material were combined and evaporated to give 1-adamantan-2-yl-4-benzyl-5-isopropyl-1,3-dihydro-imidazol-2-one as a white foam (18 mg). MS (EI): 350.3 ($M^+$).

Example 32

1-Adamantan-2-yl-3-methyl-4-(2,2,2-trifluoro-ethyl)-1,3-dihydro-imidazol-2-one

This material was obtained in analogy to the procedure outlined in example 23 from 1-adamantan-2-yl-4-(2,2,2-trifluoro-ethyl)-1,3-dihydro-imidazol-2-one (obtained in example 16, 100 mg) by alkylation with iodomethane (71 mg). 1-Adamantan-2-yl-3-methyl-4-(2,2,2-trifluoro-ethyl)-1,3-dihydro-imidazol-2-one was obtained as a light yellow solid (72 mg). MS (EI): 314.2 ($M^+$).

Example 33

1-Adamantan-2-yl-3-cyclopropylmethyl-4-(2,2,2-trifluoro-ethyl)-1,3-dihydro-imidazol-2-one This material was obtained in analogy to the procedure outlined in example 23 from 1-adamantan-2-yl-4-(2,2,2-trifluoro-ethyl)-1,3-dihydro-imidazol-2-one (obtained in example 16, 100 mg) by alkylation with bromomethylcyclopropane (67 mg). 1-Adamantan-2-yl-3-cyclopropylmethyl-4-(2,2,2-trifluoro-ethyl)-1,3-dihydro-imidazol-2-one was obtained as a light yellow solid (72 mg). MS (EI): 354.2 ($M^+$).

Example 34

1-Adamantan-2-yl-4-cyclopropyl-3-methyl-1,3-dihydro-imidazol-2-one

This material was obtained in analogy to the procedure outlined in example 23 from 1-adamantan-2-yl-4-cyclopropyl-1,3-dihydro-imidazol-2-one (obtained in example 15, 100 mg) by alkylation with iodomethane (82 mg). 1-Adamantan-2-yl-4-cyclopropyl-3-methyl-1,3-dihydro-imidazol-2-one was obtained as a light yellow oil (52 mg). MS (EI): 272.3 (M⁺).

Example 35

3-Cyclopropylmethyl-4-isopropyl-1-(2-trifluoromethyl-phenyl)-1,3-dihydro-imidazol-2-one This material was obtained in analogy to the procedure outlined in example 23 from 4-isopropyl-1-(2-trifluoromethyl-phenyl)-1,3-dihydro-imidazol-2-one (obtained in example 19, 50 mg) by alkylation with bromomethylcyclopropane (25 mg). 3-Cyclopropylmethyl-4-isopropyl-1-(2-trifluoromethyl-phenyl)-1,3-dihydro-imidazol-2-one was obtained as a colorless oil (11 mg). MS (ESI): 325.3 (MH⁺).

Example 36

3-Cyclopropylmethyl-4-isobutyl-1-(2-trifluoromethyl-phenyl)-1,3-dihydro-imidazol-2-one This material was obtained in analogy to the procedure outlined in example 23 from 4-isobutyl-1-(2-trifluoromethyl-phenyl)-1,3-dihydro-imidazol-2-one (obtained in example 18, 200 mg) by alkylation with bromomethylcyclopropane (105 mg). 3-Cyclopropylmethyl-4-isobutyl-1-(2-trifluoromethyl-phenyl)-1,3-dihydro-imidazol-2-one was obtained as a light yellow oil (72 mg). MS (ESI): 339.2 (MH⁺).

Example 37

4-Isobutyl-5-(2,2,2-trifluoro-ethyl)-1-(2-trifluoromethyl-phenyl)-1,3-dihydro-imidazol-2-one This material was obtained in analogy to the procedure outlined in example 23 from 4-isobutyl-1-(2-trifluoromethyl-phenyl)-1,3-dihydro-imidazol-2-one (obtained in example 18, 200 mg) by alkylation with 2,2,2-trifluoroethyl iodide (162 mg). In contrast to the other, similar reactions, alkylation occurred predominantly at C-5 instead of N-3 of the imidazolone core. Thus, this reaction yielded 4-isobutyl-5-(2,2,2-trifluoro-ethyl)-1-(2-trifluoromethyl-phenyl)-1,3-dihydro-imidazol-2-one as a light yellow solid (36 mg). MS (ESI): 367.0 (MH⁺).

Example 38

4-Isobutyl-3-methyl-1-(2-trifluoromethyl-phenyl)-1,3-dihydro-imidazol-2-one

This material was obtained in analogy to the procedure outlined in example 23 from 4-isobutyl-1-(2-trifluoromethyl-phenyl)-1,3-dihydro-imidazol-2-one (obtained in example 18, 200 mg) by alkylation with iodomethane (110 mg). 4-Isobutyl-3-methyl-1-(2-trifluoromethyl-phenyl)-1,3-dihydro-imidazol-2-one was obtained as a colorless oil (140 mg). MS (ESI): 299.2 (MH⁺).

Example 39

3-Cyclobutylmethyl-4-isobutyl-1-(2-trifluoromethyl-phenyl)-1,3-dihydro-imidazol-2-one This material was obtained in analogy to the procedure outlined in example 23 from 4-isobutyl-1-(2-trifluoromethyl-phenyl)-1,3-dihydro-imidazol-2-one (obtained in example 18, 200 mg) by alkylation with bromomethylcyclobutane (115 mg). 3-Cyclobutylmethyl-4-isobutyl-1-(2-trifluoromethyl-phenyl)-1,3-dihydro-imidazol-2-one was obtained as a light yellow oil (9 mg). MS (ESI): 353.2 (MH⁺).

Example 40

1-[(Z)-5-hydroxy-adamantan-2-yl]-4-isobutyl-1,3-dihydro-imidazol-2-one

Step A]: (E,Z)-2-Amino-5-hydroxyadamantane

This know material (CAS 62058-13-3) was made according to Klimova et al., Khimiko-Farmatsevticheskii Zhurnal (1986), 20(7), 810-815 by hydroxylation of 2-aminoadamantane with $HNO_3$ in $H_2SO_4$. 2-amino-5-hydroxyadamantane was obtained as a 2:1 mixture of the (Z) and (E) diasteromers.

Step B] (S)-2-[3-[(E)-5-hydroxy-adamantan-2-yl]-ureido]-4-methyl-pentanoic acid methyl ester and (S)-2-[3-[(Z)-5-hydroxy-adamantan-2-yl]-ureido]-4-methyl-pentanoic acid methyl ester This material was obtained in analogy to example 7, step A] from (E,Z)-2-amino-5-hydroxyadamantane (500 mg) and (S)-(−)-2-isocycanaoto-4-methylvaleric acid methyl ester (1.02 g). (S)-2-[3-((E/Z)-5-Hydroxy-adamantan-2-yl)-ureido]-4-methyl-pentanoic acid methyl ester was obtained as a mixture of 2 diasteromers as a light brown foam (966 mg). MS (ESI): 339.1 (MH⁺).

A fraction of this material (245 mg) was subjected to preparative HPLC (normal phase silica, heptane/ethanol 80:20) to give (S)-2-[3-[(Z)-5-hydroxy-adamantan-2-yl]-ureido]-4-methyl-pentanoic acid methyl ester (103 mg, white solid, MS (ESI): 339.1 (MH⁺)) and (S)-2-[3-[(E)-5-hydroxy-adamantan-2-yl]-ureido]-4-methyl-pentanoic acid methyl ester (56 mg, white solid, MS (ESI): 339.3 (MH⁺))

Step C]: 1-[(Z)-5-hydroxy-adamantan-2-yl]-4-isobutyl-1,3-dihydro-imidazol-2-one

This material was obtained in analogy to example 1, step B] from (S)-2-[3-[(Z)-5-hydroxy-adamantan-2-yl]-ureido]-4-methyl-pentanoic acid methyl ester (95 mg) by treatment with diisobutylaluminium hydride (0.7 mL of a 1M solution in DCM) and conc. HCl as a white foam (20 mg). MS (ESI): 291.0 (MH⁺).

Example 41

1-[(E)-5-hydroxy-adamantan-2-yl]-4-isobutyl-1,3-dihydro-imidazol-2-one

This material was obtained in analogy to example 1, step B] from (S)-2-[3-[(E)-5-hydroxy-adamantan-2-yl]-ureido]-4-methyl-pentanoic acid methyl ester (50 mg, obtained in example 41, Step B]) by treatment with diisobutylaluminium hydride (0.59 mL of a 1M solution in DCM) and conc. HCl as a white foam (20 mg). MS (ESI): 291.0 (MH⁺).

Example 42

4-Isobutyl-1-(2-methoxy-phenyl)-1,3-dihydro-imidazol-2-one

Step A] (S)-2-[3-(2-Methoxy-phenyl)-ureido]-4-methyl-pentanoic acid methyl ester This material was obtained in analogy to example 7, step A] from L-leucine methyl ester hydrochloride (609 mg) and 2-methoxyphenylisocyanate (500 mg) as a colorless solid (930 mg). MS (ESI): 295.2 (MH$^+$).

Step B] 4-Isobutyl-1-(2-methoxy-phenyl)-1,3-dihydro-imidazol-2-one

This material was obtained in analogy to example 1, step B] from (S)-2-[3-(2-Methoxy-phenyl)-ureido]-4-methyl-pentanoic acid methyl ester (930 mg) by treatment with diisobutylaluminium hydride (3.8 mL of a 1M solution in DCM) and conc. HCl as a colorless solid (307 mg). MS (ESI): 247.1 (MH$^+$).

Example 43

3-Cyclopropylmethyl-4-isobutyl-1-(2-methoxy-phenyl)-1,3-dihydro-imidazol-2-one This material was obtained in analogy to the procedure outlined in example 23 from 4-isobutyl-1-(2-methoxy-phenyl)-1,3-dihydro-imidazol-2-one (obtained in example 42, 150 mg) by alkylation with bromomethylcyclopropane (90 mg). 3-Cyclopropylmethyl-4-isobutyl-1-(2-methoxy-phenyl)-1,3-dihydro-imidazol-2-one was obtained as a colorless oil (52 mg). MS (ESI): 301.2 (MH$^+$).

Example 44

4-Isobutyl-1-(2-trifluoromethoxy-phenyl)-1,3-dihydro-imidazol-2-one

Step A] (S)-4-Methyl-2-[3-(2-trifluoromethoxy-phenyl)-ureido]-pentanoic acid methyl ester This material was obtained in analogy to example 7, step A] from L-leucine methyl ester hydrochloride (179 mg) and 2-(trifluoromethoxy)phenylisocyanate (200 mg) as a colorless solid (930 mg). MS (ESI): 349.3 (MH$^+$).

Step B] 4-Isobutyl-1-(2-trifluoromethoxy-phenyl)-1,3-dihydro-imidazol-2-one

This material was obtained in analogy to example 1, step B] from (S)-4-methyl-2-[3-(2-trifluoromethoxy-phenyl)-ureido]-pentanoic acid methyl ester (266 mg) by treatment with diisobutylaluminium hydride (0.92 mL of a 1M solution in DCM) and conc. HCl as a colorless solid (72 mg). MS (ESI): 301.2 (MH$^+$).

Example 45

3-Cyclopropylmethyl-4-isobutyl-1-(2-trifluoromethoxy-phenyl)-1,3-dihydro-imidazol-2-one This material was obtained in analogy to the procedure outlined in example 23 from 4-isobutyl-1-(2-trifluoromethoxy-phenyl)-1,3-dihydro-imidazol-2-one (obtained in example 44, 60 mg) by alkylation with bromomethylcyclopropane (35 mg). 3-Cyclopropylmethyl-4-isobutyl-1-(2-trifluoromethoxy-phenyl)-1,3-dihydro-imidazol-2-one was obtained as a light yellow oil (11 mg). MS (ESI): 355.2 (MH$^+$).

Example 46

1-(2,4-Difluoro-phenyl)-4-isobutyl-1,3-dihydro-imidazol-2-one

Step A] (S)-2-[3-(2,4-Difluoro-phenyl)-ureido]-4-methyl-pentanoic acid methyl ester This material was obtained in analogy to example 7, step A] from L-leucine methyl ester hydrochloride (586 mg) and 2,4-difluorophenylisocyanate (500 mg) as a colorless oil (950 mg). MS (ESI): 301.3 (MH$^+$).

Step B] 1-(2,4-Difluoro-phenyl)-4-isobutyl-1,3-dihydro-imidazol-2-one

This material was obtained in analogy to example 1, step B] from (S)-2-[3-(2,4-difluoro-phenyl)-ureido]-4-methyl-pentanoic acid methyl ester (950 mg) by treatment with diisobutylaluminium hydride (3.8 mL of a 1M solution in DCM) and conc. HCl as a colorless solid (330 mg). MS (ESI): 253.1 (MH$^+$).

Example 47

4-Isobutyl-1-(2-methyl-6-trifluoromethyl-phenyl)-1,3-dihydro-imidazol-2-one

Step A] 2-Methyl-6-trifluoromethyl-phenyl-isocyanate

This compound was made from 2-methyl-6-trifluoromethyl-phenylamine in analogy to Eur. J. Med. Chem. 28 (1), 1993, 37-45 by treatment with bis-(trichloromethyl)-carbonate (627 mg) and triethylamine (1.58 mL) in DCM (16 mL). (2-Methyl-6-trifluoromethylphenyl)isocyanate was obtained as a colorless solid (1.17 g). $^1$H-NMR ($\delta$, CDCl$_3$): 7.49 (d, J=7.8 Hz, 1H), 7.41 (d, J=7.5 Hz, 1H), 7.20 (t, J=7.8 Hz, 1H), 2.40 (s, 3H).

Step B] (S)-4-Methyl-2-[3-(2-methyl-6-trifluoromethyl-phenyl)-ureido]-pentanoic acid methyl ester This material was obtained in analogy to example 7, step A] from L-leucine methyl ester hydrochloride (451 mg) and (2-methyl-6-trifluoromethylphenyl)isocyanate (500 mg) as a colorless oil (666 mg). MS (ESI): 347.2 (MH$^+$).

Step C] 4-Isobutyl-1-(2-methyl-6-trifluoromethyl-phenyl)-1,3-dihydro-imidazol-2-one This material was obtained in analogy to example 1, step B] from (S)-4-methyl-2-[3-(2-methyl-6-trifluoromethyl-phenyl)-ureido]-pentanoic acid methyl ester (666 mg) by treatment with diisobutylaluminium hydride (2.5 mL of a 1M solution in DCM) and conc. HCl as a colorless solid (283 mg). MS (EI): 298.2 (M$^+$).

Example 48

1-Adamantan-2-yl-3-cyclopropyl-4-isobutyl-1,3-dihydro-imidazol-2-one

Step A1] 2-Cyclopropylamino-4-methyl-pentanenitrile hydrochloride

Following a procedure outlined in Synth. Commun. 15 (2), 1985, 157-163, 3-methylbutyraldehyde (2.0 g) and cyclopropylamine (0.81 mL) were combined and heated to 95° C. in a pressure tube for 2 minutes. The clear, yellowish solution was cooled to RT and trimethylsilyl cyanide (2.76 mL) was added carefully over 5 minutes. The mixture was re-heated to 100° C. for 2 minutes and then allowed to cool to RT. Methanol (12 mL) was added and the mixture was heated to reflux for 12 hours. The mixture was cooled, dissolved in ethyl acetate, washed with brine, dried over $Na_2SO_4$ and evaporated. The residue was treated with HCl in dioxane (approx. 0.7 M, 30 mL) and then with ether (60 mL) with stirring. After one hour, the precipitated white solid was filtered off and dried in vacuo (1.65 g). MS (ESI): 153.4 ($MH^+$, free base).

Step B] 3-Adamantan-2-yl-1-(1-cyano-3-methyl-butyl)-1-cyclopropyl-urea

This material was obtained in analogy to example 7, step A] from 2-cyclopropylamino-4-methyl-pentanenitrile hydrochloride (500 mg) and 2-adamantyl isocyanate (470 mg) as a yellow liquid (405 mg). MS (ESI): 330.3 ($MH^+$).

Step C] 1-Adamantan-2-yl-3-cyclopropyl-4-isobutyl-1,3-dihydro-imidazol-2-one

This material was obtained in analogy to example 1, step B] from 3-adamantan-2-yl-1-(1-cyano-3-methyl-butyl)-1-cyclopropyl-urea (150 mg) by treatment with diisobutylaluminium hydride (3.8 mL of a 1M solution in DCM) and conc. HCl with the exception, that the internal temperature during DIBAH reduction was maintained at −78° C. until quenching. The desired material was obtained in low yield as a colorless solid (9 mg). MS (ESI): 315.4 ($MH^+$).

Example 49

3-Cyclopropyl-4-isopropyl-1-(2-trifluoromethyl-phenyl)-1,3-dihydro-imidazol-2-one Step A] 2-[1-Cyclopropyl-3-(2-trifluoromethyl-phenyl)-ureido]-3-methyl-butyric acid methyl ester This material was obtained in analogy to example 7, step A1 from 2-cyclopropylamino-3-methyl-butyric acid ethyl ester (436 mg, obtained in example 25, step A)) and 2-trifluoromethylphenylisocyanate (400 mg) as a yellow oil (536 mg) that was contaminated with starting material. MS (ESI): 373.2 ($MH^+$).

Step B] 3-Cyclopropyl-4-isopropyl-1-(2-trifluoromethyl-phenyl)-1,3-dihydro-imidazol-2-one This material was obtained in analogy to example 1, step B] from 2-[1-cyclopropyl-3-(2-trifluoromethyl-phenyl)-ureido]-3-methyl-butyric acid methyl ester (536 mg) by treatment with diisobutylaluminium hydride (2.5 mL of a 1M solution in DCM) and conc. HCl as a colorless solid (134 mg). MS (EI): 310.2 ($M^+$).

Example 50

4-Isobutyl-1-(2-trifluoromethyl-phenyl)-imidazolidin-2-one

4-Isobutyl-1-(2-trifluoromethyl-phenyl)-1,3-dihydro-imidazol-2-one (120 mg, obtained in example 18, step B]) was dissolved in dry ethanol (5 mL) and platinum on activated charcoal (10% Pt, 25 mg) was added. A hydrogen atmosphere was introduced by repeated evacuation/hydrogen introduction. Then, the mixture was allowed to stir under hydrogen for 20 hours with vigorous stirring. The reaction mixture was filtered through celite and the filter aid was washed well with ethyl acetate. The filtrate was concentrated in vacuo and the residue was purified by flash chromatography (gradient of 10 to 90% ethyl actete in heptane) to provide 4-isobutyl-1-(2-trifluoromethyl-phenyl)-imidazolidin-2-one as a white solid (59 mg). MS (ESI): 287.2 ($MH^+$).

Example 51

1-Adamantan-2-yl-4-isopropyl-imidazolidin-2-one

This material was obtained in analogy to the procedure outlined in example 50 from 1-adamantan-2-yl-4-isopropyl-1,3-dihydro-imidazol-2-one (100 mg) by hydrogenation. Racemic 1-Adamantan-2-yl-4-isopropyl-imidazolidin-2-one was obtained as a white foam (100 mg). MS (ESI): 263.2 ($MH^+$).

Examples 52 and 53

(R)-1-Adamantan-2-yl-4-isopropyl-imidazolidin-2-one and (S)-1-Adamantan-2-yl-4-isopropyl-imidazolidin-2-one Racemic 1-adamantan-2-yl-4-isopropyl-imidazolidin-2-one (320 mg, example 51) was subjected to preparative HPLC (Column: Chiralpack AD; Eluent: 15% ethanol in heptane; Flow: 35 mL/min; Detection: UV 220 nm) to give (R)-1-adamantan-2-yl-4-isopropyl-imidazolidin-2-one (136 mg, $t_{Ret}$=45 min) and (S)-1-adamantan-2-yl-4-isopropyl-imidazolidin-2-one (115 mg, $t_{Ret}$=64 min). Absolute configurations are tentatively assigned.

Example 54

(S)-1-Adamantan-2-yl-4-isopropyl-3-methyl-imidazolidin-2-one

This material was obtained in analogy to the procedure outlined in example 23 from (S)-1-adamantan-2-yl-4-isopropyl-imidazolidin-2-one (obtained in example 53, 88 mg) by alkylation with iodomethane (71 mg). (S)-1-Adamantan-2-yl-4-isopropyl-3-methyl-imidazolidin-2-was obtained as a white solid (92 mg). MS (EI): 276.3 ($M^+$).

Example 55

(R)-1-Adamantan-2-yl-4-isopropyl-3-methyl-imidazolidin-2-one

This material was obtained in analogy to the procedure outlined in example 23 from (R)-1-adamantan-2-yl-4-isopropyl-imidazolidin-2-one (obtained in example 53, 75 mg) by alkylation with iodomethane (61 mg). (R)-1-Adamantan-2-yl-4-isopropyl-3-methyl-imidazolidin-2-was obtained as a white solid (70 mg). MS (EI): 276.3 ($M^+$).

Examples 56 and 57

1-Adamantan-2-yl-3-isobutyl-4-isopropyl-imidazolidin-2-one and 1-Adamantan-2-yl-3-cyclopropylmethyl-4-isopropyl-imidazolidin-2-one These materials were obtained in analogy to the procedure outlined in example 50 from 1-adamantan-2-yl-3-cyclopropylmethyl-4-isopropyl-1,3-dihydro-imidazol-2-one (53 mg, obtained in example 23) by hydrogenation over platinum on charcoal. Separation of the crude reaction mixture by flash chromatography (silica gel, ethyl acetate/heptane 9:1) provided 1-adamantan-2-yl-3-isobutyl-4-isopropyl-imidazolidin-2-one as the less polar component (16 mg, $R_f$=0.7, ethyl acetate/heptane 1:1, MS (ESI): 319.3 (MH$^+$)) and 1-adamantan-2-yl-3-cyclopropylmethyl-4-isopropyl-imidazolidin-2-one as the more polar component (24 mg, $R_f$=0.65, ethyl acetate/heptane 1:1, MS (ESI): 317.3 (MH$^+$).

Example 58

1-Adamantan-2-yl-4-isobutyl-imidazolidin-2-one

This material was obtained in analogy to the procedure outlined in example 50 from 1-adamantan-2-yl-4-isobutyl-1,3-dihydro-imidazol-2-one (51 mg, obtained in example 10) by hydrogenation. 1-Adamantan-2-yl-4-isobutyl-imidazolidin-2-one was obtained as a white foam (18 mg). MS (ESI): 277.3 (MH$^+$).

Example 59

1-Adamantan-2-yl-4-cyclopropylmethyl-imidazolidin-2-one

This material was obtained in analogy to the procedure outlined in example 50 from 1-adamantan-2-yl-4-cyclopropylmethyl-1,3-dihydro-imidazol-2-one (100 mg, obtained in example 17) by hydrogenation. 1-Adamantan-2-yl-4-cyclopropylmethyl-imidazolidin-2-one was obtained as a white solid (33 mg). MS (ESI): 275.3 (MH$^+$).

Example 60

1-Adamantan-2-yl-4,4-dimethyl-imidazolidin-2-one

Step A] N$^1$-Adamantan-2-yl-2-methyl-propane-1,2-diamine

In analogy to a procedure outlined in J. Med. Chem. 32, 1989, 179-182, 2-adamantanone (500 mg) and 1,2-diaminopropane (440 mg) were dissolved in dry ethanol (12 mL) and heated to reflux for 1.5 hours. The mixture was cooled to 0° C. and sodium borohydride (164 mg) was added in portions over 5 minutes). The mixture was allowed to stir at RT for 12 hours. The mixture was evaporated and the residue was dissolved in CHCl$_3$, washed with saturated NaHCO$_3$ solution and brine, dried over Na$_2$SO$_4$ and evaporated. The residue was dried in vacuo to give a slightly yellow liquid that was used without further purification. MS (ESI): 223.4 (MH$^+$).

Step B]
1-Adamantan-2-yl-4,4-dimethyl-imidazolidin-2-one

N$^1$-Adamantan-2-yl-2-methyl-propane-1,2-diamine (250 mg) was dissolved in dry THF (6 mL) under argon and carbonyldiimidazole (182 mg) was added. The resulting mixture was allowed to stir at RT for 48 hours. The mixture was poured into water/0.5 M HCl and extracted with ethyl acetate. The organic layer was separated, washed with brine, dried over Na$_2$SO$_4$ and evaporated. The residue was purified by flash chromatography using (a gradient of 10 to 70% ethyl acetate in heptane as an eluent. The fractions containing the desired material were combined and evaporated to leave 1-adamantan-2-yl-4,4-dimethyl-imidazolidin-2-one as a white solid (256 mg). MS (EI): 248.3 (M$^+$).

Example 61

1-[(E/Z)-5-Hydroxy-adamantan-2-yl]-4,4-dimethyl-imidazolidin-2-one

Step 1] (E/Z)-4-(2-Amino-2-methyl-propylamino)-adamantan-1-ol

This material was obtained in analogy to example 60, step A1 from 5-hydroxy-2-adamantanone (400 mg) and 1,2-diamino-2-methylpropane (318 mg) by treatment with sodium borohydride (118 mg) with the exception, that the crude reaction product was purified by flash chromatography using a gradient of 0 to 50% methanol in DCM as an eluent. The desired material was obtained as a mixture of E and Z diasteromers as a light yellow oil (408 mg). MS (ESI): 239.3 (MH$^+$).

Step B] 1-[(E/Z)-5-Hydroxy-adamantan-2-yl]-4,4-dimethyl-imidazolidin-2-one

This material was obtained in analogy to example 60, step B] from (E/Z)-4-(2-amino-2-methyl-propylamino)-adamantan-1-ol (170 mg) and carbonyldiimidazole (116 mg) as a white solid (149 mg, mixture of E and Z diastereomers). MS (EI): 264.37 (M$^+$).

Example 62

3-Adamantan-2-yl-1,3-diaza-spiro[4.4]nonan-2-one

Step A]
[1-(Adamantan-2-ylcarbamoyl)-cyclopentyl]-carbamic acid tert-butyl ester A solution of BOC-1-aminocyclopentane-1-carboxylic acid (882 mg) in dry THF (15 mL) was cooled to 0° C. To this mixture were added 2-aminoadamantane (582 mg), HOBT (519 mg) and DCC (833 mg) sequentially. The mixture was allowed to warm to RT and was then stirred over night. The suspension was filtered and the filtrate was concentrated in vacuo. The residue was dissolved in ethyl acetate (20 mL), washed with water, dried over Na$_2$SO$_4$ and evaporated. The crude material was dissolved in ethyl acetate (10 mL) and precipitated with heptane (20 mL) to give the desired material as a colorless solid (1.350 g). MS (ESI): 363.3 (MH$^+$).

Step B] 1-Amino-cyclopentanecarboxylic acid adamantan-2-ylamide

To a solution of [1-(adamantan-2-ylcarbamoyl)-cyclopentyl]-carbamic acid tert-butyl ester (710 mg) in DCM (10 mL) was added TFA (1.5 mL) at 0° C. The mixture was stirred and allowed to warm to RT over night. The reaction mixture was evaporated and the residue was re-dissolved in DCM and washed with saturated NaHCO$_3$ and brine. The organic layer was dried with Na$_2$CO$_2$ and evaporated to give a residue that was purified by flash chromatography using ethyl acetate as an eluent to give the desired material as a colorless glass (377 mg). MS (ESI): 263.4 (MH$^+$).

Step C]
Adamantan-2-yl-(1-amino-cyclopentylmethyl)-amine

To a solution of 1-amino-cyclopentanecarboxylic acid adamantan-2-ylamide (220 mg) in THF (10 mL) was added borane-THF complex (4.65 mL) under argon. The mixture was then heated to reflux for 12 hours. It was then cooled and quenched with methanol (1 mL) to give a clear solution that was concentrated in vacuo. The residue was taken up in water, basified with 1 M NaOH and extracted with ethyl acetate. The organic layer was separated, dried over $Na_2SO_4$ and evaporated. The crude material was purified by flash chromatography using 0.5% $NH_4OH$ in ethyl acetate as an eluent to give adamantan-2-yl-(1-amino-cyclopentylmethyl)-amine as a colorless semisolid (155 mg). MS (ESI): 249.3 ($MH^+$).

Step D] 3-Adamantan-2-yl-1,3-diaza-spiro[4.4]nonan-2-one

This material was obtained in analogy to example 60, step B] from adamantan-2-yl-(1-amino-cyclopentylmethyl)-amine (42 mg) and 1,1-carbonyldiimidazole (93 mg) as a colorless solid (150 mg). MS (ESI): 275.3 ($MH^+$).

Example 63

3-Cyclopropyl-4-isopropyl-1-(2-trifluoromethyl-phenyl)-imidazolidin-2-one

Step A] 2-Cyclopropylamino-3-methyl-butan-1-ol

Sodium borohydride (167 mg) was added to dry THF (10 mL) under argon and cooled to 0° C. To this mixture was added 2-cyclopropylamino-3-methyl-butyric acid ethyl ester (341 mg, obtained in example 25, step A]) followed by a solution of iodine (467 mg) in THF (5 mL) that was added over a period of 30 minutes. A strong hydrogen evolution was observed. The mixture was stirred at 0° C. for 30 minutes and then heated to reflux for 12 hours. The mixture was cooled and methanol was carefully added until a clear solution was obtained. After 30 minutes, the mixture was evaporated. The residue was treated with 20% aqueous KOH solution for 4 hours. The mixture was extracted with DCM three times and the combined organic layers were dried over $Na_2SO_4$ and evaporated to give crude 2-cyclopropylamino-3-methyl-butan-1-ol as a light yellow liquid (195 mg) that was used without further purification.

Step B] 1-Cyclopropyl-1-(1-hydroxymethyl-2-methyl-propyl)-3-(2-trifluoromethyl-phenyl)-urea To a solution of crude 2-cyclopropylamino-3-methyl-butan-1-ol (195 mg) in THF (10 mL) was slowly added a solution of 2-trifluoromethylphenylisocyanate (225 mg) in THF (3 mL) at 0° C. The mixture was then heated to 60° C. for 12 hours. After cooling, the solution was concentrated in vacuo and the residue was purified by flash chromatography using ethyl acetate/heptane 1:1 as an eluent to give the desired material as a colorless solid (245 mg). MS (ESI): 331.3 ($MH^+$).

Step C] 3-Cyclopropyl-4-isopropyl-1-(2-trifluoromethyl-phenyl)-imidazolidin-2-one Following a procedure outlined in J. Org. Chem. 64, 1999, 2941-2943, sodium tert-butoxide (200 mg) and 1-cyclopropyl-1-(1-hydroxymethyl-2-methyl-propyl)-3-(2-trifluoromethyl-phenyl)-urea (245 mg) were added to THF (17 mL) and cooled to 0° C. To the mixture was added a solution of p-toluenesulfonyl chloride (170 mg) in THF (5 mL) slowly by syringe to give a suspension. The mixture was allowed to stir at RT for 12 hours and was then quenched by addition of ice cold water (15 mL). The mixture was extracted with ethyl acetate and the organic layer was separated, dried over $Na_2SO_4$ and evaporated. The crude material was purified by flash chromatography using ethyl acetate/heptane 1:1 as an eluent to give the desired material as yellow oil (170 mg). MS (ESI): 313.3 ($MH^+$).

Example 64

3,4-Dicyclopropyl-1-(2-trifluoromethyl-phenyl)-imidazolidin-2-one

Step A] Cyclopropyl-cyclopropylamino-acetonitrile

Following a procedure outlined in Synth. Commun. 15(2), 1985, 157-163, cyclopropylamine (2 g) and cyclopropanecarboxaldehyde (4.9 g) were combined in a pressure tube and heated to 100° C. for 10 minutes. The mixture was cooled to RT and trimethylsilylcyanide (8.76 mL) was added carefully with cooling by means of an ice bath (exothermic!). After addition, the mixture was reheated to 100° C. for another 10 minutes. After cooling, the mixture was diluted with ether and extracted two times with 2 N HCl. The combined aqueous extracts were basified with conc. NaOH to pH 10, saturated with NaCl and extracted with ethyl acetate. The organic layer was washed with brine, dried over $Na_2SO_4$ and evaporated. The residue was purified by flash chromatography using ethyl acetate/heptane 1:1 as an eluent to give the desired material as a colorless oil (884 mg). MS (EI): 137.2 ($M+H^+$).

Step B] Cyclopropyl-cyclopropylamino-acetic acid

Cyclopropyl-cyclopropylamino-acetonitrile (300 mg) was treated with 6N HCl (5.4 mL) at 60° C. for 12 hours. Another 5 mL of 6N HCl were added and heating was continued for another 24 hours. The reaction mixture was cooled and evaporated in vacuo. The residue was re-dissolved in water and the pH was adjusted to 5 with diluted NaOH solution. The solvent was again removed in vacuo and the residue was treated with methanol (20 mL) for 30 minutes and filtered. The filtrate was concentrated in vacuo to leave a solid (1 g). This material was a mixture of salts and the desired material cyclopropyl-cyclopropylamino-acetic acid that was used without further purification. $^1$H-NMR (d, $D_2O$): 3.02 (d, J=9.6 Hz, 1H); 2.66-2.58 (m, 1H); 1.05-0.96 (m, 1H); 0.77-0.72 (m, 4H); 0.70-0.55 (m, 2H); 0.45-0.34 (m, 2H).

Step C] 2-Cyclopropyl-2-cyclopropylamino-ethanol

Sodium borohydride (200 mg) was added to THF (10 mL), followed by cyclopropyl-cyclopropylamino-acetic acid (1 g of the material obtained in step B]). The mixture was cooled to 0° C. and a solution of iodine (558 mg) in THF (5 mL) was added carefully drop by drop over a period of 30 minutes. Vigorous hydrogen evolution was observed. The mixture was stirred at 0° C. for 30 minutes and then heated to reflux for 2 hours. The mixture was cooled and quenched with methanol until a clear solution was obtained. The solution was stirred for 30 minutes and then evaporated in vacuo. The residue was treated with 20% KOH (10 mL) and extracted with DCM. The combined organic extracts were dried over $Na_2SO_4$ and evaporated. The crude material was purified by flash chromatography using methanol/ethyl acetate 2:3 as an eluent to give 2-cyclopropyl-2-cyclopropylamino-ethanol (73 mg) as a colorless oil. MS (ESI): 142.2 ($MH^+$).

Step D] 1-Cyclopropyl-1-(1-cyclopropyl-2-hydroxy-ethyl)-3-(2-trifluoromethyl-phenyl)-urea This material was obtained in analogy to example 63, step B] from 2-cyclopropyl-2-cyclopropylamino-ethanol (73 mg) and 2-trifluoromethylphenylisocyanate (85 mg) as a colorless oil (125 mg). MS (ESI): 329.1 (MH$^+$).

Step E] 3,4-Dicyclopropyl-1-(2-trifluoromethyl-phenyl)-imidazolidin-2-one

This material was obtained in analogy to example 63, step C] from 1-cyclopropyl-1-(1-cyclopropyl-2-hydroxy-ethyl)-3-(2-trifluoromethyl-phenyl)-urea (125 mg) by treatment with sodium tert-butoxide (103 mg) and p-toluenesulfonyl chloride (87 mg) as a colorless oil (76 mg). MS (ESI): 311.2 (MH$^+$).

Example 65

1-Adamantan-2-yl-4-cyclopropyl-4-methyl-imidazolidin-2-one

Step A] 2-Cyclopropyl-propane-1,2-diamine

To an ice cold solution of 2-amino-2-cyclopropyl-propionitrile (CAS 37024-73-0, 760 mg) in toluene (35 mL) was added diisobutylaluminiumhydride (20% in toluene, 28 mL) over 15 minutes under argon. The mixture was then allowed to warm to RT and stirred over night. The mixture was cooled to −10° C. and quenched by careful addition of methanol (33.5 mL) and water (33.5 mL). The suspension was stirred for another 30 minutes and then poured into 2 M HCl. The mixture was extracted with ether. The aqueous layer was basified with conc. NaOH (pH 11) and saturated with NaCl. It was then extracted with chloroform and the organic extracts were combined, dried over Na$_2$SO$_4$ and evaporated. The residue was briefly dried in vacuo and then used without further purification. Light yellow oil (333 mg). $^1$H-NMR (δ, CDCl$_3$): 2.64 (d, J=12.6 Hz, 1H), 2.57 (d, J=12.9, 1H), 1.20 (brs, 4H), 0.92 (s, 3H), 0.83-0.75 (m, 1H), 0.40-0.30 (m, 3H), 0.25-0.18 (m, 1H).

Step B] N$^1$-Adamantan-2-yl-2-cyclopropyl-propane-1,2-diamine

This material was obtained in analogy to example 60, step A] from 2-adamantanone (175 mg) and 2-cyclopropyl-propane-1,2-diamine (200 mg) by reduction with sodium borohydride (57 mg) as a light yellow oil (154 mg). MS (ESI): 249.3 (MH$^+$).

Step C] 1-Adamantan-2-yl-4-cyclopropyl-4-methyl-imidazolidin-2-one

This material was obtained in analogy to example 60, Step B] from N$^1$-adamantan-2-yl-2-cyclopropyl-propane-1,2-diamine (151 mg) by treatment with carbonyldiimidazole (99 mg) as a white solid (143 mg). MS (EI): 274.2 (M$^+$).

Example 66

1-Adamantan-2-yl-3,4-dicyclopropyl-imidazolidin-2-one

Step A] 1,N$^1$-Dicyclopropyl-ethane-1,2-diamine

Cyclopropyl-cyclopropylamino-acetonitrile (400 mg, obtained in example 64, step A]) was reduced with diisobutylaluminiumhydride (12.4 mL of a 20% solution in toluene) in analogy to example 65, step A]. The desired material was obtained as a light yellow liquid that was used as a crude material (355 mg). MS (ESI): 141.2 (MH$^+$).

Step B] N$^2$-Adamantan-2-yl-1,N$^1$-dicyclopropyl-ethane-1,2-diamine

This material was obtained in analogy to example 60, step A] from 1,N$^1$-dicyclopropyl-ethane-1,2-diamine (140 mg) and 2-adamantanone (100 mg) by treatment with sodium borohydride (33 mg) as a light yellow liquid (162 mg). MS (ESI): 275.4 (MH$^+$).

Step C] 1-Adamantan-2-yl-3,4-dicyclopropyl-imidazolidin-2-one

This material was obtained in analogy to example 60, step B] from N$^2$-adamantan-2-yl-1,N$^1$-dicyclopropyl-ethane-1,2-diamine (156 mg) by treatment with 1,1-carbonyldiimidazole (92 mg) as a colorless oil (154 mg). MS (EI): 300.3 (M$^+$).

Examples 67 and 68

3,4-Dicyclopropyl-1-[(Z)-5-hydroxy-adamantan-2-yl]-imidazolidin-2-one and 3,4-Dicyclopropyl-1-[(E)-5-hydroxy-adamantan-2-yl]-imidazolidin-2-one Step A] (E/Z)-4-(2-Cyclopropyl-2-cyclopropylamino-ethylamino)-adamantan-1-ol This material was obtained in analogy to example 60, step A] from 1,N$^1$-dicyclopropyl-ethane-1,2-diamine (165 mg, obtained in example 66, step A)) and 5-hydroxy-2-adamantanone (165 mg) by treatment with sodium borohydride (49 mg) as a mixture of two diastereomers as a colorless gum (238 mg). MS (ESI): 291.3 (MH$^+$).

Step B] 3,4-Dicyclopropyl-1-[(Z)-5-hydroxy-adamantan-2-yl]-imidazolidin-2-one and 3,4-Dicyclopropyl-1-[(E)-5-hydroxy-adamantan-2-yl]-imidazolidin-2-one These materials were obtained in analogy to example 60, step B] from (E/Z)-4-(2-cyclopropyl-2-cyclopropylamino-ethylamino)-adamantan-1-ol (234 mg) by treatment with 1,1-carbonyldiimidazole (131 mg). The crude products of this reaction were separated by flash chromatography using a gradient of 0 to 4% methanol in ethyl acetate to give 3,4-dicyclopropyl-1-[(Z)-5-hydroxy-adamantan-2-yl]-imidazolidin-2-one (47 mg), MS (EI): 316.3 (M$^+$) as the less polar component and 3,4-dicyclopropyl-1-[(E)-5-hydroxy-adamantan-2-yl]-imidazolidin-2-one (50 mg), MS (EI): 316.3 (M$^+$) as the more polar component.

Examples 69 and 70

4-Cyclopropyl-1-[(E)-5-hydroxy-adamantan-2-yl]-4-methyl-imidazolidin-2-one and 4-Cyclopropyl-1-[(Z)-5-hydroxy-adamantan-2-yl]-4-methyl-imidazolidin-2-one Step A] (E/Z)-4-(2-Amino-2-cyclopropyl-propylamino)-adamantan-1-ol This material was obtained in analogy to example 60, step A1 from 2-cyclopropyl-propane-1,2-diamine (330 mg, obtained in example 65, step A]) and 5-hydroxy-2-adamantanone (320 mg) by treatment with sodium borohydride (95 mg) as a mixture of two diastereomers as a colorless oil (386 mg). MS (ESI): 265.3 (MH$^+$).

Step B] 4-Cyclopropyl-1-[(E)-5-hydroxy-adamantan-2-yl]-4-methyl-imidazolidin-2-one and 4-Cyclopropyl-1-[(Z)-5-hydroxy-adamantan-2-yl]-4-methyl-imidazolidin-2-one These materials were obtained in analogy to example 60, step B] from (E/Z)-4-(2-amino-2-cyclopropyl-propylamino)-adamantan-1-ol (383 mg) by treatment with 1,1-carbonyldiimidazole (235 mg). The crude products of this reaction were separated by flash chromatography using a gradient of 0 to 5% methanol in ethyl acetate to give 4-cyclopropyl-1-[(Z)-5-hydroxy-adamantan-2-yl]-4-methyl-imidazolidin-2-one (138 mg), MS (EI): 290.3 (M$^+$) as the less polar component and 4-cyclopropyl-1-[(E)-5-hydroxy-adamantan-2-yl]-4-methyl-imidazolidin-2-(168 mg), MS (EI): 290.3 (M$^+$) as the more polar component.

4-Cyclopropyl-1-[(E)-5-hydroxy-adamantan-2-yl]-4-methyl-imidazolidin-2-one (1.5 g) was subjected to preparative HPLC (Chiralpack AD, 20% EtOH in heptane) to separate enantiomers. This procedure gave (S)-4-cyclopropyl-1-[((E)-5-hydroxy-adamantan-2-yl]-4-methyl-imidazolidin-2-one (597 mg) and (R)-4-cyclopropyl-1-[(E)-5-hydroxy-adamantan-2-yl]-4-methyl-imidazolidin-2-one (561 mg) (absolute configurations tentatively assigned).

Example 71

4-Cyclopropyl-1-[(E)-5-hydroxy-adamantan-2-yl]-3,4-dimethyl-imidazolidin-2-one

This material was obtained in analogy to example 23 from 4-cyclopropyl-1-[(E)-5-hydroxy-adamantan-2-yl]-4-methyl-imidazolidin-2-one (60 mg, obtained in example 69/70) with the following modification: 2.5 equivalents of sodium hydride (55% in mineral oil, 23 mg) were used for deprotonation, followed by alkylation with iodomethane (32 mg). 4-Cyclopropyl-1-[((E)-5-hydroxy-adamantan-2-yl]-3,4-dimethyl-imidazolidin-2-one was obtained as a white solid (51 mg). MS (ESI): 305.2 (MH$^+$).

Example 72

1-Adamantan-2-yl-4-isopropyl-4-methyl-imidazolidin-2-one

Step A][1-(Adamantan-2-ylcarbamoyl)-1,2-dimethyl-propyl]-carbamic acid tert-butyl ester This material was obtained in analogy to example 62, step A] from BOC-α-methyl-(D/L)-valine (392 mg) and 2-aminoadamantane (600 mg) by treatment with HOBT (350 mg) and DCC (561 mg) as a colorless solid (455 mg). MS (ESI): 365.4 (MH$^+$).

Step B]
N-Adamantan-2-yl-2-amino-2,3-dimethyl-butyramide

This material was obtained in analogy to example 62, step B] from [1-(adamantan-2-ylcarbamoyl)-1,2-dimethyl-propyl]-carbamic acid tert-butyl ester (410 mg) by treatment with TFA (0.86 mL) as colorless glass (162 mg). MS (ESI): 265.3 (MH$^+$).

Step C] N$^1$-Adamantan-2-yl-2,3-dimethyl-butane-1,2-diamine

This material was obtained in analogy to example 62, step C] from N-adamantan-2-yl-2-amino-2,3-dimethyl-butyramide (162 mg) by reduction with borane-THF-complex (3.4 mL) as a colorless glass (64 mg). MS (ESI): 251.4 (MH$^+$).

Step D] 1-Adamantan-2-yl-4-isopropyl-4-methyl-imidazolidin-2-one

This material was obtained in analogy to example 60, step B] from N$^1$-adamantan-2-yl-2,3-dimethyl-butane-1,2-diamine (64 mg) by treatment with 1,1-carbonyldiimidazole (42 mg) as colorless solid (43 mg). MS (ESI): 277.3 (MH$^+$).

Examples 73 and 74

1-[(Z)-5-hydroxy-adamantan-2-yl]-4-isopropyl-3-methyl-imidazolidin-2-one and 1-[(E)-5-hydroxy-adamantan-2-yl]-4-isopropyl-3-methyl-imidazolidin-2-one Step A] 3,N$^2$-Dimethyl-butane-1,2-diamine 3-Methyl-2-(methylamino)-butanenitrile (1.2 g, CAS 60727-35-7, Tetrahedron 56(16), 2523-2531; 2000) was reduced with diisobutylaluminiumhydride (20% in toluene, 44.2 mL) as described in example 65, step A1 to give the desired material 3,N$^2$-dimethyl-butane-1,2-diamine as a light yellow liquid (787 mg) that was used without purification. MS (ESI-Turbo Spray): 117.2 (MH$^+$).

Step B] (E/Z)-4-(3-Methyl-2-methylamino-butylamino)-adamantan-1-ol

This material was obtained in analogy to example 60, step A] from 3,N$^2$-dimethyl-butane-1,2-diamine (766 mg) and 5-hydroxy-2-adamantanone (730 mg) by reductive amination with sodium borohydride (216 mg) as light yellow semisolid (779 mg). MS (ESI): 267.3 (MH$^+$).

Step C] 1-[(Z)-5-hydroxy-adamantan-2-yl]-4-isopropyl-3-methyl-imidazolidin-2-one and 1-[(E)-5-hydroxy-adamantan-2-yl]-4-isopropyl-3-methyl-imidazolidin-2-one These materials were obtained in analogy to example 60, step B] from (E/Z)-4-(3-methyl-2-methylamino-butylamino)-adamantan-1-ol (772 mg) by treatment with 1,1-carbonyldiimidazole (705 mg). The crude products of this reaction were separated by flash chromatography using a gradient of 0 to 3% methanol in ethyl acetate to give 1-[(Z)-5-hydroxy-adamantan-2-yl]-4-isopropyl-3-methyl-imidazolidin-2-one (268 mg), MS (EI): 292.3 (M$^+$), as the less polar component and 1-[(E)-5-hydroxy-adamantan-2-yl]-4-isopropyl-3-methyl-imidazolidin-2-one (321 mg), MS (EI): 292.3 (M$^+$), as the more polar component.

Example 75

1-Adamantan-2-yl-3,4-dicyclopropyl-4-methyl-imidazolidin-2-one

Step A]
2-Cyclopropyl-2-cyclopropylamino-propionitrile

This material was obtained in analogy to example 64, step A] from cyclopropylmethylketone (9.84 mL), cyclopropylamine (3.7 mL) and trimethylsilylcyanide (13.2 mL) as a light yellow oil (7.45 g). MS (ESI): 151.2 (MH$^+$).

Step B] 2,N$^2$-Dicyclopropyl-propane-1,2-diamine

This material was obtained in analogy to example 65, step A] from 2-cyclopropyl-2-cyclopropylamino-propionitrile (1.0 g) by reduction with diisobutylaluminiumhydride (20% in toluene, 27.5 mL) as a colorless oil (144 mg) after chromatography (ethyl acetate/methanol/NH$_4$OH 1:1:0.2). MS (ESI): 155.2 (MH$^+$).

Step C] N$^1$-Adamantan-2-yl-2,N$^2$-dicyclopropyl-propane-1,2-diamine

This material was obtained in analogy to example 60, step A] from 2,N$^2$-dicyclopropyl-propane-1,2-diamine (144 mg) and 2-adamantanone (93 mg) by reductive amination with sodium borohydride (31 mg) as a colorless oil (115 mg). MS (ESI): 289.3 (MH$^+$).

Step D] 1-Adamantan-2-yl-3,4-dicyclopropyl-4-methyl-imidazolidin-2-one

This material was obtained in analogy to example 60, step B] in low yield from N$^1$-adamantan-2-yl-2,N$^2$-dicyclopropyl-propane-1,2-diamine (115 mg) by treatment with 1,1-carbonyldiimidazole (78 mg) as colorless oil (11 mg). MS (ESI): 315.3 (MH$^+$).

Examples 76 and 77

3-Cyclopropyl-1-[(Z)-5-hydroxy-adamantan-2-yl]-4,4-dimethyl-imidazolidin-2-one and 3-Cyclopropyl-1-[(E)-5-hydroxy-adamantan-2-yl]-4,4-dimethyl-imidazolidin-2-one Step A]
2-(Cyclopropylamino)-2-methyl-propanenitrile This material was obtained in analogy to example 64, step A] from acetone (7.73 mL, cyclopropyl amine (3 g) and trimethylsilylcyanide (13.2 mL) as a light yellow liquid (2.5 g). $^1$H-NMR (CDCl$_3$): 2.3 (m, 1H), 2.05 (s, br, 1H), 1.49 (s, 6H), 0.58 (m, 2H), 0.41 (m, 2H).

Step B] N$^2$-Cyclopropyl-2-methyl-propane-1,2-diamine

This material was obtained in analogy to example 65, step A] from 2-(cyclopropylamino)-2-methyl-propanenitrile (1.0 g) by reduction with diisobutylaluminiumhydride (20% in toluene, 33.3 mL) as a light yellow liquid (640 mg) that was used as crude material without further purification. $^1$H-NMR (CDCl$_3$): 2.58 (s, 2H), 2.05 (m, 1H), 1.50 (s, br, 3H), 1.08 (s, 6H), 0.44 (m, 2H), 0.30 (m, 2H).

Step C] (E/Z)-4-(2-Cyclopropylamino-2-methyl-propylamino)-adamantan-1-ol

This material was obtained in analogy to example 60, step A1 from N$^2$-cyclopropyl-2-methyl-propane-1,2-diamine (498 mg) and 5-hydroxy-2-adamantanone (430 mg) by reductive amination with sodium borohydride (127 mg) as a mixture of diastereomers as light yellow gum (572 mg). MS (ESI): 279.3 (MH$^+$).

Step D] 3-Cyclopropyl-1-[(Z)-5-hydroxy-adamantan-2-yl]-4,4-dimethyl-imidazolidin-2-one and 3-Cyclopropyl-1-[(E)-5-hydroxy-adamantan-2-yl]-4,4-dimethyl-imidazolidin-2-one (E/Z)-4-(2-Cyclopropylamino-2-methyl-propylamino)-adamantan-1-ol (420 mg) was dissolved in DCM (16 mL) and cooled to 0° C. by means of an ice bath. To this solution was added a solution of triethyl amine (0.47 mL) in DCM (8 mL) drop by drop. A solution of bis-(trichloromethyl)-carbonate (166 mg) in DCM (8 mL) was added dropwise and the mixture was allowed to stir for 30 minutes at 0° C. and then at RT over night. The reaction mixture was extracted with 1 M HCl, washed with brine, dried over Na$_2$SO$_4$ and evaporated to give a crude product. This was purified by flash chromatography (gradient of MeOH in ethyl actate, 0 to 5%) to give 3-cyclopropyl-1-[(Z)-5-hydroxy-adamantan-2-yl]-4,4-dimethyl-imidazolidin-2-one (79 mg, light yellow solid, MS (ESI): 305.2 (MH$^+$)) and 3-cyclopropyl-1-[(E)-5-hydroxy-adamantan-2-yl]-4,4-dimethyl-imidazolidin-2-one (172 mg, colorless foam, MS (ESI): 305.2 (MH$^+$).

Example 78

1-Adamantan-2-yl-3-cyclopropyl-4,4-dimethyl-imidazolidin-2-one

Step A] N$^1$-Adamantan-2-yl-N$^2$-cyclopropyl-2-methyl-propane-1,2-diamine

This material was obtained in analogy to example 60, step A] from N$^2$-cyclopropyl-2-methyl-propane-1,2-diamine (90 mg, obtained in example 76/77, step B]) and 2-adamantanone (70 mg) by reductive amination with sodium borohydride (23 mg) as a white solid (82 mg). MS (ESI): 263.4 (MH$^+$).

Step B] 1-Adamantan-2-yl-3-cyclopropyl-4,4-dimethyl-imidazolidin-2-one

This material was obtained in analogy to example 76/77, step D] from N$^1$-adamantan-2-yl-N$^2$-cyclopropyl-2-methyl-propane-1,2-diamine (72 mg) by treatment with triethyl amine (63 mg) and bis-(trichloromethy)-carbonate (30 mg) as a white solid (61 mg). MS (ESI): 289.1 (MH$^+$).

Examples 79 and 80

3,4-Dicyclopropyl-1-[(Z)-5-hydroxy-adamantan-2-yl]-4-methyl-imidazolidin-2-one and 3,4-Dicyclopropyl-1-[(E)-5-hydroxy-adamantan-2-yl]-4-methyl-imidazolidin-2-one Step A]
2-Cyclopropyl-2-cyclopropylamino-propionitrile This material was obtained in analogy to example 64, step A] from acetylcyclopropane (9.84 mL, cyclopropyl amine (3.7 mL) and trimethylsilylcyanide (10.4 mL) as a light yellow oil (7.5 g). $^1$H-NMR (CDCl$_3$): 2.27 (m, 1H), 2.22 (s, br, 1H), 1.57 (s, 3H), 0.99 (m, 1H), 0.66-0.54 (m, 6H), 0.45 (m, 2H).

Step B] 2,N$^2$-Dicyclopropyl-propane-1,2-diamine

This material was obtained in analogy to example 65, step A1 from 2-cyclopropyl-2-cyclopropylamino-propionitrile (3.0 g) by reduction with diisobutylaluminiumhydride (20%

Step C] (E/Z)-4-(2-Cyclopropyl-2-cyclopropylamino-propylamino)-adamantan-1-ol

This material was obtained in analogy to example 60, step A] from 2,N²-dicyclopropyl-propane-1,2-diamine (696 mg) and 5-hydroxy-2-adamantanone (500 mg) by reductive amination with sodium borohydride (148 mg) as a mixture of diastereomers as a colorless oil (572 mg). MS (ESI): 305.3 (MH$^+$).

Step D] 3,4-Dicyclopropyl-1-[(Z)-5-hydroxy-adamantan-2-yl]-4-methyl-imidazolidin-2-one and 3,4-Dicyclopropyl-1-[(E)-5-hydroxy-adamantan-2-yl]-4-methyl-imidazolidin-2-one These materials were obtained in analogy to example 76/77 from (E/Z)-4-(2-cyclopropyl-2-cyclopropylamino-propylamino)-adamantan-1-ol (251 mg) by treatment with triethylamine (0.23 mL) and bis-(trichloromethyl)-carbonate (91 mg) to give 3,4-dicyclopropyl-1-[(Z)-5-hydroxy-adamantan-2-yl]-4-methyl-imidazolidin-2-one (38 mg, colorless gum, MS (ESI): 331.3 (MH$^+$)) and 3,4-dicyclopropyl-1-[(E)-5-hydroxy-adamantan-2-yl]-4-methyl-imidazolidin-2-one (90 mg, colorless gum, MS (ESI): 331.3 (MH$^+$)).

Examples 81 and 82

3-[(Z)-5-hydroxy-adamantan-2-yl]-1,3-diaza-spiro[4.4]nonan-2-one and 3-[(E)-5-hydroxy-adamantan-2-yl]-1,3-diaza-spiro[4.4]nonan-2-one Step A] 1-Aminomethyl-cyclopentylamine This known material (CAS 49830-37-7) was obtained according to example 65, step A] 1-amino-cyclopentanecarbonitrile (1.5 g, CAS 49830-37-7) by reduction with diisobutylaluminiumhydride (20% in toluene, 48.4 mL) as a colorless liquid (417 mg) after purification by flash chromatography (ethyl acetate/MeOH/NH$_4$OH 1:1:0.1). $^1$H-NMR (CDCl$_3$): 2.64 (s, 2H); 1.83-1.70 (m, >5H (2 CH, 3 NH, H$_2$O)); 1.70-1.39 (m, 6H).

Step B] (E/Z)-4-[(1-Amino-cyclopentylmethyl)-amino]-adamantan-1-ol

This material was obtained in analogy to example 60, step A] from 1-aminomethyl-cyclopentylamine (417 mg) and 5-hydroxy-2-adamantanone (400 mg) by reductive amination with sodium borohydride (118 mg) as a mixture of diastereomers as a colorless solid (663 mg). MS (ESI): 365.3 (MH$^+$).

Step C] 3-[(Z)-5-hydroxy-adamantan-2-yl]-1,3-diaza-spiro[4.4]nonan-2-one and 3-[(E)-5-hydroxy-adamantan-2-yl]-1,3-diaza-spiro[4.4]nonan-2-one These materials were obtained in analogy to example 76/77 from (E/Z)-4-[(1-amino-cyclopentylmethyl)-amino]-adamantan-1-ol (630 mg) by treatment with triethylamine (0.67 mL) and bis-(trichloromethyl)-carbonate (262 mg) to give 3-[(Z)-5-hydroxy-adamantan-2-yl]-1,3-diaza-spiro[4.4]nonan-2-one (138 mg, colorless glass, MS (ESI): 291.3 (MH$^+$)) and 3-[(E)-5-hydroxy-adamantan-2-yl]-1,3-diaza-spiro[4.4]nonan-2-one (190 mg, colorless glass, MS (ESI): 291.3 (MH$^+$)).

Examples 83 and 84

4,4-Dicyclopropyl-1-[(Z)-5-hydroxy-adamantan-2-yl]-imidazolidin-2-one and 4,4-Dicyclopropyl-1-[(E)-5-hydroxy-adamantan-2-yl]-imidazolidin-2-one Step A] α-Amino-α-cyclopropyl-cyclopropaneacetonitrile This known material (CAS 752922-40-0) was obtained in low yield by Strecker synthesis: NH$_4$Cl (695 mg) was dissolved in 25% aq. NH$_4$OH (3.5 mL) and then a solution of dicyclopropylketone in MeOH (3.5 mL) was added. To the clear solution was then added KCN (426 mg) in three portions and the resulting mixture was allowed to stir over night. The mixture was cooled and poured into DCM and water that was saturated with NaCl. The organic layer was separated, washed with brine, dried over Na$_2$SO$_4$ and evaporated. The residue was chromatographed (ethyl acetate/heptane 1:1) to give starting ketone (713 mg) and α-amino-α-cyclopropyl-cyclopropaneacetonitrile (142 mg) as a light yellow oil. $^1$H-NMR (CDCl$_3$): 1.79 (s, br, 2H), 1.17 (m, 2H), 1.60 (m, 8H).

Step B] 1,1-Dicyclopropyl-ethane-1,2-diamine

This material was obtained according to example 65, step A] α-amino-α-cyclopropyl-cyclopropaneacetonitrile (266 mg) by reduction with diisobutylaluminiumhydride (20% in toluene, 8.1 mL) as a colorless semisolid (106 mg) after purification by flash chromatography (ethyl acetate/MeOH/NH$_4$OH 1:1:0.1). $^1$H-NMR (CDCl$_3$): 2.66 (s, 2H); 1.70 (s, br, >4H, 4 NH and H$_2$O), 0.71 (m, 2H), 0.40-0.21 (m, 8H).

Step C] (E/Z)-4-(2-Amino-2,2-dicyclopropyl-ethylamino)-adamantan-1-ol

This material was obtained in analogy to example 60, step A] from 1,1-dicyclopropyl-ethane-1,2-diamine (105 mg) and 5-hydroxy-2-adamantanone (83 mg) by reductive amination with sodium borohydride (25 mg) as a mixture of diastereomers as a colorless gum (126 mg). MS (ESI): 291.3 (MH$^+$).

Step D] 4,4-Dicyclopropyl-1-[(Z)-5-hydroxy-adamantan-2-yl]-imidazolidin-2-one and 4,4-Dicyclopropyl-1-[(E)-5-hydroxy-adamantan-2-yl]-imidazolidin-2-one These materials were obtained in analogy to example 76/77 from (E/Z)-4-(2-amino-2,2-dicyclopropyl-ethylamino)-adamantan-1-ol (630 mg) by treatment with triethylamine (0.12 mL) and bis-(trichloromethyl)-carbonate (48 mg) to give 3,4-dicyclopropyl-1-[(Z)-5-hydroxy-adamantan-2-yl]-4-methyl-imidazolidin-2-one (35 mg, colorless glass, MS (ESI): 317.2 (MH$^+$)) and 3,4-dicyclopropyl-1-[(E)-5-hydroxy-adamantan-2-yl]-4-methyl-imidazolidin-2-one (27 mg, colorless glass, MS (ESI): 317.2 (MH$^+$)). Both materials were slightly contaminated with the other diastereomer.

Example 85

3-[(E)-5-hydroxy-adamantan-2-yl]-1-methyl-1,3-diaza-spiro[4.4]nonan-2-one

This material was obtained in analogy to example 71 from 3-[(E)-5-hydroxy-adamantan-2-yl]-1,3-diaza-spiro[4.4]nonan-2-one (50 mg, obtained in example 81/82) by treatment with sodium hydride (55% in mineral oil, 19 mg) and iodomethane (24 mg) as a colorless solid (25 mg). MS (ESI): 305.3 (MH$^+$).

Example 86

4-Cyclopropyl-1-[(E)-5-methoxy-adamantan-2-yl]-3,4-dimethyl-imidazolidin-2-one

This material can be isolated when 4-cyclopropyl-1-[(E)-5-hydroxy-adamantan-2-yl]-4-methyl-imidazolidin-2-one is treated with sodium hydride and more than 1 equivalent of iodomethane as described in example 71 (corresponding to the N,O-di-methylated product). MS (ESI): 319.3 (MH$^+$).

Example 87

3-Ethyl-1-[(E)-5-hydroxy-adamantan-2-yl]-4,4-dimethyl-imidazolidin-2-one

This material was obtained in analogy to example 71 from 1-[(E)-5-hydroxy-adamantan-2-yl]-4,4-dimethyl-imidazolidin-2-one (100 mg, obtained in example 61, (E)-isomer purified by flash chromatography on silica gel using a gradient of 0 to 5% MeOH in ethyl acetate as the eluent) by alkylation with iodoethane (62 mg) in the presence of sodium hydride (41 mg, 55% in mineral oil) in DMF (6 ml). 3-Ethyl-1-[(E)-5-hydroxy-adamantan-2-yl]-4,4-dimethyl-imidazolidin-2-one was obtained as a colorless solid (68 mg). MS (ESI): 293.3 (MH$^+$).

Example 88

3-(2-Fluoro-ethyl)-1-[(E)-5-hydroxy-adamantan-2-yl]-4,4-dimethyl-imidazolidin-2-one This material was obtained in analogy to example 71 from 1-[(E)-5-hydroxy-adamantan-2-yl]-4,4-dimethyl-imidazolidin-2-one (100 mg, obtained in example 61, (E)-isomer purified by flash chromatography on silica gel using a gradient of 0 to 5% MeOH in ethyl acetate as the eluent) by alkylation with 1-bromo-2-fluoroethane (50 mg) in the presence of sodium hydride (41 mg, 55% in mineral oil) in DMF (6 ml). 3-(2-Fluoro-ethyl)-1-[(E)-5-hydroxy-adamantan-2-yl]-4,4-dimethyl-imidazolidin-2-one was obtained as a colorless oil (20 mg). MS (ESI): 311.3 (MH$^+$).

Example 89

1-[(E)-5-Hydroxy-adamantan-2-yl]-3,4,4-trimethyl-imidazolidin-2-one

This material was obtained in analogy to example 71 from 1-[(E)-5-hydroxy-adamantan-2-yl]-4,4-dimethyl-imidazolidin-2-one (55 mg, obtained in example 61, (E)-isomer purified by flash chromatography on silica gel using a gradient of 0 to 5% MeOH in ethyl acetate as the eluent) by alkylation with iodomethane (31 mg) in the presence of sodium hydride (23 mg, 55% in mineral oil) in DMF (4 ml). 1-[(E)-5-hydroxy-adamantan-2-yl]-3,4,4-trimethyl-imidazolidin-2-one was obtained as a yellow solid (35 mg). MS (ESI): 279.2 (MH$^+$).

Examples 90 and 91

1-[(Z)-5-Hydroxy-adamantan-2-yl]-4-isopropyl-4-methyl-imidazolidin-2-one and 1-[(E)-5-hydroxy-adamantan-2-yl]-4-isopropyl-4-methyl-imidazolidin-2-one Step A] (E/Z)-4-(2-Amino-2,3-dimethyl-butylamino)-adamantan-1-ol This material was obtained in analogy to example 60, step A] from known (+/−)-2,3-dimethyl-butane-1,2-diamine (CAS 157663-74-6, 1.81 g) and 5-hydroxy-2-adamantanone (1.9 g) by reductive amination as a colorless semisolid (2.71 g). MS (ESI): 267.3 (MH$^+$).

Step B] 1-[(Z)-5-Hydroxy-adamantan-2-yl]-4-isopropyl-4-methyl-imidazolidin-2-one and 1-[(E)-5-hydroxy-adamantan-2-yl]-4-isopropyl-4-methyl-imidazolidin-2-one These materials were obtained in analogy to example 76/77 from (E/Z)-4-(2-amino-2,3-dimethyl-butylamino)-adamantan-1-ol (2.7 g) by treatment with triethylamine (2.84 mL) and bis-(trichloromethyl)-carbonate (1.12 g) to give, after separation by column chromatography, 1-[(Z)-5-hydroxy-adamantan-2-yl]-4-isopropyl-4-methyl-imidazolidin-2-one (910 mg, colorless glass, MS (ESI): 293.2 (MH$^+$)) and 1-[(E)-5-hydroxy-adamantan-2-yl]-4-isopropyl-4-methyl-imidazolidin-2-one (950 mg, colorless glass, MS (ESI): 292.2 (MH$^+$)).

Example 92

1-[(E)-5-Hydroxy-adamantan-2-yl]-4-isopropyl-3,4-dimethyl-imidazolidin-2-one

This material was obtained in analogy to example 71 from 1-[(E)-5-hydroxy-adamantan-2-yl]-4-isopropyl-4-methyl-imidazolidin-2-one (200 mg, obtained in example 90/91) by treatment with sodium hydride (55% in mineral oil, 45 mg) and iodomethane (97 mg) as a colorless solid (120 mg). MS (ESI): 307.4 (MH$^+$).

Example 93

3-Ethyl-1-[(E)-5-hydroxy-adamantan-2-yl]-4-isopropyl-4-methyl-imidazolidin-2-one This material was obtained in analogy to example 71 from 1-[(E)-5-hydroxy-adamantan-2-yl]-4-isopropyl-4-methyl-imidazolidin-2-one (200 mg, obtained in example 90/91) by treatment with sodium hydride (55% in mineral oil, 75 mg) and iodomethane (117 mg) as a colorless gum (95 mg). MS (ESI): 321.3 (MH$^+$).

Example 94

(R or S)-4-Cyclopropyl-3-ethyl-1-[(E)-5-hydroxy-adamantan-2-yl]-4-methyl-imidazolidin-2-one This material was obtained in analogy to example 71 from (R or S)-4-cyclopropyl-1-[(E)-5-hydroxy-adamantan-2-yl]-4-methyl-imidazolidin-2-one (40 mg, obtained in example 69 after separation of the enantiomers by prep. HPLC) by treatment with sodium hydride (55% in mineral oil, 15 mg) and iodomethane (24 mg) as a colorless gum (24 mg). MS (ESI): 319.3 (MH$^+$).

Examples 95 and 96

1-Cyclopropyl-3-[(Z)-5-hydroxy-adamantan-2-yl]-1,3-diaza-spiro[4.4]nonan-2-one and 1-Cyclopropyl-3-[(E)-5-hydroxy-adamantan-2-yl]-1,3-diaza-spiro[4.4]nonan-2-one Step A]
1-Cyclopropylamino-cyclopentanecarbonitrile This material was obtained in analogy to example 64, step A] from cyclopentanone (9.33 mL), cyclopropylamine (3.7 mL) and trimethylsilylcyanide (13.2 mL) as a colorless oil (7.58 g). MS (ESI): 151.3 (MH$^+$).

Step B]
(1-Aminomethyl-cyclopentyl)-cyclopropyl-amine

This material was obtained in analogy to example 65, step A] from 1-cyclopropylamino-cyclopentanecarbonitrile (3.0 g) by reduction with diisobutylaluminiumhydride (20% in toluene, 282.6 mL) as a colorless liquid (1.24 mg) after silica gel chromatography (DCM/methanol/NH$_4$OH 9:1:0.1). MS (ESI): 155.2 (MH$^+$).

Step C] (E/Z)-4-[(1-Amino-cyclopentylmethyl)-amino]-adamantan-1-ol

This material was obtained in analogy to example 60, step A] from known (1-aminomethyl-cyclopentyl)-cyclopropyl-amine (556 mg) and 5-hydroxy-2-adamantanone (400 mg) by reductive amination with NaBH$_4$ (118 mg) as a colorless glass (570 mg). MS (ESI): 265.3 (MH$^+$).

Step D] 1-Cyclopropyl-3-[(Z)-5-hydroxy-adamantan-2-yl]-1,3-diaza-spiro[4.4]nonan-2-one and 1-Cyclopropyl-3-[(E)-5-hydroxy-adamantan-2-yl]-1,3-diaza-spiro[4.4]nonan-2-one These materials were obtained in analogy to example 76/77 from (E/Z)-4-[(1-amino-cyclopentylmethyl)-amino]-adamantan-1-ol (570 mg) by treatment with triethylamine (0.523 mL) and bis-(trichloromethyl)-carbonate (206 mg) to give, after separation by column chromatography, 1-cyclopropyl-3-[(Z)-5-hydroxy-adamantan-2-yl]-1,3-diaza-spiro[4.4]nonan-2-one (80 mg, colorless glass, MS (ESI): 331.4 (MH$^+$)) and 1-cyclopropyl-3-[(E)-5-hydroxy-adamantan-2-yl]-1,3-diaza-spiro[4.4]nonan-2-one (180 mg, colorless solid, MS (ESI): 331.4 (MH$^+$)).

Examples 97 and 98

7-Benzyl-3-[(Z)-5-hydroxy-adamantan-2-yl]-1,3,7-triaza-spiro[4.5]decan-2-one and 7-Benzyl-3-[(E)-5-hydroxy-adamantan-2-yl]-1,3,7-triaza-spiro[4.5]decan-2-one Step A]
3-Aminomethyl-1-benzyl-piperidin-3-ylamine This material was obtained in analogy to example 65, step A] from known 3-amino-1-benzyl-piperidine-3-carbonitrile (CAS 153931-24-9, 1.23 g) by reduction with diisobutylaluminiumhydride (20% in toluene, 14.2 mL) as a colorless glass (458 mg) after silica gel chromatography (DCM/methanol/NH$_4$OH 9:1:0.1). MS (ESI): 220.3 (MH$^+$).

Step B] (E/Z)-4-[(3-Amino-1-benzyl-piperidin-3-ylmethyl)-amino]-adamantan-1-ol

This material was obtained in analogy to example 60, step A] from 3-aminomethyl-1-benzyl-piperidin-3-ylamine (458 mg) and 5-hydroxy-2-adamantanone (300 mg) by reductive amination with NaBH$_4$ (89 mg) as a colorless oil (570 mg). MS (ESI): 370.4 (MH$^+$).

Step C] 7-Benzyl-3-[(Z)-5-hydroxy-adamantan-2-yl]-1,3,7-triaza-spiro[4.5]decan-2-one and 7-Benzyl-3-[(E)-5-hydroxy-adamantan-2-yl]-1,3,7-triaza-spiro[4.5]decan-2-one These materials were obtained in analogy to example 76/77 from (E/Z)-4-[(3-Amino-1-benzyl-piperidin-3-ylmethyl)-amino]-adamantan-1-ol (586 mg) by treatment with triethylamine (0.442 mL) and bis-(trichloromethyl)-carbonate (174 mg) to give, after separation by column chromatography, 7-benzyl-3-[(Z)-5-hydroxy-adamantan-2-yl]-1,3,7-triaza-spiro[4.5]decan-2-one (115 mg, colorless glass, MS (ESI): 396.3 (MH$^+$)) and 7-benzyl-3-[(E)-5-hydroxy-adamantan-2-yl]-1,3,7-triaza-spiro[4.5]decan-2-one (207 mg, colorless glass, MS (ESI): 396.3 (MH$^+$)).

Example 99

7-Benzyl-3-[(E)-5-hydroxy-adamantan-2-yl]-1-methyl-1,3,7-triaza-spiro[4.5]decan-2-one This material was obtained in analogy to example 71 from 7-benzyl-3-[(E)-5-hydroxy-adamantan-2-yl]-1,3,7-triaza-spiro[4.5]decan-2-one (100 mg, obtained in example 97/98) by treatment with sodium hydride (55% in mineral oil, 17 mg) and iodomethane (36 mg) as a colorless oil (67 mg). MS (ESI): 410.3 (MH$^+$).

Examples 100 and 101

1',3'-Dihydro-1-[(Z)-5-hydroxy-adamantan-2-yl]-spiro[imidazolidine-4,2'-[2H]indene]-2-one and 1',3'-Dihydro-1-[(E)-5-hydroxy-adamantan-2-yl]-spiro[imidazolidine-4,2'-[2H]indene]-2-one Step A] (E/Z)-4-[(2-Amino-indan-2-ylmethyl)-amino]-adamantan-1-ol This material was obtained in analogy to example 60, step A] from known 2-amino-2,3-dihydro-1H-indene-2-methanamine (CAS 144800-63-5, 324 mg) and 5-hydroxy-2-adamantanone (255 mg) by reductive amination with NaBH$_4$ (75 mg) as a light brown foam (410 mg). MS (ESI): 370.4 (MH$^+$).

Step b] 1',3'-Dihydro-1-[(Z)-5-hydroxy-adamantan-2-yl]-spiro[imidazolidine-4,2'-[2H]indene]-2-one and 1',3'-Dihydro-1-[(E)-5-hydroxy-adamantan-2-yl]-spiro[imidazolidine-4,2'-[2H]indene]-2-one These materials were obtained in analogy to example 76/77 from (E/Z)-4-[(2-amino-indan-2-ylmethyl)-amino]-adamantan-1-ol (405 mg) by treatment with triethylamine (0.410 mL) and bis-(trichloromethyl)-carbonate (142 mg) to give, after separation by column chromatography, 1',3'-dihydro-1-[(Z)-5-hydroxy-adamantan-2-yl]-spiro[imidazolidine-4,2'-[2H]indene]-2-one (155 mg, colorless glass, MS (ESI): 339.1 (MH$^+$)) and 1',3'-dihydro-1-[(E)-5-hydroxy-adamantan-2-yl]-spiro[imidazolidine-4,2'-[2H] indene]-2-one (221 mg, colorless glass, MS (ESI): 339.1 (MH$^+$)).

Example 102

1',3'-Dihydro-1-[(E)-5-hydroxy-adamantan-2-yl]-3-methyl-spiro[imidazolidine-4,2'-[2H]indene]-2-one This material was obtained in analogy to example 71 from 1',3'-dihydro-1-[(E)-5-hydroxy-adamantan-2-yl]-spiro[imidazolidine-4,2'-[2H]indene]-2-one (80 mg, obtained in example 100/101) by treatment with sodium hydride (55% in mineral oil, 26 mg) and iodomethane (37 mg) as a white solid (71 mg). MS (ESI): 353.2 (MH$^+$).

Example 103

1-[(E)-5-Aminoadamantan-2-yl]-1',3'-dihydro-2H-spiro[imidazolidine-4,2'-inden]-2-one Step A] 2-Chloro-N-[(E)-4-(2-oxo-1',3'-dihydro-1H-spiro[imidazolidine-4,2'-inden]-1-yl)adamantan-1-yl]acetamide To a mixture of 1',3'-Dihydro-1-[(E)-5-hydroxy-adamantan-2-yl]-spiro[imidazolidine-4,2'-[2H]indene]-2-one (102 mg, obtained in example 100/101) and chloroacetonitrile (93 mg) in acetic acid (0.6 ml), sulfuric acid (0.4 ml) was added dropwise at 0° C. The mixture was stirred at room temperature for 5 hr. To the mixture, chloroacetonitrile (0.15 ml) and sulfuric acid (0.2 ml) were added. The mixture was stirred for 16 hr. The mixture was poured into saturated Na$_2$CO$_3$ solution, and extracted with AcOEt. The organic layer was washed with saturated Na$_2$CO$_3$ solution, and brine, dried over Na$_2$SO$_4$ and evaporated. The residue was purified with silica gel chromatography (CH$_2$Cl$_2$:MeOH:NH$_4$OH=95:5:0.25) to obtain the title compound (185 mg) as a white solid. MS (ESI): 414.3 (MH$^+$).

Step B] 1-[(E)-5-Aminoadamantan-2-yl]-1',3'-dihydro-2H-spiro[imidazolidine-4,2'-inden]-2-one A mixture of 2-chloro-N-[(E)-4-(2-oxo-1',3'-dihydro-1H-spiro[imidazolidine-4,2'-inden]-1-yl)adamantan-1-yl]acetamide (160 mg, obtained in examples 103, step A) and thiourea (36 mg) in ethanol (5.0 ml), and acetic acid (1.0 ml) refluxed for 16 hr under Ar. The mixture was basified with 1N NaOH and extracted with AcOEt. The organic layer was washed with brine, dried over Na$_2$SO$_4$ and evaporated. The residue was purified with silica gel chromatography (CH$_2$Cl$_2$:MeOH:NH$_4$OH=from 95:5:0.25 to 85:12.5:2.5) to obtain the title compound (47 mg, 46% in 2 steps) as a white solid. MS (ESI): 338.2 (MH$^+$).

Example 104

1-[(Z)-5-Aminoadamantan-2-yl]-1',3'-dihydro-2H-spiro[imidazolidine-4,2'-inden]-2-one This material was obtained in analogy to example 103 from 1',3'-dihydro-1-[(Z)-5-hydroxy-adamantan-2-yl]-spiro[imidazolidine-4,2'-[2H]indene]-2-one (1.4 g, obtained in example 100/101) as a white solid (760 mg, 55% in 2 steps). MS (ESI): 338.2 (MH$^+$).

Example 105

N-[(E)-4-(2-Oxo-1',3'-dihydro-1H-spiro[imidazolidine-4,2'-inden]-1-yl)adamantan-1-yl]acetamide A mixture of 1-[(E)-5-aminoadamantan-2-yl]-1',3'-dihydro-2H-spiro[imidazolidine-4,2'-inden]-2-one (100 mg, obtained in examples 103), acetyl chloride (0.02 ml) and triethylamine (0.08 ml) in CH$_2$Cl$_2$ (2.0 ml) was stirred at room temperature for 3 hr. The mixture was poured into saturated NaHCO$_3$ solution, and extracted with AcOEt. The organic layer was washed with saturated NaHCO$_3$ solution, and brine, dried over Na$_2$SO$_4$ and evaporated. The residue was purified with silica gel chromatography (CH$_2$Cl$_2$:MeOH:NH$_4$OH=95:5:0.25) to obtain the title compound (74 mg, 66%) as a white solid. MS (ESI): 380.3 (MH$^+$).

Example 106

N-[(Z)-4-(2-Oxo-1',3'-dihydro-1H-spiro[imidazolidine-4,2'-inden]-1-yl)adamantan-1-yl]acetamide This material was obtained in analogy to example 105 from 1-[(Z)-5-aminoadamantan-2-yl]-1',3'-dihydro-2H-spiro[imidazolidine-4,2'-inden]-2-one (100 mg, obtained in example 104) as a white solid (20 mg, 18%). MS (ESI): 438.3 (M+OAc).

Example 107

N-[(E)-4-(2-Oxo-1',3'-dihydro-1H-spiro[imidazolidine-4,2'-inden]-1-yl)adamantan-1-yl]methanesulfonamide To a mixture of 1-[(E)-5-aminoadamantan-2-yl]-1',3'-dihydro-2H-spiro[imidazolidine-4,2'-inden]-2-one (100 mg, obtained in examples 103) and triethylamine (0.08 ml) in CH$_2$Cl$_2$ (2.0 ml), methanesulfonyll chloride (0.03 ml) was added at 0° C., and the mixture was stirred at room temperature for 2 hr. The mixture was poured into saturated NaHCO$_3$ solution, and extracted with AcOEt. The organic layer was washed with saturated NaHCO$_3$ solution, and brine, dried over Na$_2$SO$_4$ and evaporated. The residue was purified with silica gel chromatography (CH$_2$Cl$_2$:MeOH:NH$_4$OH=95:5:0.25) to obtain the title compound (93 mg, 76%) as a white solid. MS (ESI$^-$): 414.3 ([M−H]$^-$).

Example 108

N-[(Z)-4-(2-Oxo-1',3'-dihydro-1H-spiro[imidazolidine-4,2'-inden]-1-yl)adamantan-1-yl]methanesulfonamide This material was obtained in analogy to example 107 from 1-[(Z)-5-aminoadamantan-2-yl]-1',3'-dihydro-2H-spiro[imidazolidine-4,2'-inden]-2-one (100 mg, obtained in example 104) as a white solid (120 mg, 97%). MS (ESI$^-$): 414.3 ([M−H]$^-$).

Example 109

1,1,1-Trifluoro-N-[(E)-4-(2-oxo-1',3'-dihydro-1H-spiro[imidazolidine-4,2'-inden]-1-yl)adamantan-1-yl]methanesulfonamide To a mixture of 1-[(E)-5-aminoadamantan-2-yl]-1',3'-dihydro-2H-spiro[imidazolidine-4,2'-inden]-2-one (100 mg, obtained in examples 103) and triethylamine (0.08 ml) in CH₂Cl₂ (2.0 ml), trifluoromethanesulfonic anhydride (0.16 ml) was added at room temperature, and the mixture was stirred at room temperature for 24 hr. The mixture was poured into saturated NaHCO₃ solution, and extracted with AcOEt. The organic layer was washed with saturated NaHCO₃ solution, and brine, dried over Na₂SO₄ and evaporated. The residue was purified with silica gel chromatography (CH₂Cl₂: MeOH=98:2) to obtain the title compound (17 mg, 12%) as a white solid. MS (ESI$^-$): 468.2 ([M–H]$^-$).

Example 110

1,1,1-Trifluoro-N-[(Z)-4-(2-oxo-1',3'-dihydro-1H-spiro[imidazolidine-4,2'-inden]-1-yl)adamantan-1-yl]methanesulfonamide This material was obtained in analogy to example 109 from 1-[(Z)-5-aminoadamantan-2-yl]-1',3'-dihydro-2H-spiro[imidazolidine-4,2'-inden]-2-one (100 mg, obtained in example 104) as a white solid (27 mg, 19%). MS (ESI$^-$): 468.3 ([M–H]$^-$).

Example 111 tert-Butyl({[(E)-4-(2-oxo-1',3'-dihydro-1H-spiro[imidazolidine-4,2'-inden]-1-yl)adamantan-1-yl]amino}sulfonyl)carbamate A mixture of 1-[(E)-5-aminoadamantan-2-yl]-1',3'-dihydro-2H-spiro[imidazolidine-4,2'-inden]-2-one (100 mg, obtained in examples 103), triethylamine (0.08 ml) and 4-(dimethylamino)-1-[[[(1,1-dimethylethoxy)carbonyl]amino]sulfonyl]-pyridinium inner salt (90 mg, Organic Letters 3(14), 2001, 2241) in CH₂Cl₂ (2.0 ml) was stirred at room temperature for 19 hr. The mixture was poured into saturated NaHCO₃ solution, and extracted with AcOEt. The organic layer was washed with saturated NaHCO₃ solution, and brine, dried over Na₂SO₄ and evaporated. The residue was purified with silica gel chromatography (CH₂Cl₂:MeOH=98:2) to obtain the title compound (140 mg) as a white solid. MS (ESI$^-$): 515.2 ([M–H]$^-$).

Example 112 tert-Butyl({[(Z)-4-(2-oxo-1',3'-dihydro-1H-spiro[imidazolidine-4,2'-inden]-1-yl)adamantan-1-yl]amino}sulfonyl)carbamate This material was obtained in analogy to example 111 from 1-[(Z)-5-aminoadamantan-2-yl]-1',3'-dihydro-2H-spiro[imidazolidine-4,2'-inden]-2-one (100 mg, obtained in example 104) as a white solid (140 mg, 91%). MS (ESI$^-$): 515.2 ([M–H]$^-$).

Example 113

N-[(E)-4-(2-Oxo-1',3'-dihydro-1H-spiro[imidazolidine-4,2'-inden]-1-yl)adamantan-1-yl]sulfamide To a mixture of tert-butyl({[(E)-4-(2-oxo-1',3'-dihydro-1H-spiro[imidazolidine-4,2'-inden]-1-yl)adamantan-1-yl]amino}sulfonyl)carbamate (100 mg, obtained in examples 111) in CH₂Cl₂ (2.0 ml), trifluoroacetic acid (0.16 ml) was added at 0° C., and the mixture was stirred at room temperature for 2 hr. The mixture was evaporated, diluted with AcOEt and saturated NaHCO₃ solution and extracted with AcOEt. The organic layer was washed with saturated NaHCO₃ solution, and brine, dried over Na₂SO₄ and evaporated. The residue was purified with silica gel chromatography (CH₂Cl₂:MeOH:NH₄OH=95:5:0.25) to obtain the title compound (70 mg, 79%) as a white solid. MS (ESI$^-$): 415.3 ([M–H]$^-$).

Example 114

N-[(Z)-4-(2-Oxo-1',3'-dihydro-1H-spiro[imidazolidine-4,2'-inden]-1-yl)adamantan-1-yl]sulfamide This material was obtained in analogy to example 113 from tert-butyl({[(Z)-4-(2-oxo-1',3'-dihydro-1H-spiro[imidazolidine-4,2'-inden]-1-yl)adamantan-1-yl]amino}sulfonyl)carbamate (120 mg, obtained in examples 112) as a white solid (83 mg, 86%). MS (ESI$^-$): 415.3 ([M–H]$^-$).

Example 115

2-Hydroxy-N-[(E)-4-(2-oxo-1',3'-dihydro-1H-spiro[imidazolidine-4,2'-inden]-1-yl)adamantan-1-yl]acetamide To a mixture of 1-[(E)-5-aminoadamantan-2-yl]-1',3'-dihydro-2H-spiro[imidazolidine-4,2'-inden]-2-one (100 mg, obtained in examples 103), hydroxyacetic acid (27 mg) and 1-hydroxybenzotriazole (41 mg) in DMF (2.0 ml), 1-(3-dimethylaminopropyl)-3-ethylcarbodiimide (70 mg) was added at 0° C. and the mixture was stirred at room temperature for 16 hr. The mixture was poured into saturated NaHCO₃ solution, and extracted with AcOEt. The organic layer was washed with saturated NaHCO₃ solution, and brine, dried over Na₂SO₄ and evaporated. The residue was purified with silica gel chromatography (CH₂Cl₂:MeOH:NH₄OH=95:5:0.25) to obtain the title compound (43 mg, 33%) as a white solid. MS (ESI): 454.4 (M+OAc).

Example 116

2-Hydroxy-N-[(Z)-4-(2-oxo-1',3'-dihydro-1H-spiro[imidazolidine-4,2'-inden]-1-yl)adamantan-1-yl]acetamide This material was obtained in analogy to example 115 from 1-[(Z)-5-aminoadamantan-2-yl]-1',3'-dihydro-2H-spiro[imidazolidine-4,2'-inden]-2-one (100 mg, obtained in example 104) as a white solid (31 mg, 24%). MS (ESI): 454.4 (M+OAc).

Example 117

1-[(E)-4-(2-Oxo-1',3'-dihydro-1H-spiro[imidazolidine-4,2'-inden]-1-yl)adamantan-1-yl]urea To a solution of 1-[(E)-5-aminoadamantan-2-yl]-1',3'-dihydro-2H-spiro[imidazolidine-4,2'-inden]-2-one (100 mg, obtained in examples 103) in CH₂Cl₂ (4.0 ml), trichloroacetyl isocyanate (0.05 ml) was added at 0° C. and the mixture was stirred at 0° C. for 20 min. The mixture was evaporated. The residue was diluted with MeOH (2.0 ml) and 1N NaOH solution (2.96 ml). The mixture was refluxed for 16 hr, and evaporated. The residue was purified with silica gel chromatography (CH₂Cl₂:MeOH:NH₄OH=95:5:0.25) to obtain the title compound (66 mg, 59%) as a white solid. MS (ESI): 381.3 (MH$^+$).

Example 118

1-[(E)-5-(Dimethylamino)adamantan-2-yl]-3-methyl-1',3'-dihydro-2H-spiro[imidazolidine-4,2'-inden]-2-one A mixture of 1-[((E)-5-aminoadamantan-2-yl]-1',3'-dihydro-2H-spiro[imidazolidine-4,2'-inden]-2-one (100 mg, obtained in examples 103), formic acid (1.5 ml) and formaldehyde solution in water (36.5%, 0.3 ml) was stirred at 130° C. for 2 hr. The mixture was poured into saturated $Na_2CO_3$ solution, and extracted with $CH_2Cl_2$. The combined extracts were dried over $Na_2SO_4$ and evaporated. The residue was purified with silica gel chromatography ($CH_2Cl_2$:MeOH=98:2) to obtain the title compound (79 mg, 70%) as a white solid. MS (ESI): 380.5 ($MH^+$).

Example 119

1-[(E)-5-(2,2,2-Trifluoroethoxy)adamantan-2-yl]-1',3'-dihydro-2H-spiro[imidazolidine-4,2'-inden]-2-one A mixture of 11,3'-Dihydro-1-[(E)-5-hydroxy-adamantan-2-yl]-spiro[imidazolidine-4,2'-[2H]indene]-2-one (100 mg, obtained in example 100/101), 2,2,2-trifluoroethyl trifluoromethanesulfonate (1.37 g) and sodium hydride (55% in oil, 64 mg) in DMA (2.0 ml) was stirred at 200° C. for 15 min under microwave condition. The mixture was poured into saturated $NaHCO_3$ solution, and extracted with AcOEt. The organic layer was washed with saturated $NaHCO_3$ solution, and brine, dried over $Na_2SO_4$ and evaporated. The residue was purified with silica gel chromatography ($CH_2Cl_2$:MeOH:$NH_4OH$=95:5:0.25) to obtain the title compound (50 mg, 36%) as a light brown solid. MS (ESI): 421.3 ($MH^+$).

Example 120

1-[(Z)-5-(2,2,2-Trifluoroethoxy)adamantan-2-yl]-1',3'-dihydro-2H-spiro[imidazolidine-4,2'-inden]-2-one This material was obtained in analogy to example 119 from 1',3'-dihydro-1-[(Z)-5-hydroxy-adamantan-2-yl]-spiro[imidazolidine-4,2'-[2H]indene]-2-one (180 mg, obtained in example 100/101) as a white solid (9 mg, 4%). MS (ESI): 421.3 ($MH^+$).

Example 121

3-Chloro-4-(2-oxo-1',3'-dihydro-1H-spiro[imidazolidine-4,2'-inden]-1-yl)benzonitrile Step A] 1-(2-Chloro-4-cyano-phenyl)-3-(2-hydroxymethyl-indan-2-yl)-urea To a mixture of 2-chloro-4-cyano-aniline (150 mg) and N,N-diisopropylethylamine (0.34 ml) in THF (15 ml), a solution of triphosgene (96 mg) in THF (5 ml) was added dropwise at room temperature. The mixture was stirred at room temperature for 30 min. To the mixture, a solution of 2-amino-2,3-dihydro-1H-indene-2-methanol (160 mg, WO 9110644) in THF (2 ml) was added at room temperature. The mixture was stirred for 1 hr at room temperature. The mixture was diluted with AcOEt, washed with water and brine, dried over $MgSO_4$ and evaporated. The residue was triturated with $CH_2Cl_2$ to obtain the title compound (270 mg, 80%) as a white solid.

Step B] 3-chloro-4-(2-oxo-1',3'-dihydro-1H-spiro[imidazolidine-4,2'-inden]-1-yl)benzonitrile To a mixture of 1-(2-Chloro-4-cyano-phenyl)-3-(2-hydroxymethyl-indan-2-yl)-urea (270 mg, obtained in examples 121, step A) and t-BuOK (177 mg) in THF (10 ml), a solution of p-toluenesulfonyl chloride (181 mg) in THF (2 ml) was added dropwise at 0° C. The mixture was stirred at 0° C. for 1 hr. The mixture was diluted with AcOEt, washed with water and brine, dried over $MgSO_4$ and evaporated. The residue was purified with silica gel chromatography ($CH_2Cl_2$:MeOH=from 100:0 to 98:2) to obtain the title compound (120 mg, 47%) as a white solid. MS (EI): 323.9 ($M^+$).

Example 122

3-(5,7-Dihydroxy-adamantan-2-yl)-1,3-diazaspiro[4.4]nonan-2-one

Step A] {1-[(5,7-Dihydroxy-adamantan-2-ylamino)-methyl]-cyclopentyl}-carbamic acid tert-butyl ester To a mixture of 6-amino-adamantane-1,3-diol hydrochloride (258 mg, J. Med. Chem. 50, 2007, 149), N-Boc-cycloleucinal (250 mg) and acetic acid (0.67 ml) in MeOH (5.0 ml), sodium triacetoxyborohydride was added at room temperature. The mixture was stirred at 60° C. for 30 min. The mixture was basified with saturated $NaHCO_3$ solution. The mixture was extracted with AcOEt, washed with brine, dried over $MgSO_4$ and evaporated. The residue was purified with silica gel chromatography ($CH_2Cl_2$:MeOH:$NH_4OH$=from 100:0:0 to 90:9:1) to obtain the title compound (250 mg, 56%) as a white amorphous.

Step B] 6-[(1-Amino-cyclopentylmethyl)-amino]-adamantane-1,3-diol

A mixture of {1-[(5,7-dihydroxy-adamantan-2-ylamino)-methyl]-cyclopentyl}-carbamic acid tert-butyl ester (350 mg, obtained in examples 122, step A) and 6N HCl solution (1.0 ml) in MeOH (2.0 ml) was stirred at room temperature for 16 hr. The mixture was evaporated. The residue was purified with amine-coated silica gel chromatography ($CH_2Cl_2$:MeOH=from 100:0 to 9:1) to obtain the title compound (250 mg, 97%) as a dark brown solid.

Step C] 3-(5,7-Dihydroxy-adamantan-2-yl)-1,3-diazaspiro[4.4]nonan-2-one

To a mixture of 6-[(1-amino-cyclopentylmethyl)-amino]-adamantane-1,3-diol (250 mg, obtained in examples 122, step B) and N,N-diisopropylethylamine (0.62 ml) in $CH_2Cl_2$ (3.0 ml), a solution of triphosgene (90 mg) in THF (1 ml) was added dropwise at room temperature. The mixture was stirred at room temperature for 2 hr. The mixture was poured into saturated $NaHCO_3$ solution, and extracted with AcOEt. The organic layer was washed with brine, dried over $MgSO_4$ and evaporated. The residue was triturated with $CH_2Cl_2$ to obtain the title compound (100 mg, 37%) as a white solid. MS (ESI): 307.1 ($MH^+$).

Example 123

1',3'-Dihydro-1-[(Z)-5-hydroxy-adamantan-2-yl]-3-methyl-spiro[imidazolidine-4,2'-[2H]indene]-2-one This material was obtained in analogy to example 71 from 1',3'-dihydro-1-[(Z)-5-hydroxy-adamantan-2-yl]-spiro[imidazolidine-4,2'-[2H]indene]-2-one (1.2 g, obtained in example 100/101) by treatment with sodium hydride (55% in mineral oil, 0.39 g) and iodomethane (0.24 ml) as a white foam (1.2 g). MS (ESI): 353.2 (MH$^+$).

Example 124

1-[(E)-5-Aminoadamantan-2-yl]-3-methyl-1',3'-dihydro-2H-spiro[imidazolidine-4,2'-inden]-2-one This material was obtained in analogy to example 103 from 1',3'-dihydro-1-[(E)-5-hydroxy-adamantan-2-yl]-3-methyl-spiro[imidazolidine-4,2'-[2H]indene]-2-one (1.1 g, obtained in example 102) as a white solid (362 mg, 33% in 2 steps). MS (ESI): 352.2 (MH$^+$).

Example 125

1-[(Z)-5-Aminoadamantan-2-yl]-3-methyl-1',3'-dihydro-2H-spiro[imidazolidine-4,2'-inden]-2-one This material was obtained in analogy to example 103 from 1',3'-dihydro-1-[(Z)-5-hydroxy-adamantan-2-yl]-3-methyl-spiro[imidazolidine-4,2'-[2H]indene]-2-one (1.2 g, obtained in example 123) as a white solid (362 mg, 28% in 2 steps). MS (ESI): 352.2 (MH$^+$).

Example 126

N-[(E)-4-(3-Methyl-2-oxo-1',3'-dihydro-1H-spiro[imidazolidine-4,2'-inden]-1-yl)adamantan-1-yl]acetamide This material was obtained in analogy to example 105 from 1-[(E)-5-aminoadamantan-2-yl]-3-methyl-1',3'-dihydro-2H-spiro[imidazolidine-4,2'-inden]-2-one (50 mg, obtained in example 124) as a white solid (56 mg, 100%). MS (ESI): 394.3 (MH$^+$).

Example 127

N-[(Z)-4-(3-Methyl-2-oxo-1',3'-dihydro-1H-spiro[imidazolidine-4,2'-inden]-1-yl)adamantan-1-yl]acetamide This material was obtained in analogy to example 105 from 1-[(Z)-5-aminoadamantan-2-yl]-3-methyl-1',3'-dihydro-2H-spiro[imidazolidine-4,2'-inden]-2-one (50 mg, obtained in example 125) as a white solid (40 mg, 71%). MS (ESI): 394.3 (MH$^+$).

Example 128

N-[(E)-4-(3-Methyl-2-oxo-1',3'-dihydro-1H-spiro[imidazolidine-4,2'-inden]-1-yl)adamantan-1-yl]methanesulfonamide This material was obtained in analogy to example 107 from 1-[(E)-5-aminoadamantan-2-yl]-3-methyl-1',3'-dihydro-2H-spiro[imidazolidine-4,2'-inden]-2-one (50 mg, obtained in example 124) as a white solid (50 mg, 82%). MS (ESI): 488.2 (M+OAc).

Example 129

N-[(Z)-4-(3-Methyl-2-oxo-1',3'-dihydro-1H-spiro[imidazolidine-4,2'-inden]-1-yl)adamantan-1-yl]methanesulfonamide This material was obtained in analogy to example 107 from 1-[(Z)-5-aminoadamantan-2-yl]-3-methyl-1',3'-dihydro-2H-spiro[imidazolidine-4,2'-inden]-2-one (50 mg, obtained in example 125) as a white foam (58 mg, 95%). MS (ESI): 488.2 (M+OAc).

Example 130

1,1,1-Trifluoro-N-[(E)-4-(3-methyl-2-oxo-1',3'-dihydro-1H-spiro[imidazolidine-4,2'-inden]-1-yl)adamantan-1-yl]methanesulfonamide This material was obtained in analogy to example 109 from 1-[(E)-5-aminoadamantan-2-yl]-3-methyl-1',3'-dihydro-2H-spiro[imidazolidine-4,2'-inden]-2-one (95 mg, obtained in example 124) as a light brown solid (95 mg, 72%). MS (ESI$^-$): 482.3 ([M−H]$^-$).

Example 131

1,1,1-Trifluoro-N-[(Z)-4-(3-methyl-2-oxo-1',3'-dihydro-1H-spiro[imidazolidine-4,2'-inden]-1-yl)adamantan-1-yl]methanesulfonamide This material was obtained in analogy to example 109 from 1-[(Z)-5-aminoadamantan-2-yl]-3-methyl-1',3'-dihydro-2H-spiro[imidazolidine-4,2'-inden]-2-one (70 mg, obtained in example 125) as a light brown solid (20 mg, 21%). MS (ESI$^-$): 482.3 ([M−H]$^-$).

Example 132

N-[(E)-4-(3-Methyl-2-oxo-1',3'-dihydro-1H-spiro[imidazolidine-4,2'-inden]-1-yl)adamantan-1-yl]sulfamide This material was obtained in analogy to example 111 and example 113 from 1-[(E)-5-aminoadamantan-2-yl]-3-methyl-1',3'-dihydro-2H-spiro[imidazolidine-4,2'-inden]-2-one (50 mg, obtained in example 124) as a white foam (48 mg, 78%). MS (ESI): 489.3 (M+OAc).

Example 133

N-[(Z)-4-(3-Methyl-2-oxo-1',3'-dihydro-1H-spiro[imidazolidine-4,2'-inden]-1-yl)adamantan-1-yl]sulfamide This material was obtained in analogy to example 111 and example 113 from 1-[(Z)-5-aminoadamantan-2-yl]-3-methyl-1',3'-dihydro-2H-spiro[imidazolidine-4,2'-inden]-2-one (50 mg, obtained in example 125) as a white solid (36 mg, 59%). MS (ESI): 489.3 (M+OAc).

Example 134

2-Hydroxy-N-[(E)-4-(3-methyl-2-oxo-1',3'-dihydro-1H-spiro[imidazolidine-4,2'-inden]-1-yl)adamantan-1-yl]acetamide This material was obtained in analogy to example 115 from 1-[(E)-5-aminoadamantan-2-yl]-3-methyl-1',3'-dihydro-2H- spiro[imidazolidine-4,2'-inden]-2-one (50 mg, obtained in example 124) as a white solid (8 mg, 14%). MS (ESI): 410.3 (MH+).

Example 135

2-Hydroxy-N-[(Z)-4-(3-methyl-2-oxo-1',3'-dihydro-1H-spiro[imidazolidine-4,2'-inden]-1-yl)adamantan-1-yl]acetamide This material was obtained in analogy to example 115 from 1-[(Z)-5-aminoadamantan-2-yl]-3-methyl-1',3'-dihydro-2H-spiro[imidazolidine-4,2'-inden]-2-one (50 mg, obtained in example 125) as a white solid (16 mg, 27%). MS (ESI): 410.5 (MH+).

Example 136

1-[(E)-4-(3-Methyl-2-oxo-1',3'-dihydro-1H-spiro[imidazolidine-4,2'-inden]-1-yl)adamantan-1-yl]urea This material was obtained in analogy to example 117 from 1-[(E)-5-aminoadamantan-2-yl]-3-methyl-1',3'-dihydro-2H-spiro[imidazolidine-4,2'-inden]-2-one (50 mg, obtained in example 124) as a white solid (52 mg, 84%). MS (ESI): 395.4 (MH+).

Example 137

1-[(Z)-4-(3-Methyl-2-oxo-1',3'-dihydro-1H-spiro[imidazolidine-4,2'-inden]-1-yl)adamantan-1-yl]urea This material was obtained in analogy to example 117 from 1-[(Z)-5-aminoadamantan-2-yl]-3-methyl-1',3'-dihydro-2H-spiro[imidazolidine-4,2'-inden]-2-one (50 mg, obtained in example 125) as a white solid (40 mg, 71%). MS (ESI): 395.4 (MH+).

Example 138

Methyl (E/Z)-4-(2-oxo-1',3'-dihydro-1H-spiro[imidazolidine-4,2'-inden]-1-yl)adamantane-1-carboxylate This material was prepared in analogy to example 100/101 from 2-amino-2,3-dihydro-1 H-indene-2-methanamine, 4-oxo-adamantane-1-carboxylic acid methyl ester (preparation described in: J. Org. Chem.; 1983; 1099) by reductive amination with NaBH$_4$ followed by ring closure with bis-(trichloromethyl)-carbonate as an off-white solid. MS (ESI): 381.3 (MH+). The (E)- and (Z)-isomers can be separated by chromatography on silica gel.

Example 139

(E/Z)-4-(2-oxo-1',3'-dihydro-1H-spiro[imidazolidine-4,2'-inden]-1-yl)adamantane-1-carboxylic acid A solution of Methyl (E/Z)-4-(2-oxo-1',3'-dihydro-1H-spiro[imidazolidine-4,2'-inden]-1-yl)adamantane-1-carboxylate (70 mg) in methanol (5 mL) and 0.55 ml of 1 N aqueous NaOH was heated at reflux for 2.5 h until the reaction was completed according to TLC analysis. The reaction mixture was cooled to room temperature, acidified with 1N aqueous HCL and then partitioned between methylene chloride and water. The layers were separated, the organic layer was washed with water, dried over MgSO$_4$, filtered and evaporated to give the title compound (66 mg) as an off-white solid. The (E)- and (Z)-isomers can be separated by chromatography on silica gel.

Example 140

(E/Z)-4-(2-oxo-1',3'-dihydro-1H-spiro[imidazolidine-4,2'-inden]-1-yl)adamantane-1-carboxamide A suspension of (E/Z)-4-(2-oxo-1',3'-dihydro-1H-spiro[imidazolidine-4,2'-inden]-1-yl)adamantane-1-carboxylic acid (60 mg) in methylene chloride (4 ml) was treated with 1-hyrdoxybenzotriazole (30 mg) followed by 1-ethyl-3-(3-dimethylaminopropyl)carbodiimide monohydrochloride EDCI (44 mg) and then stirred for 1.25 h at RT. Then 3 ml of 25% aqueous ammonia were added and stirring was continued for 12 h. The reaction mixture was then partitioned between methylene chloride and water, the layers were separated, the organic layer was washed with water, dried over MgSO$_4$, filtered and evaporated to give the title compound as a light grey solid. MS (ESI): 366.1 (MH+).

From the mixture of diastereomers, the (E)-isomer was separated from the (Z)-isomer by flash chromatography on silica gel as the more polar isomer. White crystalline solid, MS (ESI): 366.0 (MH+).

Example 141

1-[5-(E/Z)-(hydroxymethyl)adamantan-2-yl]-1',3'-dihydro-2H-spiro[imidazolidine-4,2'-inden]-2-one A solution Methyl (E/Z)-4-(2-oxo-1',3'-dihydro-1H-spiro[imidazolidine-4,2'-inden]-1-yl)adamantane-1-carboxylate (70 mg,) in ethanol/THF (each 3 mL) was treated at room temperature with CaCl$_2$ (20 mg) and NaBH$_4$ (14 mg), stirred for 2 h at RT, further 20 mg of CaCl$_2$ (20 mg) and NaBH$_4$ (14 mg) were added and stirring was continued for 12 h until the reaction was complete (TLC monitoring). The reaction mixture was partitioned between methylene chloride and aqueous NH4Cl solution, the layers were separated, and the organic layer was washed with water, dried over MgSO$_4$, filtered and evaporated. The crude product was crystallized from MeOH/CH$_2$CH$_2$/diethyl ether to give the title compound (52 mg) as white solid. MS (ESI): 353.2 (MH+). The (E)- and (Z)-isomers can be separated by chromatography on silica gel.

Example 142

(E/Z)-4-(2-Oxo-1,3-diaza-spiro[4.4]non-3-yl)-adamantane-1-carboxylic acid methyl ester This material was prepared in analogy to example 100/101 from 1-aminomethyl-cyclopentylamine, 4-oxo-adamantane-1-carboxylic acid methyl ester by reductive amination with NaBH$_4$ followed by ring closure with bis-(trichloromethyl)-carbonate as a white crystalline solid. MS (ESI): 333.1 (MH+). The (E)- and (Z)-isomers can be separated by chromatography on silica gel.

Example 143

(E/Z)-4-(2-Oxo-1,3-diaza-spiro[4.4]non-3-yl)-adamantane-1-carboxylic acid

This material was prepared in analogy to example 139 from (E/Z)-4-(2-oxo-1,3-diaza-spiro[4.4]non-3-yl)-adamantane-1-carboxylic acid methyl ester as a white crystalline solid.

MS (ESI⁻): 317.2 ([M−H]⁻). The (E)- and (Z)-isomers can be separated by chromatography on silica gel.

Example 144

(E/Z)-4-(2-Oxo-1,3-diaza-spiro[4.4]non-3-yl)-adamantane-1-carboxylic acid amide

This material was prepared in analogy to example 140 from (E/Z)-4-(2-Oxo-1,3-diaza-spiro[4.4]non-3-yl)-adamantane-1-carboxylic acid as a crystalline white solid. MS (ESI): 318.3 (MH⁺). The (E)- and (Z)-isomers can be separated by chromatography on silica gel.

Example 145

3-[(E/Z)-5-Hydroxymethyl-adamantan-2-yl]-1,3-diaza-spiro[4.4]nonan-2-one

This material was prepared in analogy to example 141 from (E/Z)-4-(2-Oxo-1,3-diaza-spiro[4.4]non-3-yl)-adamantane-1-carboxylic acid methyl ester as a white solid. MS (ESI): 305.1 (MH⁺). The (E)- and (Z)-isomers can be separated by chromatography on silica gel.

Example 146

(E/Z)-4-(1-Ethyl-2-oxo-1,3-diaza-spiro[4.4]non-3-yl)-adamantane-1-carboxylic acid methyl ester This material was prepared in analogy to example 100/101 from (1-aminomethyl-cyclopentyl)-ethyl-amine, 4-oxo-adamantane-1-carboxylic acid methyl ester by reductive amination with NaBH$_4$ followed by ring closure with bis-(trichloromethyl)-carbonate as a colorless viscous oil. MS (ESI): 361.3 (MH⁺). The (E)- and (Z)-isomers can be separated by chromatography on silica gel.

Preparation of (1-Aminomethyl-cyclopentyl)-ethyl-amine

This material was obtained in analogy to example 65 step a, from 1-ethylamino-cyclopentanecarbonitrile (7.5 g), synthesis described in: J. Med. Chem.; 1969; 473, by reduction with diisobutylaluminiumhydride (20% in toluene, 282.6 mL) as an oil (6.55 g) and directly used in the next reaction step.

Example 147

(E/Z)-4-(1-Ethyl-2-oxo-1,3-diaza-spiro[4.4] non-3-yl)-adamantane-1-carboxylic acid This material was prepared in analogy to example 139 (E/Z)-4-(1-ethyl-2-oxo-1,3-diaza-spiro[4.4]non-3-yl)-adamantane-1-carboxylic acid methyl ester as a colorless viscous oil. MS (ESI⁻): 345.1 ([M−H]⁻). The (E)- and (Z)-isomers can be separated by chromatography on silica gel.

Example 148

(E/Z)-4-(2-Oxo-1,3-diaza-spiro[4.4]non-3-yl)-adamantane-1-carboxylic acid amide

This material was prepared in analogy to example 140 from (E/Z)-4-(1-ethyl-2-oxo-1,3-diaza-spiro[4.4]non-3-yl)-adamantane-1-carboxylic acid as crystalline white solid. MS (ESI): 346.2 (MH⁺).

Example 149

3-(3-Chloro-benzyl)-1-((E)-5-hydroxy-adamantan-2-yl)-4,4-dimethyl-imidazolidin-2-one This material was prepared in analogy to example 89 from 1-[(E)-5-hydroxy-adamantan-2-yl]-4,4-dimethyl-imidazolidin-2-one by alkylation with 3-chlorobenzyl bromide as a white powder. MS (ESI): 389.3 (MH⁺).

Example 150

1-((E)-5-Hydroxy-adamantan-2-yl)-4,4-dimethyl-3-(3-trifluoromethoxy-benzyl)-imidazolidin-2-one This material was prepared in analogy to example 89 from 1-[(E)-5-hydroxy-adamantan-2-yl]-4,4-dimethyl-imidazolidin-2-one by alkylation with 3-(trifluoromethoxy)benzyl bromide as a colorless oil. MS (ESI): 439.3 (MH⁺).

Example 151

(R)-3-(4-Bromo-benzyl)-4-cyclopropyl-1-((E)-5-hydroxy-adamantan-2-yl)-4-methyl-imidazolidin-2-one This material was prepared in analogy to example 89 from (R)-4-cyclopropyl-1-[(E)-5-hydroxy-adamantan-2-yl]-4-methyl-imidazolidin-2-one, obtained in example 69, after separation of the enantiomers by chiral HPLC and assignment of the absolute configuration by x-ray crystallography, by alkylation with 4-bromobenzyl bromide a white foam. MS (ESI): 459.3 (MH⁺).

Example 152 and 153

N-[(E)-4-(4-Isopropyl-3-methyl-2-oxo-imidazolidin-1-yl)-adamantan-1-yl]-acetamide and N-[(Z)-4-(4-Isopropyl-3-methyl-2-oxo-imidazolidin-1-yl)-adamantan-1-yl]-acetamide These compounds were prepared in analogy to example 100/101 from 3,N²-Dimethyl-butane-1,2-diamine, N-(4-oxo-adamantan-1-yl)-acetamide (for synthesis: patent, FR 1511936; 1966) by reductive amination with NaBH$_4$ followed by ring closure with bis-(trichloromethyl)-carbonate. The (E/Z) isomers were separated by flash chromatography on silica gel with AcOEt/MeOH (100:2.5 to 90:10) as eluant. Colorless solids, MS (ESI): 334,5 (MH⁺).

Example 154

5-Benzyl-7-((E/Z)-5-hydroxy-adamantan-2-yl)-2-oxa-5,7-diaza-spiro[3.4]octan-6-one These compounds were prepared in analogy to example 100/101 from (3-aminomethyl-oxetan-3-yl)-benzyl-amine, 5-hydroxy-2-adamantanone by reductive amination with NaBH$_4$ followed by ring closure with bis-(trichloromethyl)-carbonate. The (E/Z) isomers were separated by flash chromatography on silica gel with AcOEt/MeOH (100:2.5 to 90:10) as eluant. Colorless solids, MS (ESI): 369.0 (MH⁺). The (E)- and (Z)-isomers can be separated by chromatography on silica gel.

Preparation of the Starting Material

Step a: (3-Aminomethyl-oxetan-3-yl)-dibenzyl-amine

To 3-Dibenzylamino-oxetane-3-carbonitrile (156 mg) (prepared by Strecker synthesis in analogy to example 83/84, step a, from oxetan-3-one, dibenzyl-amine and trimethylsilyl cyanide) in methanol (10 ml) was added a catalytic amount of Raney nickel and the reaction mixture was then stirred at RT under an atmosphere of $H_2$ for 8 h. The catalyst was removed by filtration, the filtrate concentrated under reduced pressure to provide the title compound (170 mg) as off-white solid, MS (ESI): 283.17 (MH⁺).

Step b: (3-Aminomethyl-oxetan-3-yl)-benzyl-amine

To (3-Aminomethyl-oxetan-3-yl)-dibenzyl-amine in methanol (10 ml) was added a catalytic amount of 10% Pd/C and the reaction mixture was then stirred at RT under an atmosphere of $H_2$ for 8 h. The catalyst was removed by filtration, the filtrate concentrated under reduced pressure to provide the title compound (90 mg) as colorless oil, MS (EI): 192 (M⁺).

Example 155

4-(1-Cyclopropyl-2-oxo-1,3-diaza-spiro[4.6]undec-3-yl)-benzamide

Step A: 1-Cyclopropylamino-cycloheptanecarbonitrile 5 g (44.57 mmol) of Cycloheptanone and 4.1 g of potassium cyanide were added to a solution of 4.38 ml (62.4 mmol) cyclopropylamine and 3.56 ml (62.4 mmol) of acetic acid in 50 ml MeOH. The reaction-mixture was stirred for 24 h, and then it was concentrated under reduced pressure, taken up in EtOAc and washed with water. The organic layer was concentrated under reduced pressure to give 6.84 g almost pure 1-Cyclopropylamino-cycloheptanecarbonitrile. MS (ESI): 179.3 (M+H)

Step B: 4-Isocyanato-benzoic acid ethyl ester

To a solution of 1.5 g (9.08 mmol) 4-amino-benzoic acid ethyl ester in 16 ml of THF was added 0.621 ml (5 mmol) of trichloromethyl chloroformate. The reaction mixture was stirred under reflux for 1 h and then concentrated under reduced pressure to dryness. The crude 4-Isocyanato-benzoic acid ethyl ester was used in the next step.

Step C: 4-(1-Cyclopropyl-2,4-dioxo-1,3-diaza-spiro[4.6]undec-3-yl)-benzoic acid ethyl ester 1.62 g (9.08 mmol) of 1-Cyclopropylamino-cycloheptanecarbonitrile and the crude 4-Isocyanato-benzoic acid ethyl ester in 15 ml THF were stirred for 3 h at RT and then 3.8 ml (27.3 mmol) of triethylamin was added. The stirring was continued for 24 h and then the reaction mixture was concentrated under reduced pressure to dryness. To the dry residue was added 17 ml of 2N HCl and 33 ml of Ethanol and the whole was refluxed for 1 h. The reaction mixture was taken up in EtOAc and washed with water. The organic layers were concentrated under reduced pressure and the crude product was purified by chromatography over silica gel with EtOAc/Heptan 1:2 to give 265 mg of pure 4-(1-Cyclopropyl-2,4-dioxo-1,3-diaza-spiro[4.6]undec-3-yl)-benzoic acid ethyl ester. MS (ESI): 357.3 (MH⁺).

Step D and E: 4-(1-Cyclopropyl-2-oxo-1,3-diaza-spiro[4.6]undec-3-yl)-benzoic acid ethyl ester To 228 mg (0.61 mmol) of 4-(1-Cyclopropyl-2,4-dioxo-1,3-diaza-spiro[4.6]undec-3-yl)-benzoic acid ethyl ester dissolved in 4 ml THF/Methanol 1:1 was added under ice-cooling 70 mg (1.84 mmol) of sodium borohydride. The reaction mixture was stirred for 2 h at RT and then additional 70 mg of sodium borohydride was added and the stirring was continued over night. The whole was concentrated under reduced pressure to dryness and the residue was dissolved in 2 ml of trifluoroacetic acid. To this ice-chilled solution was added again 70 mg of sodium borohydride. The reaction mixture was stirred for 1 h at RT and then the trifluoroacetic acid was removed under reduced pressure. The residue was taken up in EtOAc and washed with sodium bicarbonate solution and water. The crude product was purified by chromatography over silica gel with DCM/EtOAc 9:1 to give 103 mg of pure 4-(1-Cyclopropyl-2-oxo-1,3-diaza-spiro[4.6]undec-3-yl)-benzoic acid ethyl ester. MS (ESI): 357.3 (MH⁺).

Step F: 4-(1-Cyclopropyl-2-oxo-1,3-diaza-spiro[4.6]undec-3-yl)-benzamide

A solution of 76 mg (2.1 mmol) 4-(1-Cyclopropyl-2-oxo-1,3-diaza-spiro[4.6]undec-3-yl)-benzoic acid ethyl ester in 2 ml THF/Methanol 1.1 was treated with 0.5 ml of 1N LiOH. After stirring for 3 h the reaction mixture was acidified with 1N HCL, taken up in EtOAc and washed with water to give 65.5 mg of pure 4-(1-cyclopropyl-2-oxo-1,3-diaza-spiro[4.6]undec-3-yl)-benzoic acid MS (API): 327.5 (M–H). A solution of 47 mg (1.3 mmol) 4-(1-cyclopropyl-2-oxo-1,3-diaza-spiro[4.6]undec-3-yl)-benzoic acid and 27 mg (0.16 mmol) of 1,1-carbonyl diimidazole in 1 ml of THF was stirred under reflux for 1 h, then 32 mg (0.4 mmol) of Ammonium acetate was added and the stirring under reflux was continued for another 2 h. The reaction mixture was taken up in EtOAc and washed with 1N HCL and water. The crude product was crystallized in Ether/Heptan to give 25 mg of pure 4-(1-Cyclopropyl-2-oxo-1,3-diaza-spiro[4.6]undec-3-yl)-benzamide. MS (ESI): 328.4 (MH⁺).

Example 156

1-Cyclopropyl-3-(4-methoxy-2-trifluoromethyl-phenyl)-1,3-diaza-spiro[4.6]undecan-2-one This compound was synthesized in analogy to example 155, (step A to E). In step B 4-methoxy-2-trifluoromethyl-phenylamine was starting material in place of 4-amino-benzoic acid ethyl ester.

In step D, the first reduction step was performed with DIBALH in THF in place of sodium borohydride in THF/MeOH. 1-Cyclopropyl-3-(4-methoxy-2-trifluoromethylphenyl)-1,3-diaza-spiro[4.6]undecan-2-one was obtained as light brown crystals (327 mg). MS (ESI): 383.3 (MH⁺).

Example 157

4-(3-Cyclopropyl-4-isopropyl-2-oxo-imidazolidin-1-yl)-benzamide

This compound was synthesized in analogy to example 155 (step A to F). In step A, 2-mMethyl-propionaldehyde was the starting material in place of cycloheptanone. 4-(3-Cyclopropyl-4-isopropyl-2-oxo-imidazolidin-1-yl)-benzamide was isolated as a white solid. MS (ESI): 288.0 (MH⁺).

Example 158

4-(1-Cyclopropyl-3-(4-methoxy-phenyl)-1,3-diaza-spiro[4.5]decan-2-one 4-(1-Cyclopropyl-3-(4-methoxy-phenyl)-1,3-diaza-spiro[4.5]decan-2-one was produced in analogy to example 155 (step A to E) with the modification that in step A, cyclohexanone was starting material in place of cycloheptanone, and in step B 4-Methoxy-phenylamine was used in place of 4-Amino-benzoic acid ethyl ester. The product was obtained as a colorless and viscous oil. MS (ESI): 301.3 (MH⁺).

Example 159

4-(1-Cyclopropyl-3-(4-hydroxy-phenyl)-1,3-diaza-spiro[4.5]decan-2-one 150 mg (0.5 mmol) of 1-Cyclopropyl-3-(4-methoxy-phenyl)-1,3-diaza-spiro[4.5]decan-2-one, product of example 158, was treated with 1.5 ml (1.5 mmol) of boron trichloride (1.0M solution in Heptane). The reaction mixture was stirred at RT for 20 h. The reaction mixture was then taken up in Ethyl acetate and washed with 1N HCl and water. The raw product was purified by chromatography with DCM/Ethyl acetate 9:1 to 4:1 giving 30 mg of a light brown solid. MS (ESI): 287.0 (MH⁺).)

Example 160

3-(3-Chloro-4-methoxy-phenyl)-1-cyclopropyl-1,3-diaza-spiro[4.5]decan-2-one

This material was produced in analogy to example 158, with the difference that in step B was used 3-chloro-4-methoxy-phenylamine in place of 4-methoxy-phenylamine. The product was obtained as white crystals. MS (ESI): 335.4 (MH⁺).

Example 161

3-(3-Chloro-4-hydroxy-phenyl)-1-cyclopropyl-1,3-diaza-spiro[4.5]decan-2-one

Example 161 was produced from 3-(3-chloro-4-methoxy-phenyl)-1-cyclopropyl-1,3-diaza-spiro[4.5]decan-2-on (Example 160) in analogy to the procedure described in example 159 providing pure 3-(3-Chloro-4-hydroxy-phenyl)-1-cyclopropyl-1,3-diaza-spiro[4.5]decan-2-one as a white foam MS (ESI): 321.1 (MH⁺).

Example 162

1-Cyclopropyl-3-(2,4-dimethoxy-phenyl)-1,3-diaza-spiro[4.5]decan-2-one

This compound was synthesized in analogy to example 158 with the difference that in step B 2,4-dimethoxy-phenylamine was used in place of 4-methoxy-phenylamine as starting material. 1-Cyclopropyl-3-(2,4-dimethoxy-phenyl)-1,3-diaza-spiro[4.5]decan-2-one was isolated as a white crystalline product. MS (ESI): 331.2 (MH⁺).

Example 163

1-Cyclopropyl-3-(2-trifluoromethyl-phenyl)-1,3-diaza-spiro[4.5]decan-2-one

This compound was synthesized in analogy to example 158 with the difference that in step B, 2-trifluoromethyl-phenylamine was used in place of 4-methoxy-phenylamine as starting material. 1-cyclopropyl-3-(2-trifluoromethyl-phenyl)-1,3-diaza-spiro[4.5]decan-2-one was isolated as a colorless semisolid product. MS (ESI): 339.1 (MH⁺).

Example 164

3-Cyclopropyl-1-(2,5-dichloro-phenyl)-4-isopropyl-imidazolidin-2-one

This compound was synthesized in analogy to example 155 (step A to E). In step A, 2-methyl-propionaldehyde was the starting material in place of cycloheptanone and in step B, 2,5-dichloro-phenylamine was used in place of 4-Amino-benzoic acid ethyl ester. 3-Cyclopropyl-1-(2,5-dichloro-phenyl)-4-isopropyl-imidazolidin-2-one was isolated as a light brown viscous oil. MS (API): 313.23 (M)

Example 165

3-Cyclopropyl-4-isopropyl-1-(4-methoxy-phenyl)-imidazolidin-2-one

This compound was synthesized in analogy to example 155 (step A to E). In step A, 2-methyl-propionaldehyde was the starting material in place of cycloheptanone and in step B, 4-methoxy-phenylamine was used in place of 4-amino-benzoic acid ethyl ester. 3-Cyclopropyl-4-isopropyl-1-(4-methoxy-phenyl)-imidazolidin-2-one was isolated as light yellow viscous oil. MS (ESI): 275.3 (MH⁺).

Example 166

3-Cyclopropyl-4-isopropyl-1-(4-hydroxy-phenyl)-imidazolidin-2-one

This compound was produced from 3-Cyclopropyl-4-isopropyl-1-(4-methoxy-phenyl)-imidazolidin-2-one (Example 165) in analogy to the procedure described in example 159.3-Cyclopropyl-4-isopropyl-1-(4-hydroxy-phenyl)-imidazolidin-2-one was isolated as a colorless foam. MS (ESI): 261.1 (MH⁺).

Example 167

3-Cyclopropyl-1-(3-fluoro-4-methoxy-phenyl)-4-isopropyl-imidazolidin-2-one

This compound was synthesized in analogy to example 155 (step A to E). In step A, 2-methyl-propionaldehyde was the starting material in place of cycloheptanone and in step B, 3-fluoro-4-Methoxy-phenylamine was used in place of 4-Amino-benzoic acid ethyl ester. 3-Cyclopropyl-4-isopropyl-1-(3-fluoro-4-methoxy-phenyl)-imidazolidin-2-one was isolated as a light yellow solid. MS (ESI): 293.3 (MH$^+$).

Example 168

1-Cyclopropyl-3-(4-methoxy-phenyl)-8-phenyl-1,3-diaza-spiro[4.5]decan-2-one

This compound was synthesized in analogy to example 155 (step A to E). In step A, 4-phenyl-cyclohexanone was the starting material in place of cycloheptanone and in step B, 4-methoxy-phenylamine was used in place of 4-Amino-benzoic acid ethyl ester. 1-Cyclopropyl-3-(4-methoxy-phenyl)-8-phenyl-1,3-diaza-spiro[4.5]decan-2-one was isolated as a colorless waxy solid. MS (ESI): 377.4 (MH$^+$).

Example 169

4-Benzyl-3-cyclopropyl-1-(2,5-dichloro-phenyl)-imidazolidin-2-one

This compound was synthesized in analogy to example 155 (step A to E). In step A, phenyl-acetaldehyde was starting material in place of cycloheptanone and in step B, 2,5-dichloro-phenyl amine was used in place of 4-amino-benzoic acid ethyl ester. 4-Benzyl-3-cyclopropyl-1-(2,5-dichloro-phenyl)-imidazolidin-2-one was isolated as a light yellow waxy solid. MS (EI): 361.0 (M$^+$).

Example 170

3-Benzyl-1-(2-chloro-5-fluoro-phenyl)-4-isopropyl-imidazolidin-2-one

This compound was synthesized in analogy to example 155 (step A to E). In step A, 2-methyl-propionaldehyde was starting material in place of cycloheptanone and ammonium acetate in place of cyclopropylamino acetate. In step B, 2-chloro-5-fluoro-phenyl amine was used in place of 4-Amino-benzoic acid ethyl ester. The pure 3-(2-chloro-5-fluoro-phenyl)-5-isopropyl-imidazolidine-2,4-dione that resulted from this procedure was then benzylated by stirring of 300 mg (1.11 mmol) of 3-(2-Chloro-5-fluoro-phenyl)-5-isopropyl-imidazolidine-2,4-dione with 141 ml (1.16 mmol) of benzyl bromide and 51 mg (1.16 ml) of sodium hydride (55% in oil) in 5 ml DMF for 3 h at RT. The reaction mixture was then taken up in ethyl acetate and was washed with 1N HCl and water. The crude product was purified by silica gel chromatography with Ethyl acetate/Heptane 1:3 to give 306 mg of pure 1-benzyl-3-(2-chloro-5-fluoro-phenyl)-5-isopropyl-imidazolidine-2,4-dione that was reduced with the same procedure described in step D and E to give pure 3-benzyl-1-(2-chloro-5-fluoro-phenyl)-4-isopropyl-imidazolidin-2-one as a colorless viscous oil MS (ESI): 347.3 (MH$^+$).

Example 171

1-Allyl-3-(2-chloro-5-fluoro-phenyl)-5-isopropyl-imidazolidine-2-one

This compound was produced in analogy to example 170 with the modification that allyl bromide was the alkylating agent in place of Benzyl bromide. 1-Allyl-3-(2-chloro-5-fluoro-phenyl)-5-isopropyl-imidazolidine-2-one was isolated as colorless oil. MS (ESI): 297.4 (MH$^+$).

Example 172

1-Benzyl-3-(2,5-dichloro-phenyl)-5-isopropyl-imidazolidine-2-one

This compound was produced in analogy to example 170 with the modification that in step B, 2,5-dichloro phenyl amine was used in place of 2-chloro-5-fluoro-phenyl amine. 1-Benzyl-3-(2,5-dichloro-phenyl)-5-isopropyl-imidazolidine-2-one was isolated as a colorless viscous oil MS (ESI): 363.3 (MH$^+$).

Example 173

1-(2,5-Dichloro-phenyl)-3-(4-fluoro-benzyl)-4-isopropyl-imidazolidin-2-one

This compound was produced in analogy to example 170 with the modifications that in step B, 2,5-Dichloro phenyl amine was used in place of 2-chloro-5-fluoro-phenyl amine and that 4-fluoro-benzyl bromide was the alkylating agent in place of Benzyl bromide. 1-(2,5-Dichloro-phenyl)-3-(4-fluoro-benzyl)-4-isopropyl-imidazolidin-2-one was isolated as a colorless viscous oil MS (EI): 381.1 (M$^+$).

Example 174

1-(4-methoxyphenyl)-3-methyl-1',3'-dihydro-2H-spiro[imidazolidine-4,2'-inden]-2-one This compound was produced in analogy to example 170 with the modifications that in step A indan-2-one was starting material in place of cycloheptanone and that in step B, 4-methoxy-phenyl amine was used in place of 2-chloro-5-fluoro-phenyl amine and that Iodomethane was the alkylating agent in place of Benzyl bromide. 1-(4-methoxyphenyl)-3-methyl-1',3'-dihydro-2H-spiro[imidazolidine-4,2'-inden]-2-one was obtained as a white solid MS (ESI): 309.0 (MH$^+$).

Example 175

1-(4-hydroxyphenyl)-3-methyl-1',3'-dihydro-2H-spiro[imidazolidine-4,2'-inden]-2-one Example 175 was produced out of 1-(4-methoxyphenyl)-3-methyl-1',3'-dihydro-2H-spiro[imidazolidine-4,2'-inden]-2-one (Example 174) in analogy to the procedure described in example 159 providing pure 1-(4-hydroxyphenyl)-3-methyl- 1',3'-dihydro-2H-spiro[imidazolidine-4,2'-inden]-2-one as alight brown solid. MS (ESI): 295.1 (MH+).

Example 176

(E/Z)-4-[4-(3-Chloro-phenyl)-4-methyl-2-oxo-imidazolidin-1-yl]-adamantane-1-carboxylic acid methyl ester Step A] 2-Amino-2-(3-chloro-phenyl)-propionitrile A mixture of sodium cyanide (25.4 g), ammonium chloride (27.6 g) and aqueous ammonia (35 mL of a 25% solution) was stirred at room temperature for five minutes. A solution of 3-chloroacetophenone (10 g) in ethanol was added to the above mixture. The flask was sealed with glass stopper and stirred at room temperature for 24 h. Reaction was monitored by TLC. After completion, the reaction mixture was filtered through Celite to remove inorganic salts. The filtrate was treated with water (100 mL) and extracted with dichloromethane (3×100 mL), the combined organic phases were dried over anhydrous sodium sulphate, filtered and concentrated to 20 mL. This solution was filtered through neutral alumina to remove some colored impurities. Evaporation of dichloromethane yielded the crude Strecker product 2-amino-2-(3-chloro-phenyl)-propionitrile (8.0 g).

Step B] 2-(3-Chloro-phenyl)-propane-1,2-diamine

A solution of compound 2-amino-2-(3-chloro-phenyl)-propionitrile (8.0 g) in toluene (60 mL) was cooled to −78° C. and DIBAL-H solution (132 mL of a 1M solution in toluene) was added to it drop wise under nitrogen. The reaction mixture was slowly warmed to room temperature and then left at stirring for 17 h. Reaction was monitored by TLC. After completion, the reaction mixture was quenched with 30 mL methanol and then 100 mL water. All solvents were evaporated and the crude mass was taken in 50 mL water and acidified to pH=1 with 1M HCl. Organic impurities were extracted with ethyl acetate and the aqueous layer was basified to pH=14 with 30% NaOH solution. The free diamine, 2-(3-chloro-phenyl)-propane-1,2-diamine, was extracted with dichloromethane, dried over sodium sulfate, filtered and concentrated (4.2 g). The material was used crude in the next reaction step. MS (ESI): 185.1 (MH+).

Step C] 4-[2-Amino-2-(3-chloro-phenyl)-propylamino]-adamantane-1-carboxylic acid methyl ester To a solution of 2-(3-chloro-phenyl)-propane-1,2-diamine (3.4 g) and 4-oxo-adamantane-1-carboxylic acid methyl ester (CAS 56674-88-5, 3.85 g) in ethanol (50 mL) was added acetic acid (0.7 mL) and reaction mixture was refluxed for 4 h, after which it was cooled to 0° C. and NaBH4 was added. The reaction mixture was then slowly brought to room temperature and left at stirring for 17 h. The reaction was monitored by TLC. After completion, water (30 mL) was slowly added. The reaction mixture was concentrated at reduced pressure to remove the ethanol. The aqueous layer was extracted with DCM (3×50 mL) and the organic layers were then dried over Na2SO4 and then concentrated to get crude desired 4-[2-amino-2-(3-chloro-phenyl)-propylamino]-adamantane-1-carboxylic acid methyl ester (6 g) as a mixture of E/Z isomers. The compound was used in the next step without further purification. MS (ESI): 377.4 (MH+).

Step D]

Example 176

(E/Z)-4-[4-(3-Chloro-phenyl)-4-methyl-2-oxo-imidazlidin-1-yl]-adamantane-1-carboxylic acid methyl ester A solution of 4-[2-amino-2-(3-chloro-phenyl)-propylamino]-adamantane-1-carboxylic acid methyl ester (7.9 g) in 40 mL DCM was cooled to −20° C. and triphosgene (3.1 g) (separately dissolved in 10 mL DCM) was added to it drop wise followed by drop wise addition of triethylamine (6.57 mL). The reaction mixture was slowly brought to RT and left at stirring for 4 h. Reaction was monitored by TLC. After completion, the reaction mixture was quenched with water and the DCM layer was separated. The aqueous layer was again extracted with DCM (2×). The combined DCM layers were dried over Na2SO4 and concentrated to afford the crude product, which was purified by column chromatography to give the desired 4-[4-(3-chloro-phenyl)-4-methyl-2-oxo-imidazolidin-1-yl] adamantane-1-carboxylic acid methyl ester (5.0 g) as a mixture of E/Z isomers as a white solid. MS (ES+): 403.4 (MH+).

Example 177

(E)-4-[4-(3-Chloro-phenyl)-4-methyl-2-oxo-imidazolidin-1-yl]-adamantane-1-carboxylic acid amide Step A] 4-[4-(3-Chloro-phenyl)-4-methyl-2-oxo-imidazolidin-1-yl]-adamantane-1-carboxylic acid To a solution of (E/Z)-4-[4-(3-chloro-phenyl)-4-methyl-2-oxo-imidazolidin-1-yl]adamantane-1-carboxylic acid methyl ester (example 176, 1.8 g) in THF:Methanol:Water (9 mL:6 mL:6 mL), was added LiOH.H2O (0.562 g) at room temp and the reaction was stirred for 17 h. The reaction was monitored by TLC. After completion, the reaction mixture was concentrated to remove organic solvents. Water was added to the reaction mixture and extracted with ethyl acetate to remove impurities. The aqueous layer was acidified with 1N HCl to pH=1 and the product was extracted into DCM (3×50 mL). The organic layers were then dried over Na2SO4 and concentrated to get pure (E/Z)-4-[4-(3-chloro-phenyl)-4-methyl-2-oxo-imidazolidin-1-yl]-adamantane-1-carboxylic acid (1.5 g) which was taken into the next reaction without further purification. MS (ES+): 387.4 (MH+).

Step B] Example 177: (E)-4-[4-(3-Chloro-phenyl)-4-methyl-2-oxo-imidazolidin-1-yl]-adamantane-1-carboxylic acid amide A solution of compound 4-[4-(3-chloro-phenyl)-4-methyl-2-oxo-imidazolidin-1-yl]-adamantane-1-carboxylic acid (130 mg) in DCM (5 mL) was cooled to 0° C. and oxalyl chloride (1 mL) was added to it dropwise followed by addition of 2 or 3 drops of DMF. Reaction was left at room temperature for 5 h. After formation of acid chloride, the excess oxalyl chloride and DCM were evaporated. The residue, dissolved in 5 mL of THF, was cooled to −78 degrees C. and a saturated solution of NH3/THF (10 mL) was added. The reaction was slowly brought to room temperature and then left stirring for 17 h. After completion, the reaction mixture was concentrated and directly loaded onto a silica column and the E isomer was separated from the corresponding (Z)-isomer to give the desired (E)-4-[4-(3-chloro-phenyl)-4-methyl- 2-oxo-imidazolidin-1-yl]-adamantane-1-carboxylic acid amide (55 mg) as a white solid MS (ESI): 388.2 (MH$^+$).

Example 177a,b (E)-4-[(R)-4-(3-Chloro-phenyl)-4-methyl-2-oxo-imidazolidin-1-yl]-adamantane-1-carboxylic acid amide and (E)-4-[(S)-4-(3-Chloro-phenyl)-4-methyl-2-oxo-imidazolidin-1-yl]-adamantane-1-carboxylic acid amide Submission of compound of example 177 to preparative HPLC, using a chiral column Chiralpak AD, with 25% ethanol/heptane as eluant gave the two enantiomers, in optically pure form as white solids.

Example 178

4-(4-Fluoro-phenyl)-1-((E)-5-hydroxy-adamantan-2-yl)-4-methyl-imidazolidin-2-one This material was obtained in analogy to example 176 (step A-D) using 1-(4-fluoro-phenyl)-ethanone (step A) and 5-hydroxy-adamantan-2-one (step C), to give after chromatographic separation after step D the (E) isomer 4-(4-fluoro-phenyl)-1-((E)-5-hydroxy-adamantan-2-yl)-4-methyl-imidazolidin-2-one, as a white solid (40 mg). MS (ES+): 345.2 (MH$^+$).

Example 179

4-(2-Fluoro-phenyl)-1-((E/Z)-5-hydroxy-adamantan-2-yl)-4-methyl-imidazolidin-2-one This material was obtained in analogy to example 176 (step A-D) using 1-(2-fluoro-phenyl)-ethanone (step A) and 5-hydroxy-adamantan-2-one (step C), to give after chromatography after step D a mixture of both E and Z isomers 4-(2-fluoro-phenyl)-1-((E/Z)-5-hydroxy-adamantan-2-yl)-4-methyl-imidazolidin-2-one, as a white solid (35 mg). MS (ES+): 345.2 (MH$^+$).

Example 180

4-(3-Chloro-phenyl)-1-((E)-5-hydroxy-adamantan-2-yl)-4-methyl-imidazolidin-2-one This material was obtained in analogy to example 176 (step A-D) using 5-hydroxy-adamantan-2-one (step C), to give after chromatographic separation after step D the E isomer 4-(3-chloro-phenyl)-1-((E)-5-hydroxy-adamantan-2-yl)-4-methyl-imidazolidin-2-one, as a white solid (33 mg). MS (ES+): 361.19 (MH$^+$).

Example 181

(E/Z)-4-[4-(2-Fluoro-phenyl)-4-methyl-2-oxo-imidazolidin-1-yl]-adamantane-1-carboxylic acid methyl ester This material was obtained in analogy to example 176 (step A-D) using 1-(2-fluoro-phenyl)-ethanone (step A) as a white solid (27 mg). MS (ES+): 387.2 (MH$^+$).

Example 182

4-(2-Chloro-phenyl)-1-((E)-5-hydroxy-adamantan-2-yl)-4-methyl-imidazolidin-2-one This material was obtained in analogy to example 176 (step A-D) using 1-(2-chloro-phenyl)-ethanone (step A) and 5-hydroxy-adamantan-2-one (step C), to give after chromatographic separation after step D the (E) isomer 4-(2-chloro-phenyl)-1-((E)-5-hydroxy-adamantan-2-yl)-4-methyl-imidazolidin-2-one, as a white solid (35 mg). MS (ES+): 361.2 (MH$^+$).

Example 183

1-[(E)-5-Hydroxyadamantan-2-yl]-3',4'-dihydro-2H,2'H-spiro[imidazolidine-4,1'-naphthalen]-2-one This material was obtained in analogy to example 176 (step A-D) using 3,4-dihydro-2H-naphthalen-1-one (step A) and 5-hydroxy-adamantan-2-one (step C), to give after chromatographic separation after step D the (E) isomer 1-[(E)-5-hydroxyadamantan-2-yl]-3',4'-dihydro-2H,2'H-spiro[imidazolidine-4,1'-naphthalen]-2-one, as a white solid (30 mg). MS (ES+): 353.1 (MH$^+$).

Example 184

1-((E)-5-Hydroxy-adamantan-2-yl)-4-methyl-4-naphthalen-2-yl-imidazolidin-2-one

This material was obtained in analogy to example 176 (step A-D) using 1-naphthalen-2-yl-ethanone (step A) and 5-hydroxy-adamantan-2-one (step C), to give after chromatographic separation after step D the (E) isomer 1-((E)-5-hydroxy-adamantan-2-yl)-4-methyl-4-naphthalen-2-yl-imidazolidin-2-one, as a white solid (30 mg). MS (ES+): 377.2 (MH$^+$).

Example 185

(E/Z)-4-[4-(4-Fluoro-phenyl)-4-methyl-2-oxo-imidazolidin-1-yl]-adamantane-1-carboxylic acid methyl ester This material was obtained in analogy to example 176 (step A-D) using 1-(4-fluoro-phenyl)-ethanone (step A), as a white solid (10 mg). MS (ES+): 387.2 (MH$^+$).

Example 186

(E/Z)-4-[4-(4-Chloro-phenyl)-4-methyl-2-oxo-imidazolidin-1-yl]-adamantane-1-carboxylic acid methyl ester This material was obtained in analogy to example 176 (step A-D) using 1-(4-chloro-phenyl)-ethanone (step A), as a white solid (18 mg). MS (ES+): 403.2 (MH$^+$).

Example 187

(E/Z)-4-(4-Methyl-4-naphthalen-2-yl-2-oxo-imidazolidin-1-yl)-adamantane-1-carboxylic acid methyl ester This material was obtained in analogy to example 176 (step A-D) using 1-naphthalen-2-yl-ethanone (step A), as a white solid (35 mg). MS (ES+): 419.1 (MH$^+$).

Example 188

Methyl (E/Z)-4-(2-oxo-3',4'-dihydro-1H,2'H-spiro[imidazolidine-4,1'-naphthalen]-1-yl)adamantane-1-carboxylate This material was obtained in analogy to example 176 (step A-D) using 3,4-dihydro-2H-naphthalen-1-one (step A), as a white solid (35 mg). MS (ES+): 394.3 (MH$^+$).

Example 189

(E/Z)-4-[4-(2-Chloro-phenyl)-4-methyl-2-oxo-imidazolidin-1-yl]-adamantane-1-carboxylic acid methyl ester This material was obtained in analogy to example 176 (step A-D) using 1-(2-chloro-phenyl)-ethanone (step A), as a white solid (25 mg). MS (ES+): 403.2 (MH$^+$).

Example 190

(E)-4-(2-oxo-3',4'-dihydro-1H,2'H-spiro[imidazolidine-4,1'-naphthalen]-1-yl)adamantane-1-carboxamide This material was obtained in analogy to example 177 (step A and B) using methyl (E/Z)-4-(2-oxo-3',4'-dihydro-1H,2'H-spiro[imidazolidine-4,1'-naphthalen]-1-yl)adamantane-1-carboxylate (example 188), to give after chromatographic separation after step B the (E) isomer (E)-4-(2-oxo-3',4'-dihydro-1H,2'H-spiro[imidazolidine-4,1'-naphthalen]-1-yl)adamantane-1-carboxamide, as a white solid (23 mg). MS (ES+): 380.2 (MH$^+$).

Example 191

(E)-4-[4-(2-Fluoro-phenyl)-4-methyl-2-oxo-imidazolidin-1-yl]-adamantane-1-carboxylic acid amide This material was obtained in analogy to example 177 (step A-B) using (E/Z)-4-[4-(2-fluoro-phenyl)-4-methyl-2-oxo-imidazolidin-1-yl]-adamantane-1-carboxylic acid methyl ester (example 181), to give after chromatographic separation after step B the (E) isomer (E)-4-[4-(2-fluoro-phenyl)-4-methyl-2-oxo-imidazolidin-1-yl]-adamantane-1-carboxylic acid amide, as a white solid (25 mg). MS (ES+): 372.3 (MH$^+$).

Example 192

4-(3-Chloro-phenyl)-1-((Z)-5-hydroxy-adamantan-2-yl)-4-methyl-imidazolidin-2-one This material was obtained in analogy to example 176 (step A-D) using 1-(3-chloro-phenyl)-ethanone (step A) and 5-hydroxy-adamantan-2-one (step C), to give after chromatographic separation after step D the (Z) isomer 4-(3-chloro-phenyl)-1-((Z)-5-hydroxy-adamantan-2-yl)-4-methyl-imidazolidin-2-one, as a white solid (17 mg). MS (ES+): 361.2 (MH$^+$).

Example 193

4-(4-Chloro-phenyl)-1-((E)-5-hydroxy-adamantan-2-yl)-4-methyl-imidazolidin-2-one This material was obtained in analogy to example 176 (step A-D) using 1-(4-chloro-phenyl)-ethanone (step A) and 5-hydroxy-adamantan-2-one (step C), to give after chromatographic separation after step D the (E) isomer, 4-(4-chlorophenyl)-1-((E)-5-hydroxy-adamantan-2-yl)-4-methyl-imidazolidin-2-one, as a white solid (17 mg). MS (ESI): 361.2 (MH$^+$).

Example 194 and 195

(+) (S)-4-(4-Chloro-phenyl)-1-((E)-5-hydroxy-adamantan-2-yl)-4-methyl-imidazolidin-2-one and (−) (R)-4-(4-Chloro-phenyl)-1-((E)-5-hydroxy-adamantan-2-yl)-4-methyl-imidazolidin-2-one Racemic 4-(4-chloro-phenyl)-1-((E)-5-hydroxy-adamantan-2-yl)-4-methyl-imidazolidin-2-one (example 193) was subjected to preparative chiral HPLC (Column: Chiralpack AD; Eluent: 15% Isopropanol/heptane; Flow: 35 mL/min; Detection: UV 220 nm) to give (S)-4-(4-chloro-phenyl)-1-((E)-5-hydroxy-adamantan-2-yl)-4-methyl-imidazolidin-2-one ((+) enantiomer, 101 mg, $t_{Ret}$=28 min, MS (ESI): 361.2 (MH$^+$).) and (R)-4-(4-chloro-phenyl)-1-((E)-5-hydroxy-adamantan-2-yl)-4-methyl-imidazolidin-2-one ((−) enantiomer, 103 mg, $t_{Ret}$=170 min, MS (ESI): 361.2 (MH$^+$). Absolute configurations are tentatively assigned.

Example 196

(E/Z)-4-[4-(3,4-Difluoro-phenyl)-4-methyl-2-oxo-imidazolidin-1-yl]-adamantane-1-carboxylic acid methyl ester This material was obtained in analogy to example 176 (step A-D) using 1-(3,4-difluoro-phenyl)-ethanone (step A), as a white solid (70 mg). MS (ESI): 405.2 (MH$^+$).

Example 197 and 198

1-((Z)-5-Hydroxy-adamantan-2-yl)-4-methyl-4-phenyl-imidazolidin-2-one and 1-((E)-5-Hydroxy-adamantan-2-yl)-4-methyl-4-phenyl-imidazolidin-2-one Examples 197 and 198 were obtained in analogy to example 176 (step A-D) using 1-phenyl-ethanone (step A) and 5-hydroxy-adamantan-2-one (step C), to give after chromatographic separation after step D 1-((Z)-5-hydroxy-adamantan-2-yl)-4-methyl-4-phenyl-imidazolidin-2-one (36 mg of a white solid, MS (ESI): 327.3 (MH$^+$)) and 1-((E)-5-hydroxy-adamantan-2-yl)-4-methyl-4-phenyl-imidazolidin-2-one (54 mg of a white solid MS (ESI): 327.3 (MH$^+$)).

Example 199

4-Ethyl-1-((E)-5-hydroxy-adamantan-2-yl)-4-phenyl-imidazolidin-2-one

This material was obtained in analogy to example 176 (step A-D) using 1-phenyl-propan-1-one (step A) and 5-hydroxy-adamantan-2-one (step C), to give after chromatographic separation after step D the (E) isomer, 4-ethyl-1-((E)-5-hydroxy-adamantan-2-yl)-4-phenyl-imidazolidin-2-one, as a white gum (109 mg). MS (ESI): 341.4 (MH$^+$).

Example 200 and 201

1-((Z)-5-Hydroxy-adamantan-2-yl)-4-methyl-4-phenethyl-imidazolidin-2-one and 1-((E)-5-Hydroxy-adamantan-2-yl)-4-methyl-4-phenethyl-imidazolidin-2-one Examples 200 and 201 were obtained in analogy to example 176 (step A-D) using 4-phenyl-butan-2-one (step A) and 5-hydroxy-adamantan-2-one (step C), to give after chromatographic separation of the (E) and (Z) isomers 1-((Z)-5-hydroxy-adamantan-2-yl)-4-methyl-4-phenethyl-imidazolidin-2-one (176 mg as a white solid, MS (ESI): 355.4 (MH$^+$)) and 1-((E)-5-hydroxy-adamantan-2-yl)-4-methyl-4-phenethyl-imidazolidin-2-one (247 mg as a white solid MS (ESI): 355.4 (MH$^+$)).

Example 202 and 203

1-((Z)-5-Hydroxy-adamantan-2-yl)-4-(2-methoxy-phenyl)-4-methyl-imidazolidin-2-one and 1-((E)-5-Hydroxy-adamantan-2-yl)-4-(2-methoxy-phenyl)-4-methyl-imidazolidin-2-one Examples 202 and 203 was obtained in analogy to example 176 (step A-D) using 1-(2-methoxy-phenyl)-ethanone (step A) and 5-hydroxy-adamantan-2-one (step C), to give after chromatographic separation of the (E) and (Z) isomers 1-((Z)-5-hydroxy-adamantan-2-yl)-4-(2-methoxy-phenyl)-4-methyl-imidazolidin-2-one (305 mg as a white gum, MS (ESI): 357.3 (MH$^+$)) and 1-((E)-5-hydroxy-adamantan-2-yl)-4-(2-methoxy-phenyl)-4-methyl-imidazolidin-2-one (552 mg as a white gum MS (ESI): 357.3 (MH$^+$)).

Example 204 and 205

1-((Z)-5-hydroxy-adamantan-2-yl)-4-methoxymethyl-4-phenyl-imidazolidin-2-one and 1-((E)-5-hydroxy-adamantan-2-yl)-4-methoxymethyl-4-phenyl-imidazolidin-2-one Examples 204 and 205 were obtained in analogy to example 1 (step A-D) using 2-methoxy-1-phenyl-ethanone (step A) and 5-hydroxy-adamantan-2-one (step C), to give after chromatographic separation of the (E) and (Z) isomers, 1-((Z)-5-hydroxy-adamantan-2-yl)-4-methoxymethyl-4-phenyl-imidazolidin-2-one (258 mg as a yellow foam, MS (ESI): 357.2 (MH$^+$)) and 1-((E)-5-hydroxy-adamantan-2-yl)-4-methoxymethyl-4-phenyl-imidazolidin-2-one (467 mg as a yellow foam MS (ESI): 357.2 (MH$^+$)).

Example 206 and 207

4-(3,4-Difluoro-phenyl)-1-((Z)-5-hydroxy-adamantan-2-yl)-4-methyl-imidazolidin-2-one and 4-(3,4-difluoro-phenyl)-1-((E)-5-hydroxy-adamantan-2-yl)-4-methyl-imidazolidin-2-one Examples 206 and 207 were obtained in analogy to example 176 (step A-D) using 1-(3,4-difluoro-phenyl)-ethanone (step A) and 5-hydroxy-adamantan-2-one (step C), to give after chromatographic separation of the (E) and (Z) isomers, 4-(3,4-difluoro-phenyl)-1-((Z)-5-hydroxy-adamantan-2-yl)-4-methyl-imidazolidin-2-one (27 mg as a white solid, MS (ESI): 363.3 (MH$^+$)) and 4-(3,4-difluoro-phenyl)-1-((E)-5-hydroxy-adamantan-2-yl)-4-methyl-imidazolidin-2-one (50 mg as a yellow foam MS (ESI): 363.3 (MH$^+$)).

Example 208

(E)-4-(4-Methyl-4-naphthalen-2-yl-2-oxo-imidazolidin-1-yl)-adamantane-1-carboxylic acid amide This material was obtained in analogy to example 177 (step A and B) using (E/Z)-4-(4-methyl-4-naphthalen-2-yl-2-oxo-imidazolidin-1-yl)-adamantane-1-carboxylic acid methyl ester (example 187), as a white solid (35 mg). MS (ESI): 404.4 (MH$^+$).

Example 209

(E)-4-[4-(2-Chloro-phenyl)-4-methyl-2-oxo-imidazolidin-1-yl]-adamantane-1-carboxylic acid amide This material was obtained in analogy to example 177 (step A and B) using (E/Z)-4-[4-(2-chloro-phenyl)-4-methyl-2-oxo-imidazolidin-1-yl]-adamantane-1-carboxylic acid methyl ester (example 189), as a white solid (25 mg). MS (ESI): 388.4 (MH$^+$).

Example 210

(E)-4-[4-(4-Chloro-phenyl)-4-methyl-2-oxo-imidazolidin-1-yl]-adamantane-1-carboxylic acid amide This material was obtained in analogy to example 177 (step A and B) using (E/Z)-4-[4-(4-chloro-phenyl)-4-methyl-2-oxo-imidazolidin-1-yl]-adamantane-1-carboxylic acid methyl ester (example 186), as a white solid (28 mg). MS (ESI): 388.4 (MH$^+$).

Example 211

(E)-4-[4-(3,4-Difluoro-phenyl)-4-methyl-2-oxo-imidazolidin-1-yl]-adamantane-1-carboxylic acid amide This material was obtained in analogy to example 177 (step A and B) using (E/Z)-4-[4-(3,4-difluoro-phenyl)-4-methyl-2-oxo-imidazolidin-1-yl]-adamantane-1-carboxylic acid methyl ester (example 196), as a white solid (27 mg). MS (ESI): 390.3 (MH$^+$).

Example 211a,b (E)-4-[(R)-4-(3,4-Difluoro-phenyl)-4-methyl-2-oxo-imidazolidin-1-yl]-adamantane-1-carboxylic acid amide and (E)-4-[(S)-4-(3,4-Difluoro-phenyl)-4-methyl-2-oxo-imidazolidin-1-yl]-adamantane-1-carboxylic acid amide Submission of compound of example 211 to preparative HPLC, using a chiral column Chiralpak AD, with 25% ethanol/heptane as eluant gave the two enantiomers, in optically pure form as white solids.

Example 212 and 213

4-(3-Fluoro-phenyl)-1-((Z)-5-hydroxy-adamantan-2-yl)-4-methyl-imidazolidin-2-one and 4-(3-Fluoro-phenyl)-1-((E)-5-hydroxy-adamantan-2-yl)-4-methyl-imidazolidin-2-one Examples 212 and 213 were obtained in analogy to example 176 (step A-D) using 1-(3-fluoro-phenyl)-ethanone (step A) and 5-hydroxy-adamantan-2-one (step C), to give after chromatographic separation after step D the (Z) and (E) isomers, 4-(3-Fluoro-phenyl)-1-((Z)-5-hydroxy-adamantan-2-yl)-4-methyl-imidazolidin-2-one (8 mg as a white solid, MS (ES+): 345.3 (MH$^+$)) and 4-(3-Fluoro-phenyl)-1-((E)-5-hydroxy-adamantan-2-yl)-4-methyl-imidazolidin-2-one (45 mg as a white solid MS (ES+): 345.3 (MH$^+$)).

Example 214 and 215

4-(3-Bromo-phenyl)-1-((Z)-5-hydroxy-adamantan-2-yl)-4-methyl-imidazolidin-2-one and (4-(3-bromo-phenyl)-1-((E)-5-hydroxy-adamantan-2-yl)-4-methyl-imidazolidin-2-one Examples 214 and 215 were obtained in analogy to example 176 (step A-D) using 1-(3-bromo-phenyl)-ethanone (step A) and 5-hydroxy-adamantan-2-one (step C), to give after chromatographic separation after step D the (Z) and (E) isomers, 4-(3-bromo-phenyl)-1-((Z)-5-hydroxy-adamantan-2-yl)-4-methyl-imidazolidin-2-one (25 mg as a white solid, MS (ESI): 405.3 (MH$^+$)) and (4-(3-bromo-phenyl)-1-((E)-5-hydroxy-adamantan-2-yl)-4-methyl-imidazolidin-2-one (25 mg as a white solid MS (ESI): 405.3 (MH$^+$)).

Example 216 and 217

4-(2,4-Difluoro-phenyl)-1-((Z)-5-hydroxy-adamantan-2-yl)-4-methyl-imidazolidin-2-one and 4-(2,4-difluoro-phenyl)-1-((E)-5-hydroxy-adamantan-2-yl)-4-methyl-imidazolidin-2-one Examples 216 and 217 were obtained in analogy to example 176 (step A-D) using 1-(2,4-difluoro-phenyl)-ethanone (step A) and 5-hydroxy-adamantan-2-one (step C), to give after chromatographic separation after step D the (Z) and (E) isomers, 4-(2,4-difluoro-phenyl)-1-((Z)-5-hydroxy-adamantan-2-yl)-4-methyl-imidazolidin-2-one (50 mg as a white solid, MS (ESI): 363.3 (MH$^+$)) and 4-(2,4-difluoro-phenyl)-1-((E)-5-hydroxy-adamantan-2-yl)-4-methyl-imidazolidin-2-one (55 mg as a white solid MS (ESI): 363.3 (MH$^+$)).

Example 218

(E)-4-[4-(3-Fluoro-phenyl)-4-methyl-2-oxo-imidazolidin-1-yl]-adamantane-1-carboxylic acid amide This material was obtained in analogy to example 177 (step A and B) using (E/Z)-4-[4-(3-fluoro-phenyl)-4-methyl-2-oxo-imidazolidin-1-yl]-adamantane-1-carboxylic acid methyl ester (example 230), as a white solid (40 mg). MS (ESI): 372.2 (MH$^+$).

Example 218a,b (E)-4-[(R)-4-(3-Fluoro-phenyl)-4-methyl-2-oxo-imidazolidin-1-yl]-adamantane-1-carboxylic acid amide and (E)-4-[(S)-4-(3-Fluoro-phenyl)-4-methyl-2-oxo-imidazolidin-1-yl]-adamantane-1-carboxylic acid amide Submission of compound of example 218 to preparative HPLC, using a chiral column Chiralpak AD, with 25% ethanol/heptane as eluant gave the two enantiomers, in optically pure form as white solids.

Example 219

4-(3-Chloro-4-fluoro-phenyl)-1-((E)-5-hydroxy-adamantan-2-yl)-4-methyl-imidazolidin-2-one This material was obtained in analogy to example 176 (step A-D) using 1-(3-chloro-4-fluoro-phenyl)-ethanone (step A) and 5-hydroxy-adamantan-2-one (step C), to give after chromatographic separation after step D the (E) isomer, 4-(3-chloro-4-fluoro-phenyl)-1-((E)-5-hydroxy-adamantan-2-yl)-4-methyl-imidazolidin-2-one as a white solid (60 mg). MS (ES+): 379.2 (MH$^+$).

Example 220

1-((E)-5-Hydroxy-adamantan-2-yl)-4-(3-methoxy-phenyl)-4-methyl-imidazolidin-2-one This material was obtained in analogy to example 176 (step A-D) using 1-(3-methoxy-phenyl)-ethanone (step A) and 5-hydroxy-adamantan-2-one (step C), to give after chromatographic separation after step D the (E) isomer, 1-((E)-5-hydroxy-adamantan-2-yl)-4-(3-methoxy-phenyl)-4-methyl-imidazolidin-2-one as a white solid (50 mg). MS (ES+): 357.2 (MH$^+$).

Example 221

1-((E)-5-Hydroxy-adamantan-2-yl)-4-(4-methoxy-phenyl)-4-methyl-imidazolidin-2-one This material was obtained in analogy to example 176 (step A-D) using 1-(4-methoxy-phenyl)-ethanone (step A) and 5-hydroxy-adamantan-2-one (step C), to give after chromatographic separation after step D the (E) isomer, 1-((E)-5-hydroxy-adamantan-2-yl)-4-(4-methoxy-phenyl)-4-methyl-imidazolidin-2-one as a white solid (30 mg). MS (ES+): 357.2 (MH$^+$).

Example 222 and 223

1-((Z)-5-Hydroxy-adamantan-2-yl)-4-methyl-4-(4-trifluoromethoxy-phenyl)-imidazolidin-2-one and 1-((E)-5-hydroxy-adamantan-2-yl)-4-methyl-4-(4-trifluoromethoxy-phenyl)-imidazolidin-2-one Examples 222 and 223 were obtained in analogy to example 176 (step A-D) using 1-(4-trifluoromethoxy-phenyl)-ethanone (step A) and 5-hydroxy-adamantan-2-one (step C), to give after chromatographic separation after step D the (Z) and (E) isomers 1-((Z)-5-hydroxy-adamantan-2-yl)-4-methyl-4-(4-trifluoromethoxy-phenyl)-imidazolidin-2-one (50 mg as a white solid, MS (ESI): 411.2 (MH$^+$)) and 1-((E)-5-hydroxy-adamantan-2-yl)-4-methyl-4-(4-trifluoromethoxy-phenyl)-imidazolidin-2-one (52 mg as a white solid MS (ESI): 411.3 (MH$^+$)).

Example 224 and 225

1-((Z)-5-Hydroxy-adamantan-2-yl)-4-methyl-4-(3-trifluoromethyl-phenyl)-imidazolidin-2-one and 1-((E)-5-hydroxy-adamantan-2-yl)-4-methyl-4-(3-trifluoromethyl-phenyl)-imidazolidin-2-one Examples 224 and 225 were obtained in analogy to example 176 (step A-D) using 1-(3-trifluoromethyl-phenyl)-ethanone (step A) and 5-hydroxy-adamantan-2-one (step C), to give after chromatographic separation after step D the (Z) and (E) isomers 1-((Z)-5-hydroxy-adamantan-2-yl)-4-methyl-4-(3-trifluoromethyl-phenyl)-imidazolidin-2-one (539 mg as a yellow gum, MS (ESI): 395.2 (MH$^+$)) and 1-((E)-5-hydroxy-adamantan-2-yl)-4-methyl-4-(3-trifluoromethyl-phenyl)-imidazolidin-2-one (520 mg as a yellow gum MS (ESI): 395.2 (MH$^+$)).

Example 226 and 227

4-(4-Chloro-3-trifluoromethyl-phenyl)-1-((Z)-5-hydroxy-adamantan-2-yl)-4-methyl-imidazolidin-2-one and 4-(4-chloro-3-trifluoromethyl-phenyl)-1-((E)-5-hydroxy-adamantan-2-yl)-4-methyl-imidazolidin-2-one Examples 226 and 227 were obtained in analogy to example 176 (step A-D) using 1-(4-chloro-3-trifluoromethyl-phenyl)-ethanone (step A) and 5-hydroxy-adamantan-2-one (step C), to give after chromatographic separation after step D the (Z) and (E) isomers 4-(4-chloro-3-trifluoromethyl-phenyl)-1-((Z)-5-hydroxy-adamantan-2-yl)-4-methyl-imidazolidin-2-one (336 mg as a yellow gum, MS (ESI): 429.2 (MH$^+$)) and 4-(4-chloro-3-trifluoromethyl-phenyl)-1-((E)-5-hydroxy-adamantan-2-yl)-4-methyl-imidazolidin-2-one (391 mg as a yellow gum MS (ESI): 429.2 (MH$^+$)).

Example 228

(E/Z)-4-[4-(2,4-Difluoro-phenyl)-4-methyl-2-oxo-imidazolidin-1-yl]-adamantane-1-carboxylic acid methyl ester This material was obtained in analogy to example 176 (step A-D) using 1-(2,4-difluoro-phenyl)-ethanone (step A), as a white solid (40 mg). MS (ESI): 405.3 (MH$^+$).

Example 229

(E)-4-[4-(2,4-Difluoro-phenyl)-4-methyl-2-oxo-imidazolidin-1-yl]-adamantane-1-carboxylic acid amide This material was obtained in analogy to example 177 (step A and B) using (E/Z)-4-[4-(2,4-difluoro-phenyl)-4-methyl-2-oxo-imidazolidin-1-yl]-adamantane-1-carboxylic acid methyl ester (example 228), as a white solid (50 mg). MS (ESI): 390.2 (MH$^+$).

Example 230

(E/Z)-4-[4-(3-Fluoro-phenyl)-4-methyl-2-oxo-imidazolidin-1-yl]-adamantane-1-carboxylic acid methyl ester This material was obtained in analogy to example 176 (step A-D) using 1-(3-fluoro-phenyl)-ethanone (step A), as a white solid (32 mg). MS (ES+): 387.3 (MH$^+$).

Example 231

1-((E)-5-Hydroxy-adamantan-2-yl)-4-methyl-4-m-tolyl-imidazolidin-2-one

This material was obtained in analogy to example 176 (step A-D) using 1-m-tolyl-ethanone (step A) and 5-hydroxy-adamantan-2-one (step C), to give after chromatographic separation after step D the (E) isomer 1-((E)-5-hydroxy-adamantan-2-yl)-4-methyl-4-m-tolyl-imidazolidin-2-one as a white solid (27 mg). MS (ES+): 341.3 (MH$^+$).

Example 232

1-((Z)-5-Hydroxy-adamantan-2-yl)-4-methyl-4-naphthalen-2-yl-imidazolidin-2-one

This material was obtained in analogy to example 176 (step A-D) using 1-naphthalen-2-yl-ethanone (step A) and 5-hydroxy-adamantan-2-one (step C), to give after chromatographic separation after step D the (Z) isomer 1-((Z)-5-hydroxy-adamantan-2-yl)-4-methyl-4-naphthalen-2-yl-imidazolidin-2-one as a white solid (25 mg). MS (ES+): 377.4 (MH$^+$).

Example 233

(E/Z)-4-[4-(3-Bromo-phenyl)-4-methyl-2-oxo-imidazolidin-1-yl]-adamantane-1-carboxylic acid methyl ester This material was obtained in analogy to example 176 (step A-D) using 1-(3-bromo-phenyl)-ethanone (step A), as a white solid (25 mg). MS (ES+): 447.3 (MH$^+$).

Example 234

(Z)-4-(4-Methyl-4-naphthalen-2-yl-2-oxo-imidazolidin-1-yl)-adamantane-1-carboxylic acid amide This material was obtained according to the procedure for example 208 and in analogy to example 177 (step A and B) using (E/Z)-4-(4-methyl-4-naphthalen-2-yl-2-oxo-imidazolidin-1-yl)-adamantane-1-carboxylic acid methyl ester (example 187). In this case, the Z isomer was obtained by separation from the E isomer using flash column chromatography, as a white solid (40 mg). MS (ESI): 390.2 (MH$^+$).

Example 235

(E/Z)-4-[4-(3,4-Dimethoxy-phenyl)-4-methyl-2-oxo-imidazolidin-1-yl]-adamantane-1-carboxylic acid methyl ester This material was obtained in analogy to example 176 (step A-D) using 1-(3,4-dimethoxy-phenyl)-ethanone (step A), as a white solid (50 mg). MS (ES+): 429.5 (MH$^+$).

Example 236

1-((E/Z)-5-Hydroxy-adamantan-2-yl)-4-methyl-4-pyridin-3-yl-imidazolidin-2-one

This material was obtained in analogy to example 176 (step A-D) using 1-Pyridin-3-yl-ethanone (step A) and 5-hydroxy-adamantan-2-one (step C), as a white solid (30 mg). MS (ES+): 327.2 (MH$^+$).

Example 237

(E/Z)-4-[4-(3-Chloro-4-fluoro-phenyl)-4-methyl-2-oxo-imidazolidin-1-yl]-adamantane-1-carboxylic acid methyl ester This material was obtained in analogy to example 176 (step A-D) using 1-(3-chloro-4-fluoro-phenyl)-ethanone (step A), to give the desired product as a mixture of E/Z isomers.

Example 238

(E)-4-[4-(3-Chloro-4-fluoro-phenyl)-4-methyl-2-oxo-imidazolidin-1-yl]-adamantane-1-carboxylic acid amide This material was obtained in analogy to example 177 (step A and B) using (E/Z)-4-[4-(3-chloro-4-fluoro-phenyl)-4-methyl-2-oxo-imidazolidin-1-yl]-adamantane-1-carboxylic acid methyl ester (example 237), as a white solid.

Example 239

4-(3-Chloro-4-fluoro-phenyl)-1-((E)-5-hydroxy-adamantan-2-yl)-4-methyl-imidazolidin-2-one This material was obtained in analogy to example 176 (step A-D) using 1-(3-chloro-4-fluoro-phenyl)-ethanone (step A) and 5-hydroxy-adamantan-2-one (step C), as a white solid.

Example 240

4-(3,4-Difluoro-phenyl)-1-((E)-5-hydroxymethyl-adamantan-2-yl)-4-methyl-imidazolidin-2-one A solution of (E/Z)-4-[4-(3,4-difluoro-phenyl)-4-methyl-2-oxo-imidazolidin-1-yl]-adamantane-1-carboxylic acid methyl ester (100 mg, example 196) in DCM (10 mL) was cooled to 0° C. and borane-DMS complex (0.56 mL of a 1 M solution) was added and the reaction was allowed to stir overnight at room temperature and then quenched with DCM/water. The mixture was extracted with DCM and washed with saturated sodium bicarbonate, dried over sodium sulphate and concentrated. Column chromatography over silica gel afforded the desired (E) isomer 4-(3,4-Difluoro-phenyl)-1-((E)-5-hydroxymethyl-adamantan-2-yl)-4-methyl-imidazolidin-2-one as a white solid (20 mg). MS (ESI): 377.3 (MH$^+$).

Example 241

4-(2-Chloro-phenyl)-1-((E)-5-hydroxymethyl-adamantan-2-yl)-4-methyl-imidazolidin-2-one This material was obtained in analogy to example 240 using (E/Z)-4-[4-(2-chloro-phenyl)-4-methyl-2-oxo-imidazolidin-1-yl]-adamantane-1-carboxylic acid methyl ester (example 189), as a white solid (30 mg). MS (ES+): 375.2 (MH$^+$).

Example 242

4-(2-Fluoro-phenyl)-1-((E)-5-hydroxymethyl-adamantan-2-yl)-4-methyl-imidazolidin-2-one This material was obtained in analogy to example 240 using (E/Z)-4-[4-(2-fluoro-phenyl)-4-methyl-2-oxo-imidazolidin-1-yl]-adamantane-1-carboxylic acid methyl ester (example 181), as a white solid (12 mg). MS (ES+): 359.3 (MH$^+$).

Example 243 and 244

1-((E)-5-Hydroxy-adamantan-2-yl)-3,4-dimethyl-4-phenyl-imidazolidin-2-one and 1-((Z)-5-hydroxy-adamantan-2-yl)-3,4-dimethyl-4-phenyl-imidazolidin-2-one Step A] 2-Methylamino-2-phenyl-propionitrile To a solution of acetophenone (10 g) in 50 mL methanol, a solution of sodium cyanide (12.23 g) and methylamine.HCl (16.71 g) in 50 mL water was added slowly at room temp. The reaction mixture was heated at 40° C. for 2 h and then at room temperature for 18 h and was monitored by TLC. After completion, the reaction mixture was extracted with 3×100 mL dichloromethane. The organic layer was then dried over Na$_2$SO$_4$ and concentrated to afford the desired 2-methylamino-2-phenyl-propionitrile (12.5 g) which was used in the next step without further purification.

Step B] N$^1$-methyl-1-phenylethane-1,2-diamine (CAS 66308-14-3)

A solution of 2-methylamino-2-phenyl-propionitrile (7.8 g) in toluene (60 mL) was cooled to −78° C. and DIBAL-H solution (104 mL of a 20% solution in toluene) was added drop wise under nitrogen. The reaction mixture was slowly warmed to room temperature and then left at stirring for 17 h. After completion, the reaction mixture was quenched with 30 mL methanol and then 100 mL water. All solvents were evaporated and crude material was taken into 50 mL of water and acidified to pH=1 with 1N HCl. The mixture was extracted with ethyl acetate and separated, and the aqueous layer was basified to pH=14 with 30% NaOH solution. The free diamine was extracted with dichloromethane, dried over sodium sulfate, filtered and concentrated to obtain the desired known N$^1$-methyl-1-phenylethane-1,2-diamine (CAS 66308-14-3) (7.8 g) which was used in the next step without further purification.

Step C] (E)-4-(2-Methylamino-2-phenyl-propylamino)-adamantan-1-ol

To a solution of N$^1$-methyl-1-phenylethane-1,2-diamine (2.0 g) and 5-hydroxy-adamantan-2-one (2.02 g) in 20 mL ethanol, acetic acid (0.5 mL) was added and reaction mixture was refluxed for 4 h, after which it was cooled to 0° C. and NaBH$_4$ (0.91 g) was added. The reaction mixture was then slowly brought to room temperature and left stirring for 17 h. Reaction was monitored by TLC. After completion, water (20 mL) was slowly added and the reaction mixture was concentrated at reduced pressure to remove the ethanol. More water (10 mL) was added and aqueous layer was extracted with DCM (3×30 mL). The organic fractions were then dried over Na$_2$SO$_4$ and concentrated to afford crude desired (E)-4-(2-methylamino-2-phenyl-propylamino)-adamantan-1-ol (3.4 g) which was used without further purification in the next step.

Step D] 1-((E)-5-Hydroxy-adamantan-2-yl)-3,4-dimethyl-4-phenyl-imidazolidin-2-one and 1-((Z)-5-Hydroxy-adamantan-2-yl)-3,4-dimethyl-4-phenyl-imidazolidin-2-one To a solution of (2.6 g) in 15 mL DCM was cooled to −20° C. and triphosgene (0.957 g separately dissolved in 5 mL DCM) was added drop wise followed by a drop wise addition of triethylamine (2.3 mL). The reaction mixture was slowly brought to RT and left stirring for 4 h. The reaction was monitored by TLC. After completion, the reaction mixture was quenched with 2N HCl and the DCM layer was separated and the aqueous layer was extracted with further DCM. The combined DCM layers were washed with cold saturated sodium bicarbonate solution, dried over Na$_2$SO$_4$ and concentrated to afford the crude product, which was purified by column chromatography over silica gel (50% ethyl acetate in hexane) to afford 1-((E)-5-hydroxy-adamantan-2-yl)-3,4-dimethyl-4-phenyl-imidazolidin-2-one (115 mg), MS (ESI):

341.3 (MH⁺) and 1-((Z)-5-hydroxy-adamantan-2-yl)-3,4-dimethyl-4-phenyl-imidazolidin-2-one (210 mg), MS (ESI): 341.3 (MH$^+$).

Example 245

4-(4-Chloro-phenyl)-1-((E/Z)-5-hydroxy-adamantan-2-yl)-3,4-dimethyl-imidazolidin-2-one This material was obtained as a mixture of E and Z isomers in analogy to example 243 & 244 (step A-D) using 1-(4-chloro-phenyl)-ethanone (step A), as a white solid (20 mg). MS (ESI): 375.3 (MH$^+$).

Example 246 and 247

4-(4-Fluoro-phenyl)-1-((Z)-5-hydroxy-adamantan-2-yl)-3,4-dimethyl-imidazolidin-2-one and 4-(4-Fluoro-phenyl)-1-((E)-5-hydroxy-adamantan-2-yl)-3,4-dimethyl-imidazolidin-2-one Examples 246 and 247 were obtained in analogy to example 243 & 244 (step A-D) using 1-(4-fluoro-phenyl)-ethanone (step A), to give after chromatographic separation after step D the (Z) and (E) isomers 4-(4-fluoro-phenyl)-1-((Z)-5-hydroxy-adamantan-2-yl)-3,4-dimethyl-imidazolidin-2-one (25 mg as a white solid, MS (ESI): 358.2 (MH$^+$)) and 4-(4-Fluoro-phenyl)-1-((E)-5-hydroxy-adamantan-2-yl)-3,4-dimethyl-imidazolidin-2-one (105 mg as a white solid MS (ESI): 358.2 (MH$^+$)).

Example 248 and 249:4

(4-Fluoro-phenyl)-1-((Z)-5-hydroxy-adamantan-2-yl)-3,4-dimethyl-imidazolidin-2-one and 4-(2-fluoro-phenyl)-1-((E)-5-hydroxy-adamantan-2-yl)-3,4-dimethyl-imidazolidin-2-one Examples 248 and 249 were obtained in analogy to example 243 & 244 (step A-D) using 1-(2-fluoro-phenyl)-ethanone (step A), to give after chromatographic separation after step D the (Z) and (E) isomers 4-(4-fluoro-phenyl)-1-((Z)-5-hydroxy-adamantan-2-yl)-3,4-dimethyl-imidazolidin-2-one (55 mg as a white solid, MS (ESI): 359.2 (MH$^+$)) and 4-(2-fluoro-phenyl)-1-((E)-5-hydroxy-adamantan-2-yl)-3,4-dimethyl-imidazolidin-2-one (55 mg as a white solid MS (ESI): 359.2 (MH$^+$)).

Example 250 and 251

3-Benzyl-1-((Z)-5-hydroxy-adamantan-2-yl)-4-methyl-4-phenyl-imidazolidin-2-one and 3-benzyl-1-((E)-5-hydroxy-adamantan-2-yl)-4-methyl-4-phenyl-imidazolidin-2-one Examples 251 and 251 were obtained in analogy to example 243 & 244 (step A-D) using benzylamine (step A), to give after chromatographic separation after step D the (Z) and (E) isomers 3-benzyl-1-((Z)-5-hydroxy-adamantan-2-yl)-4-methyl-4-phenyl-imidazolidin-2-one (37 mg as a white solid, MS (ESI): 417.4 (MH$^+$)) and 3-benzyl-1-((E)-5-hydroxy-adamantan-2-yl)-4-methyl-4-phenyl-imidazolidin-2-one (24 mg as a white solid MS (ESI): 417.4 (MH$^+$)).

Example 252

(E/Z)-4-(3,4-Dimethyl-2-oxo-4-phenyl-imidazolidin-1-yl)-adamantane-1-carboxylic acid methyl ester This material was obtained as a mixture of E and Z isomers in analogy to example 243 & 244 (step A-D) using 1-phenyl-ethanone (step A) and 4-oxo-adamantane-1-carboxylic acid methyl ester (CAS 56674-88-5) (step C), as a white solid (21 mg). MS (ESI): 383.3 (MH$^+$).

Example 253

(E/Z)-4-[4-(4-Chloro-phenyl)-3,4-dimethyl-2-oxo-imidazolidin-1-yl]-adamantane-1-carboxylic acid methyl ester This material was obtained as a mixture of E and Z isomers in analogy to example 243 & 244 (step A-D) using 1-(4-chloro-phenyl)-ethanone (step A) and 4-oxo-adamantane-1-carboxylic acid methyl ester (CAS 56674-88-5) (step C), as a white solid (30 mg). MS (ESI): 417.3 (MH$^+$).

Example 254

(E)-4-(3,4-Dimethyl-2-oxo-4-phenyl-imidazolidin-1-yl)-adamantane-1-carboxylic acid This material was obtained in one step from (E/Z)-4-(3,4-Dimethyl-2-oxo-4-phenyl-imidazolidin-1-yl)-adamantane-1-carboxylic acid methyl ester (example 252) via saponification in analogy to example 176, step A, using LiOH in THF:Methanol:Water (3:2:2) at room temperature over 16 hours. The desired E isomer (E)-4-(3,4-dimethyl-2-oxo-4-phenyl-imidazolidin-1-yl)-adamantane-1-carboxylic acid was isolated via chromatographic separation over silica gel column from the corresponding (Z) isomer as a white solid (10 mg). MS (ESI): 369.3 (MH$^+$).

Example 255

(E)-4-(4-Benzyloxymethyl-3-methyl-2-oxo-imidazolidin-1-yl)-adamantane-1-carboxylic acid amide Step A] 3-Benzyloxy-2-methylamino-propionitrile A solution of known benzyloxy-acetaldehyde (10 g) in 25 mL ether, was added to an aqueous solution of methylamine (5.16 g of a 40% solution in water) at 0° C. followed by addition of NaCN (6.4 g dissolved in 10 mL water). The reaction mixture was stirred overnight at room temperature. The reaction was monitored by TLC and after completion, the ether layer was separated. The aqueous layer was extracted with 2×30 mL ethyl acetate and the combined organic layers were then dried over sodium sulfate, filtered and the volatiles where then concentrated to afford the crude product which was purified by column chromatography using basic alumina to give 3-benzyloxy-2-methylamino-propionitrile (5.0 g) as a dark brown oil.

Step B] 3-(Benzyloxy)-N²-methylpropane-1,2-diamine

A solution of 3-benzyloxy-2-methylamino-propionitrile (5.0 g) in toluene (90 mL) was cooled to −78° C. and DIBAL-H solution (90 mL of a 20% in toluene) was added drop wise under nitrogen atmosphere. Reaction mixture was slowly warmed to room temperature and then left at stirring for 17 h. The reaction was monitored by TLC. After completion, the reaction mixture was quenched with 10 mL methanol and then 50 mL water. The volatiles where evaporated in vacuo and the crude material was taken up in 50 mL water and acidified to pH=1 with 1M HCl. The aqueous phase was extracted with ethyl acetate and the aqueous layer was subsequently basified to pH=14 with 30% NaOH solution. The free diamine was extracted with dichloromethane, dried over sodium sulfate, filtered and concentrated to afford the desired 3-(benzyloxy)-$N^2$-methylpropane-1,2-diamine (3.8 g) as a brown oil, which was used in the next reaction without further purification. MS (ES+): 195.1 (MH$^+$).

Step C] 4-(3-Benzyloxy-2-methylamino-propylamino)-adamantane-1-carboxylic acid methyl ester This material was prepared in analogy to example 176, step C using 3-(benzyloxy)-$N^2$-methylpropane-1,2-diamine (1.2 g), to afford 4-(3-benzyloxy-2-methylamino-propylamino)-adamantane-1-carboxylic acid methyl ester (1.1 g) as a brown viscous oil which was used in the next step without further purification. MS (ES+): 387.30 (MH$^+$).

Step D] (E/Z)-4-(4-Benzyloxymethyl-3-methyl-2-oxo-imidazolidin-1-yl)-adamantane-1-carboxylic acid methyl ester This material was prepared in analogy to example 176, step D, using 4-(3-benzyloxy-2-methylamino-propylamino)-adamantane-1-carboxylic acid methyl ester (1.1 g), to afford (E/Z)-4-(4-benzyloxymethyl-3-methyl-2-oxo-imidazolidin-1-yl)-adamantane-1-carboxylic acid methyl ester (200 mg), as a brown solid after column chromatography. MS (ESI): 413.4 (MH$^+$).

Step E] (E)-4-(4-Benzyloxymethyl-3-methyl-2-oxo-imidazolidin-1-yl)-adamantane-1-carboxylic acid This material was obtained in analogy to example 177, step A, using (E)-4-(4-benzyloxymethyl-3-methyl-2-oxo-imidazolidin-1-yl)-adamantane-1-carboxylic acid methyl ester (85 mg), to afford (E)-4-(4-benzyloxymethyl-3-methyl-2-oxo-imidazolidin-1-yl)-adamantane-1-carboxylic acid (20 mg), as a light brown solid after chromatographic separation of the (E) isomer from the (Z) isomer. MS (ESI): 399.3 (MH$^+$).

Step F] (E)-4-(4-Benzyloxymethyl-3-methyl-2-oxo-imidazolidin-1-yl)-adamantane-1-carboxylic acid amide This material was obtained in analogy to example 177, step B, using (E)-4-(4-benzyloxymethyl-3-methyl-2-oxo-imidazolidin-1-yl)-adamantane-1-carboxylic acid (25 mg), to afford (E)-4-(4-benzyloxymethyl-3-methyl-2-oxo-imidazolidin-1-yl)-adamantane-1-carboxylic acid amide (6 mg) after chromatographic purification, as a white solid. MS (ESI): 398.2 (MH$^+$).

Example 256

1-((E)-5-Hydroxy-adamantan-2-yl)-4-hydroxymethyl-3-methyl-imidazolidin-2-one

Step A] 4-Benzyloxymethyl-1-(5-hydroxy-adamantan-2-yl)-3-methyl-imidazolidin-2-one This material was obtained in analogy to example 255 (step A-D) using 5-hydroxy-adamantan-2-one (step C). The desired (E)-isomer was isolated from the (Z)-isomer by flash column chromatography over silica gel in step D, as a white solid (15 mg). MS (ES+): 371.3 (MH$^+$).

Step B] 1-((E)-5-Hydroxy-adamantan-2-yl)-4-hydroxymethyl-3-methyl-imidazolidin-2-one To a solution of 4-benzyloxymethyl-1-(5-hydroxy-adamantan-2-yl)-3-methyl-imidazolidin-2-one (200 mg) in ethanol was added Pd/C catalyst (30 mg) and the reaction vessel was pressurized with hydrogen gas to 60 psi for 28 h. The reaction was monitored by MS. After completion, the reaction mixture was purged with nitrogen and was filtered over celite and the filtrate was concentrated to dryness. Column chromatography over silica gel afforded the desired 1-((E)-5-hydroxy-adamantan-2-yl)-4-hydroxymethyl-3-methyl-imidazolidin-2-one (142 mg) as a white solid. MS (ES+): 281.25 (MH$^+$).

Example 257

6-[1-((E)-5-Hydroxy-adamantan-2-yl)-3-methyl-2-oxo-imidazolidin-4-ylmethoxy]-nicotinonitrile To a solution of 1-((E)-5-hydroxy-adamantan-2-yl)-4-hydroxymethyl-3-methyl-imidazolidin-2-one (49 mg, example 256) in THF (2 mL) at 0° C. was added NaHMDS (201 µL of a 1M solution in THF) via syringe. After 10 minutes a solution of 6-chloro-nicotinonitrile (24 mg) in THF (0.5 mL) was added dropwise via syringe. After 2 hours at 0° C. the reaction was quenched with aqueous sodium bicarbonate solution and diluted with EtOAc. The phases were separated and the aqueous phase was extracted with more EtOAc. The combined organic phases were washed with 1N HCl solution, dried over sodium sulfate, filtered and the volatiles were reduced in vacuo. Column chromatography over silica gel afforded the desired 6-[1-((E)-5-hydroxy-adamantan-2-yl)-3-methyl-2-oxo-imidazolidin-4-ylmethoxy]-nicotinonitrile (24 mg) as a white solid. MS (ESI): 383.3 (MH$^+$).

Example A

A compound of formula I can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

It is to be understood that the invention is not limited to the particular embodiments of the invention described above, as variations of the particular embodiments may be made and still fall within the scope of the appended claims.

What is claimed is:

1. A compound of formula (III):

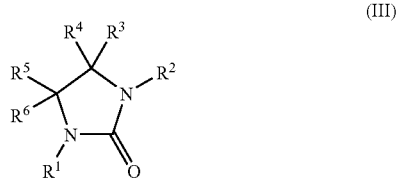

wherein $R^1$ is a) bornyl, norbornyl, adamantyl or adamantyl substituted with one or two substituents independently selected from hydroxy, alkoxy, halogen, alkyl, hydroxyalkyl, amino, aminocarbonyl, alkoxycarbonyl, hydroxycarbonyl, alkylcarbonylamino, alkyl-S(O)$_2$-amino, haloalkyl-S(O)$_2$-amino, alkoxycarbonylamino-S(O)$_2$-amino, amino-S(O)$_2$-amino, hydroxyalkylcarbonylamino, aminocarbonylamino and haloalkoxy;

b) trifluoromethylphenyl, methoxyphenyl, haloalkoxyphenyl or difluorophenyl, wherein trifluoromethylphenyl, haloalkoxyphenyl and difluorophenyl are optionally substituted with one or two substituents independently selected from alkyl, halogen, haloalkyl, alkoxy, hydroxy and haloalkoxy;

c) trifluoromethylphenylalkyl or trifluoromethylphenylalkyl substituted with one or two substituents independently selected from alkyl, halogen, haloalkyl, alkoxy, hydroxy and haloalkoxy;

d) phenylcycloalkyl or phenylcycloalkyl substituted with one to three substituents independently selected from alkyl, halogen, haloalkyl, alkoxy, hydroxy and haloalkoxy;

e) cyanophenyl or cyanophenyl substituted with halogen; or f) dihalophenyl, aminocarbonylphenyl or hydroxyphenyl, wherein aminocarbonylphenyl and hydroxyphenyl are optionally substituted with one or two substituents independently selected from alkyl, halogen, haloalkyl, alkoxy and haloalkoxy;

$R^2$ is hydrogen, alkyl, alkenyl, haloalkyl, pyridinylalkyl, cycloalkyl, cycloalkylalkyl or phenylalkyl or $R^2$ is pyridinylalkyl or phenylalkyl which both are substituted with one to three substituents independently selected from alkyl, hydroxy, alkoxy, halogen, haloalkyl and haloalkoxy;

one of $R^3$ and $R^4$ is cycloalkyl and the other one is a) hydrogen, alkyl, pyridinyl, cycloalkyl, cycloalkylalkyl or haloalkyl;

b) phenyl or phenyl substituted with one to three substituents independently selected from fluoro, chloro, bromo, haloalkyl, alkoxy, hydroxy, haloalkyl and haloalkoxy;

c) phenylalkyl or pyridinylalkyl, wherein phenylalkyl and pyridinylalkyl are optionally substituted with one to three substituents independently selected from alkyl, halogen, haloalkyl and hydroxy;

d) oxetane or oxetane substituted with alkyl;

e) naphthyl or tetrahydronapthyl;

f) phenylalkoxyalkyl or phenylalkoxyalkyl substituted with one to three substituents independently selected from alkyl and halogen;

g) hydroxyalkyl; or h) pyridinyloxyalkyl or pyridinyloxyalkyl substituted with cyano;

one of $R^5$ and $R^6$ is hydrogen, isopropyl, isobutyl, cycloalkyl or haloalkyl and the other one is hydrogen;

and pharmaceutically acceptable salts and esters thereof.

2. The compound according to claim 1, wherein $R^1$ is a) bornyl, norbornyl, adamantyl or adamantyl substituted with one or two substituents independently selected from hydroxy, alkoxy, halogen and alkyl;

b) trifluoromethylphenyl, methoxyphenyl, haloalkoxyphenyl or difluorophenyl, wherein trifluoromethylphenyl, haloalkoxyphenyl and difluorophenyl are optionally substituted with one or two substituents independently selected from alkyl, halogen, haloalkyl, alkoxy, hydroxy and haloalkoxy;

c) trifluoromethylphenylalkyl or trifluoromethylphenylalkyl substituted with one or two substituents independently selected from alkyl, halogen, haloalkyl, alkoxy, hydroxy and haloalkoxy; or d) phenylcycloalkyl or phenylcycloalkyl substituted with one to three substituents independently selected from alkyl, halogen, haloalkyl, alkoxy, hydroxy and haloalkoxy;

$R^2$ is hydrogen, alkyl, haloalkyl, pyridinylalkyl, cycloalkyl, cycloalkylalkyl or phenylalkyl or $R^2$ is pyridinylalkyl or phenylalkyl which both are substituted with one to three substituents independently selected from alkyl, hydroxy, alkoxy, halogen and haloalkyl;

one of $R^3$ and $R^4$ is cycloalkyl and the other one is a) hydrogen, alkyl, pyridinyl, cycloalkyl, cycloalkylalkyl or haloalkyl;

b) phenyl or phenyl substituted with one to three substituents independently selected from fluoro, haloalkyl and hydroxy;

c) phenylalkyl or pyridinylalkyl, wherein phenylalkyl and pyridinylalkyl are optionally substituted with one to three substituents independently selected from alkyl, halogen, haloalkyl and hydroxy; or d) oxetane or oxetane substituted with alkyl.

3. The compound according to claim 1, wherein $R^1$ is adamantyl or hydroxyadamantyl.

4. The compound according to claim 1, wherein $R^1$ is trifluoromethylphenyl.

5. The compound according to claim 1, wherein $R^2$ is hydrogen.

6. The compound according to claim 1, wherein $R^2$ is methyl, ethyl or cyclopropyl.

7. The compound according to claim 1, wherein one of $R^3$ and $R^4$ is hydrogen or methyl and the other one is isopropyl, cyclopropyl or cyclopropylmethyl.

8. The compound according to claim 1, wherein $R^5$ and $R^4$ are hydrogen.

9. The compound according to claim 1 selected from
- 3,4-Dicyclopropyl-1-(2-trifluoromethyl-phenyl)-imidazolidin-2-one;
- 1-Adamantan-2-yl-4-cyclopropyl-4-methyl-imidazolidin-2-one;
- 1-Adamantan-2-yl-3,4-dicyclopropyl-imidazolidin-2-one;
- 3,4-Dicyclopropyl-1-[(Z)-5-hydroxy-adamantan-2-yl]-imidazolidin-2-one;
- 3,4-Dicyclopropyl-1-[(E)-5-hydroxy-adamantan-2-yl]-imidazolidin-2-one;
- 4-Cyclopropyl-1-[(E)-5-hydroxy-adamantan-2-yl]-4-methyl-imidazolidin-2-one;
- 4-Cyclopropyl-1-[(Z)-5-hydroxy-adamantan-2-yl]-4-methyl-imidazolidin-2-one;
- 4-Cyclopropyl-1-[(E)-5-hydroxy-adamantan-2-yl]-3,4-dimethyl-imidazolidin-2-one;
- 1-Adamantan-2-yl-3,4-dicyclopropyl-4-methyl-imidazolidin-2-one;
- 3,4-Dicyclopropyl-1-[(Z)-5-hydroxy-adamantan-2-yl]-4-methyl-imidazolidin-2-one;
- 3,4-Dicyclopropyl-1-[(E)-5-hydroxy-adamantan-2-yl]-4-methyl-imidazolidin-2-one;
- 4,4-Dicyclopropyl-1-[(Z)-5-hydroxy-adamantan-2-yl]-imidazolidin-2-one;
- 4,4-Dicyclopropyl-1-[(E)-5-hydroxy-adamantan-2-yl]-imidazolidin-2-one;
- 4-Cyclopropyl-1-[(E)-5-methoxy-adamantan-2-yl]-3,4-dimethyl-imidazolidin-2-one;
- (R or S)-4-Cyclopropyl-3-ethyl-1-[(E)-5-hydroxy-adamantan-2-yl]-4-methyl-imidazolidin-2-one; and
- (R)-3-(4-Bromo-benzyl)-4-cyclopropyl-1-((E)-5-hydroxy-adamantan-2-yl)-4-methyl-imidazolidin-2-one.

10. A process for the preparation of a compound according to formula (III) of claim 1:

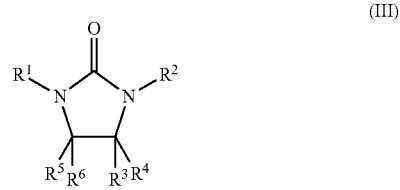

comprising the step of:

reacting a compound according to formula

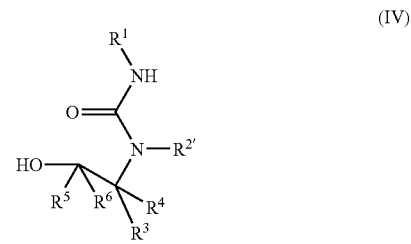

in the presence of a base.

11. A pharmaceutical composition, comprising a therapeutically effective amount of a compound according to claim 1 and a therapeutically inert carrier.

* * * * *